(12) United States Patent
Woehr et al.

(10) Patent No.: US 7,601,139 B2
(45) Date of Patent: *Oct. 13, 2009

(54) SPRING LAUNCHED NEEDLE SAFETY CLIP

(75) Inventors: Kevin Woehr, Felsberg (DE); Helmut Freigang, Koerle (DE); Juergen Fuchs, Bad Emstal (DE); Juergen Reuter, Alheim (DE); Klaus Siemon, Koerle (DE); Joerg Wende, Volkmarsen (DE); Frank Hilberg, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 1264 days.

This patent is subject to a terminal disclaimer.

(21) Appl. No.: 10/251,735

(22) Filed: Sep. 20, 2002

(65) Prior Publication Data

US 2003/0144627 A1     Jul. 31, 2003

Related U.S. Application Data

(63) Continuation-in-part of application No. 09/965,055, filed on Sep. 26, 2001, now Pat. No. 6,623,458.

(51) Int. Cl.
*A61M 5/32* (2006.01)
(52) U.S. Cl. .................... 604/192; 110/198; 110/263
(58) Field of Classification Search ............. 604/110, 604/192, 198, 162, 164.08, 263, 268; 128/919
See application file for complete search history.

(56) References Cited

U.S. PATENT DOCUMENTS 4,725,267 A    2/1988   Vaillancourt
4,775,369 A    10/1988  Schwartz
4,795,432 A    1/1989   Karczmer
4,804,371 A    2/1989   Vaillancourt
4,813,940 A    3/1989   Parry
4,846,809 A    7/1989   Sims
4,850,977 A    7/1989   Bayless
4,850,994 A    7/1989   Zerbst et al.
4,863,434 A    9/1989   Bayless
4,863,435 A    9/1989   Sturman et al.

(Continued)

FOREIGN PATENT DOCUMENTS

DE          3802353 A1     8/1989

(Continued)

*Primary Examiner*—Kevin C Sirmons
*Assistant Examiner*—Bhisma Mehta
(74) *Attorney, Agent, or Firm*—Klein, O'Neill & Singh, LLP

(57) ABSTRACT

A hypodermic needle assembly configured such that the movement of a needle shield into position to block the needle tip occurs as a direct consequence of a longitudinal force applied by insertion of a syringe plunger is provided. The hypodermic needle assembly according to the present invention comprises a needle, a needle hub, and a safety spring clip assembly, the safety spring clip assembly being configured to automatically launch from the needle hub and slide along the needle until the spring clip meets a needle stop at the needle tip, thus preventing the guard from being removed from the needle shaft. A method of using the hypodermic needle assembly according to the present invention is also provided, which includes the method of launching the spring clip with a syringe having multiple advancing mechanisms.

33 Claims, 27 Drawing Sheets

U.S. PATENT DOCUMENTS

| | | | |
|---|---|---|---|
| 4,887,998 A * | 12/1989 | Martin et al. ............... 604/110 |
| 4,894,055 A | 1/1990 | Sudnak |
| 4,900,311 A | 2/1990 | Stern et al. |
| 4,927,416 A | 5/1990 | Tomkiel |
| 4,929,237 A | 5/1990 | Medway |
| 4,929,241 A | 5/1990 | Kulli |
| 4,950,241 A | 8/1990 | Ranford |
| 4,955,866 A | 9/1990 | Corey |
| 4,978,344 A | 12/1990 | Dombrowski et al. |
| 4,985,021 A | 1/1991 | Straw et al. |
| 5,015,240 A | 5/1991 | Soproni et al. |
| 5,053,017 A | 10/1991 | Chamuel |
| 5,059,180 A | 10/1991 | McLees |
| 5,106,379 A | 4/1992 | Leap |
| 5,171,300 A | 12/1992 | Blake, III et al. |
| 5,205,826 A | 4/1993 | Chen |
| 5,215,528 A | 6/1993 | Purdy et al. |
| 5,232,458 A | 8/1993 | Chen |
| 5,242,402 A | 9/1993 | Chen |
| 5,273,539 A | 12/1993 | Chen |
| 5,273,543 A | 12/1993 | Bell et al. |
| 5,295,963 A | 3/1994 | Deeks |
| 5,322,517 A | 6/1994 | Sircom et al. |
| 5,328,475 A | 7/1994 | Chen |
| 5,328,482 A | 7/1994 | Sircom et al. |
| 5,334,158 A | 8/1994 | McLees |
| 5,336,187 A | 8/1994 | Terry et al. |
| 5,344,408 A | 9/1994 | Partika |
| 5,360,409 A | 11/1994 | Boyd, III et al. |
| 5,364,370 A | 11/1994 | Szerlip et al. |
| 5,368,568 A * | 11/1994 | Pitts et al. ............... 604/110 |
| 5,378,240 A | 1/1995 | Curie et al. |
| 5,425,720 A | 6/1995 | Rogalsky et al. |
| 5,460,611 A | 10/1995 | Alexander |
| 5,466,223 A | 11/1995 | Bressler et al. |
| 5,549,570 A | 8/1996 | Rogalsky |
| 5,554,131 A | 9/1996 | Lacivita |
| 5,584,818 A | 12/1996 | Morrison |
| 5,716,341 A | 2/1998 | Saito |
| 5,720,727 A | 2/1998 | Alexander et al. |
| 5,785,687 A | 7/1998 | Saito |
| 5,795,336 A | 8/1998 | Romano et al. |
| 5,814,017 A | 9/1998 | Kashmer |
| 5,817,070 A | 10/1998 | Tamaro |
| 5,879,337 A | 3/1999 | Kuracina et al. |
| 5,919,168 A | 7/1999 | Wheeler |
| 6,001,080 A | 12/1999 | Kuracina et al. |
| 6,015,396 A | 1/2000 | Buttgen et al. |
| 6,165,153 A | 12/2000 | Kashmer |
| 6,171,284 B1 | 1/2001 | Kao et al. |
| 6,196,997 B1 | 3/2001 | Saito |
| 6,595,955 B2 | 7/2003 | Ferguson et al. |
| 6,623,458 B2 * | 9/2003 | Woehr et al. ............... 604/192 |
| 6,860,871 B2 * | 3/2005 | Kuracina et al. ............ 604/192 |
| 6,945,960 B2 * | 9/2005 | Barker et al. ............... 604/198 |
| 7,004,929 B2 * | 2/2006 | McWethy et al. ............ 604/198 |
| 2003/0093009 A1 | 5/2003 | Newby et al. |
| 2004/0010227 A1 * | 1/2004 | Riesenberger et al. ...... 604/110 |

FOREIGN PATENT DOCUMENTS

| | | |
|---|---|---|
| DE | 43 14 395 C1 | 12/1994 |
| EP | 0 979 660 A1 | 2/2000 |
| EP | 1316325 A1 | 6/2003 |
| WO | WO 95/27524 | 10/1995 |
| WO | WO 99/08742 | 2/1999 |

* cited by examiner

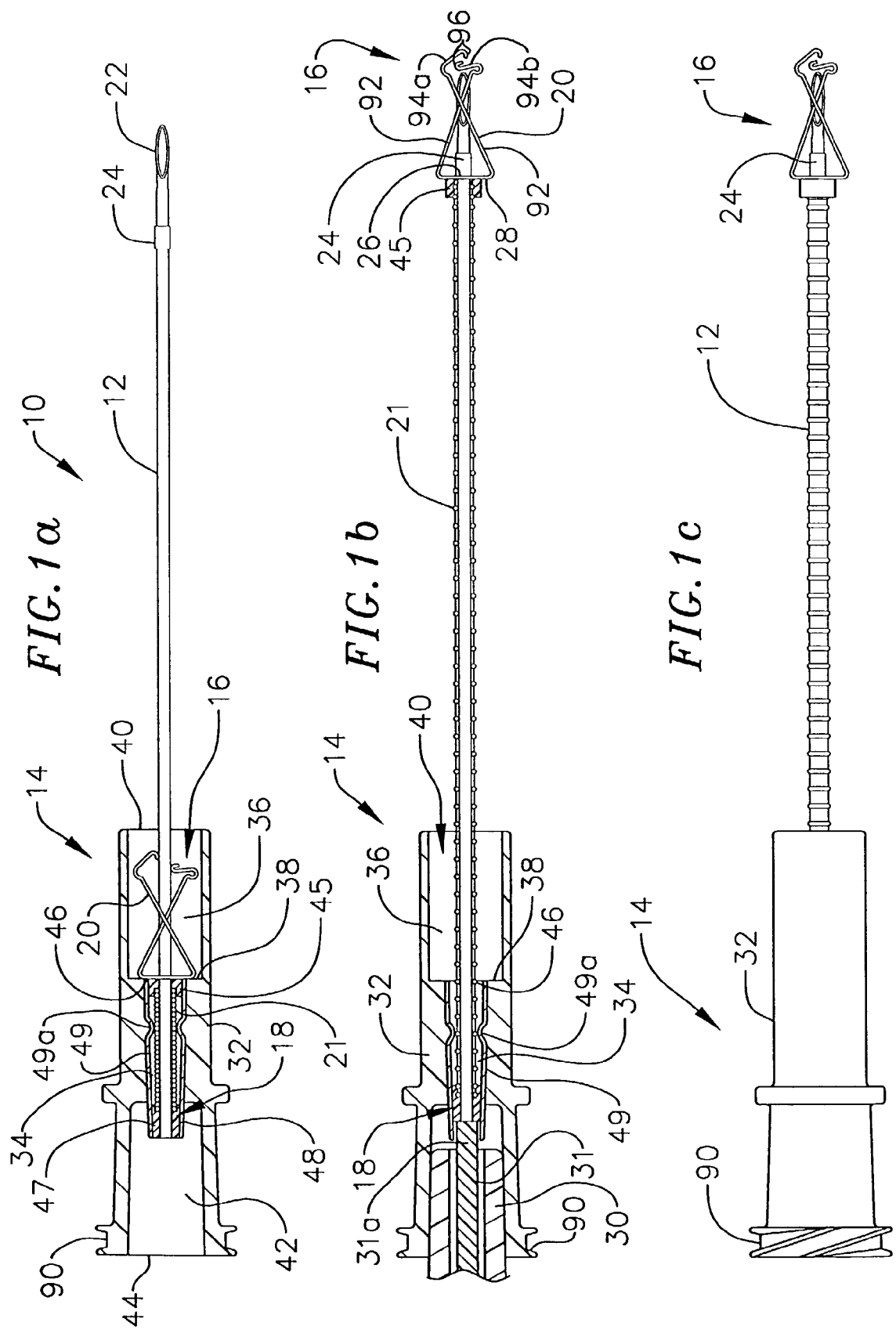

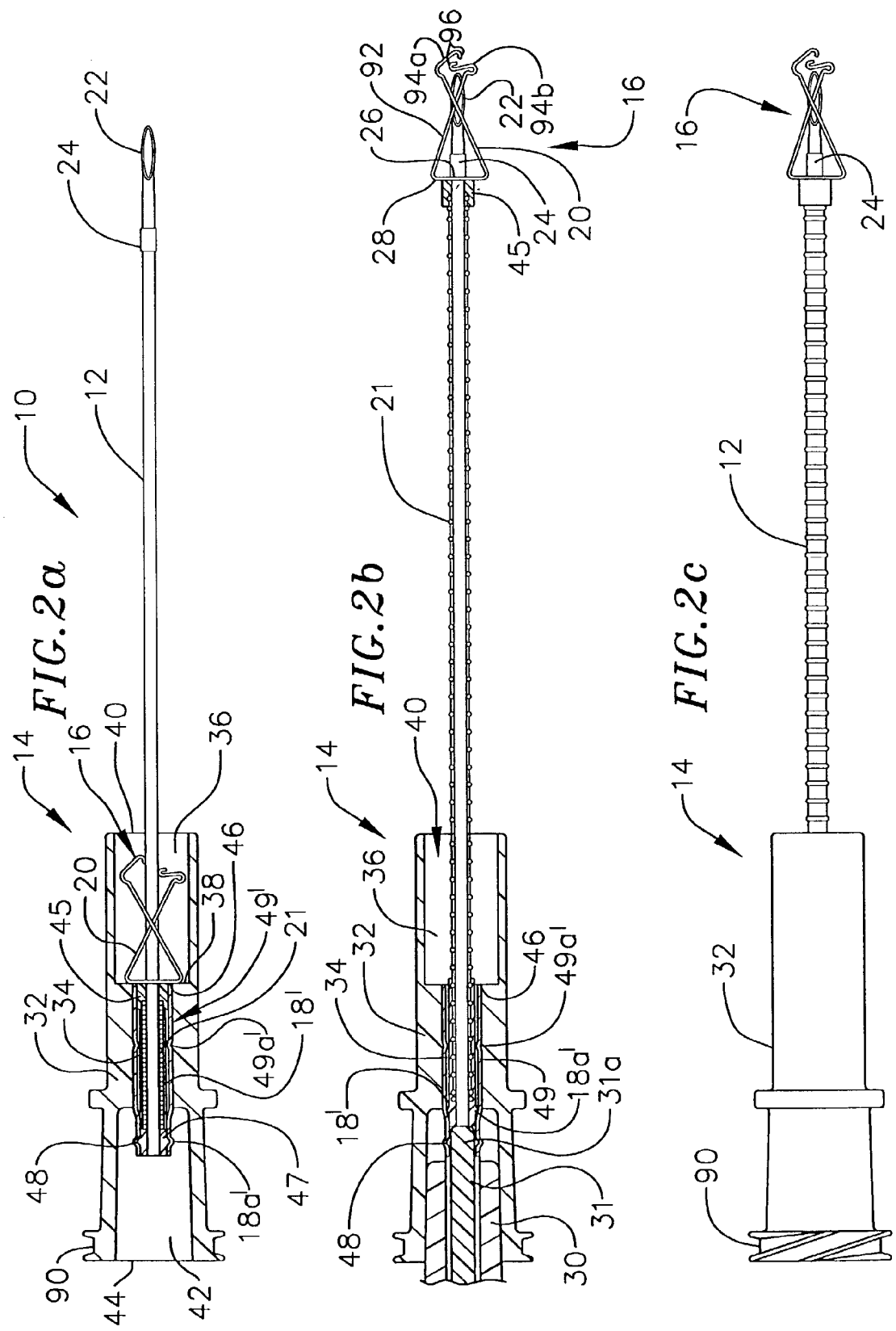

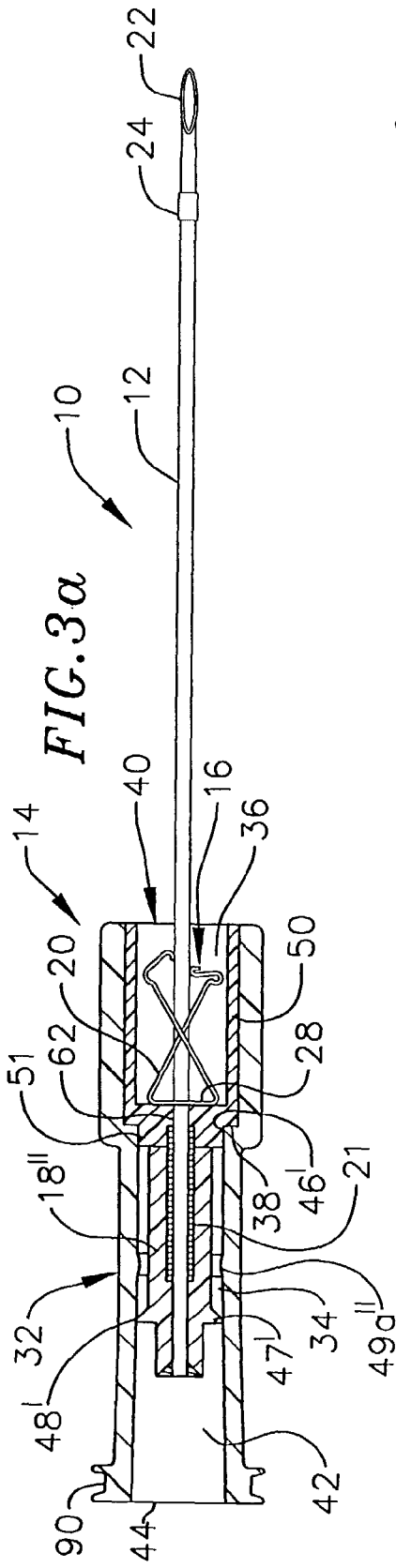

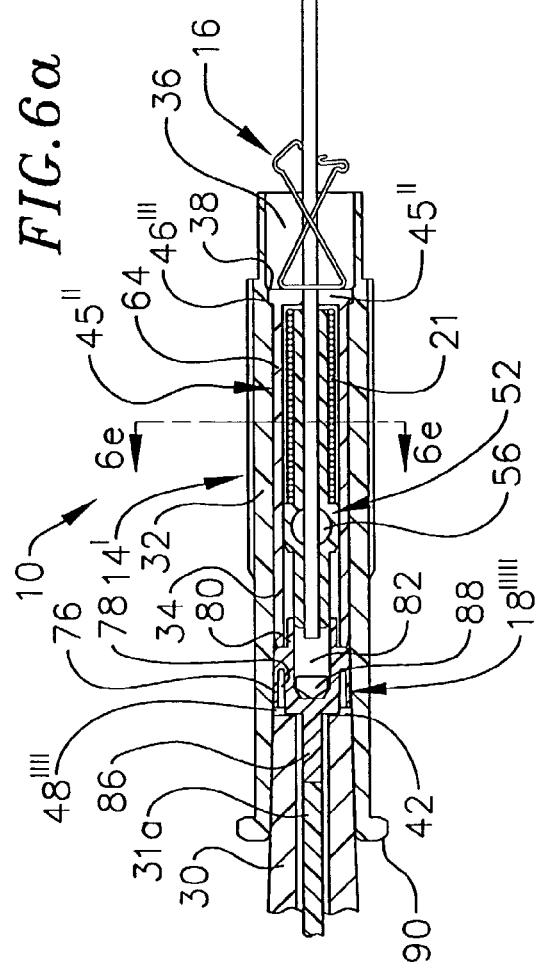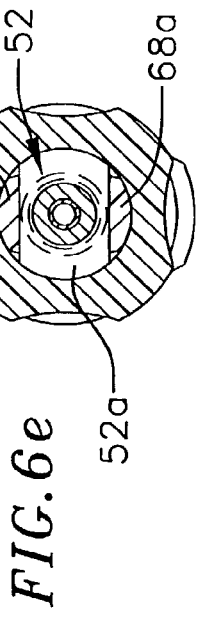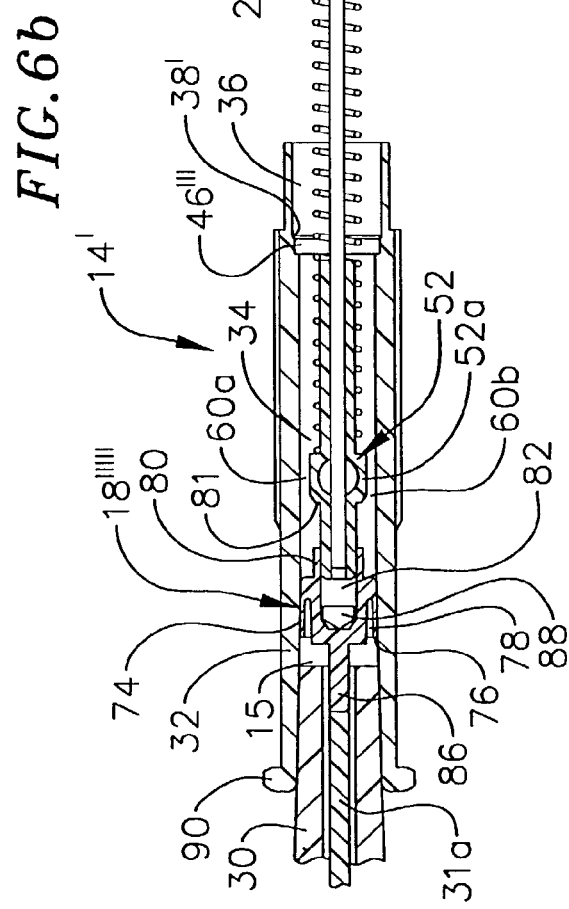

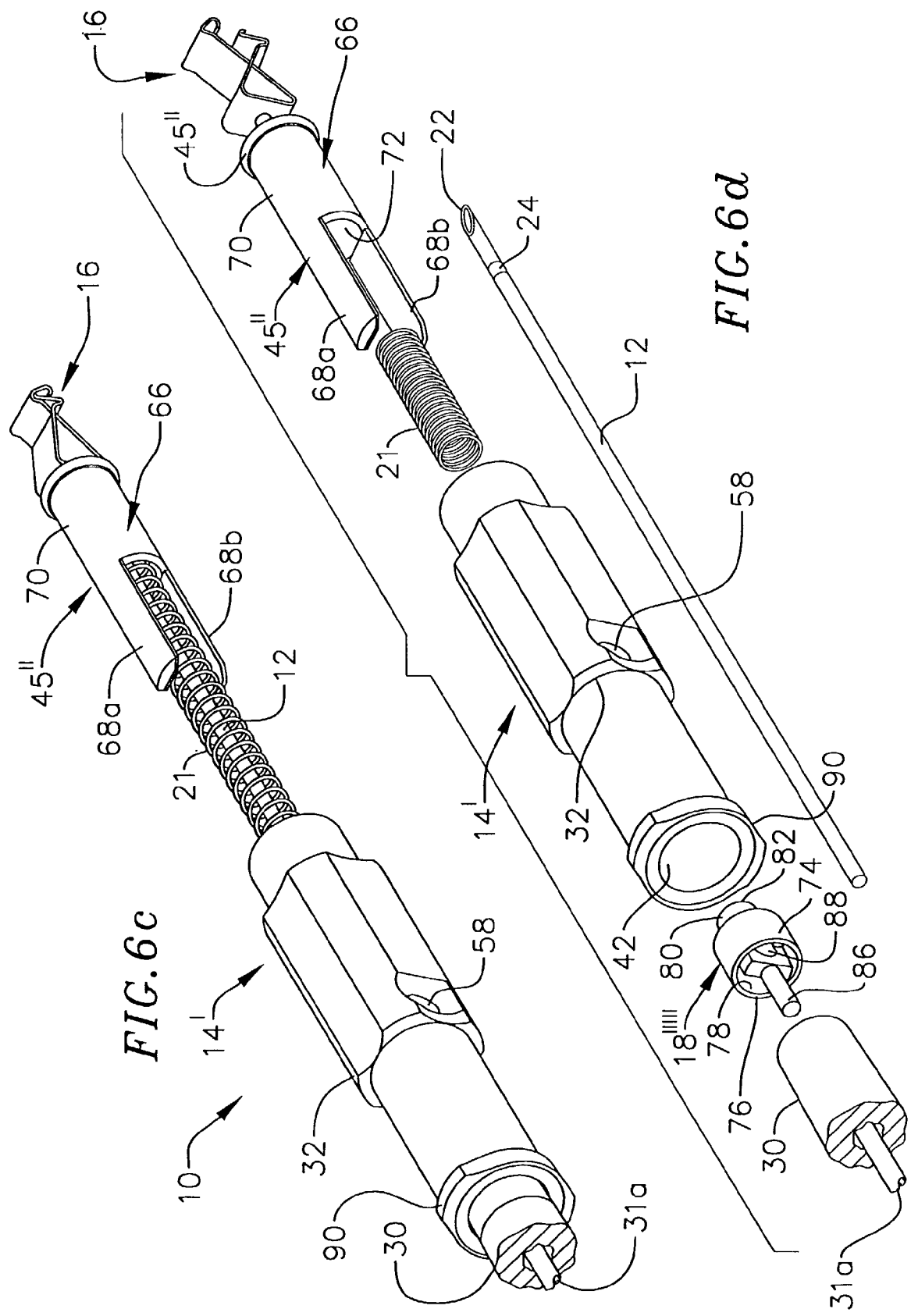

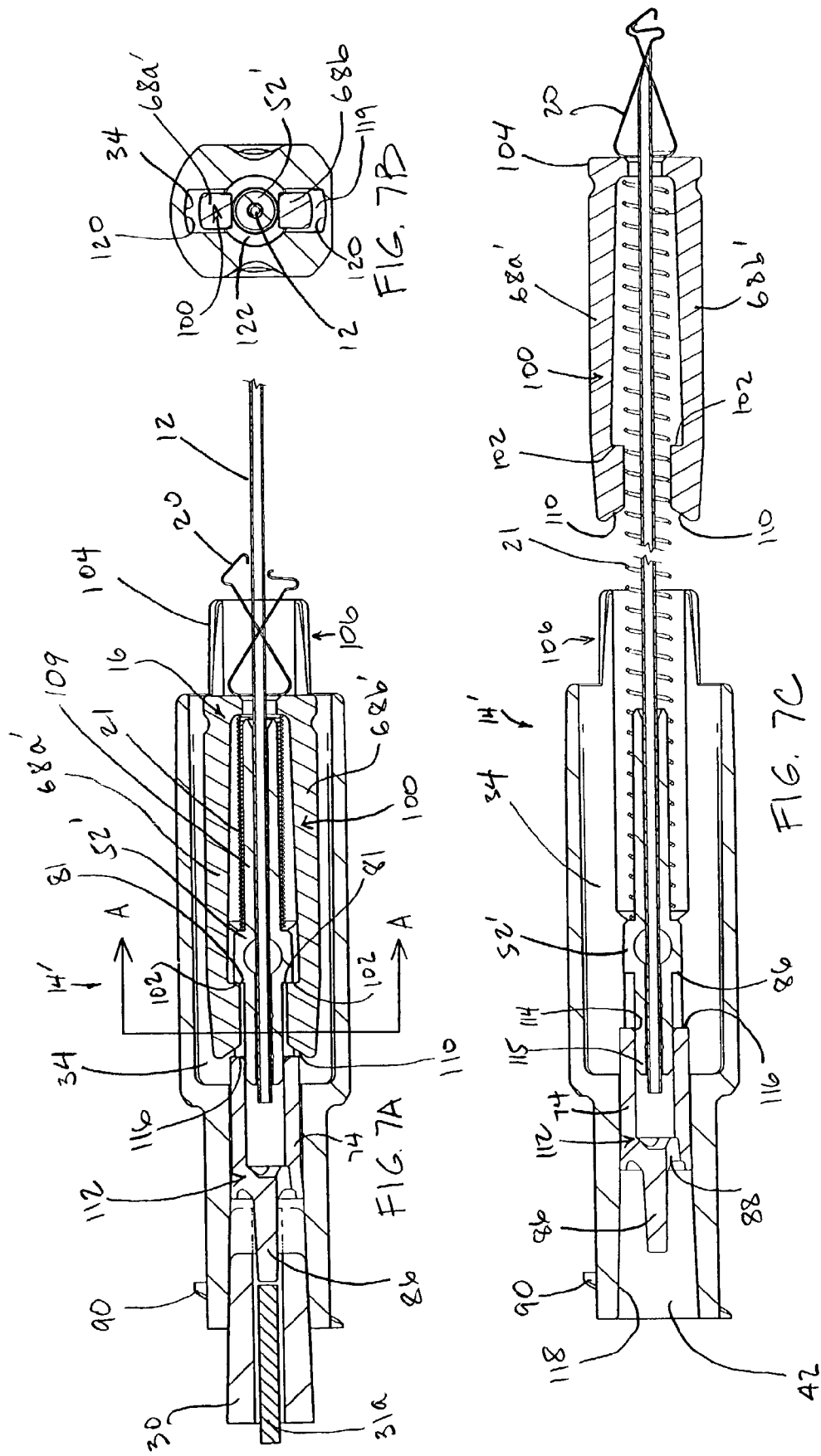

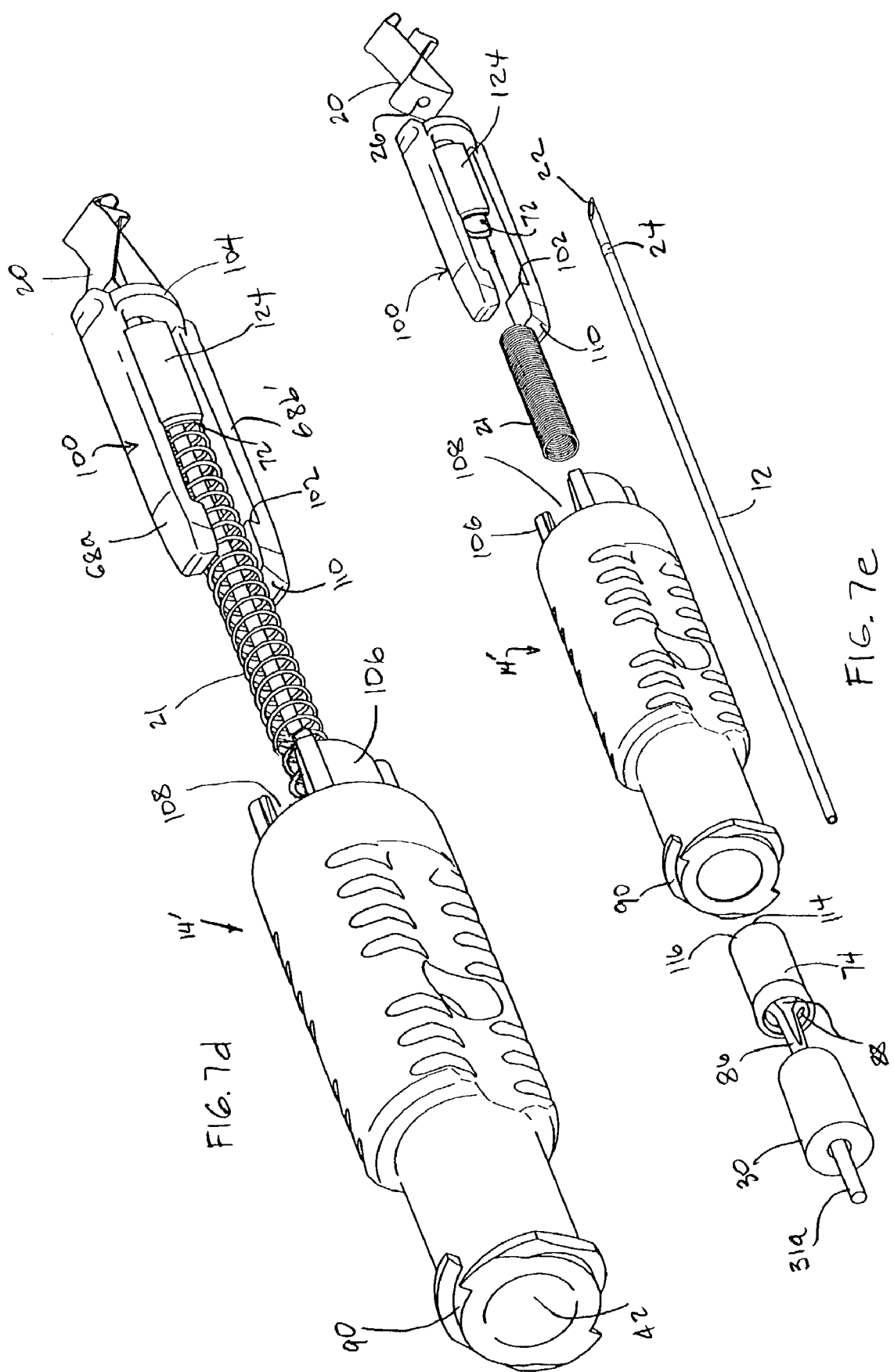

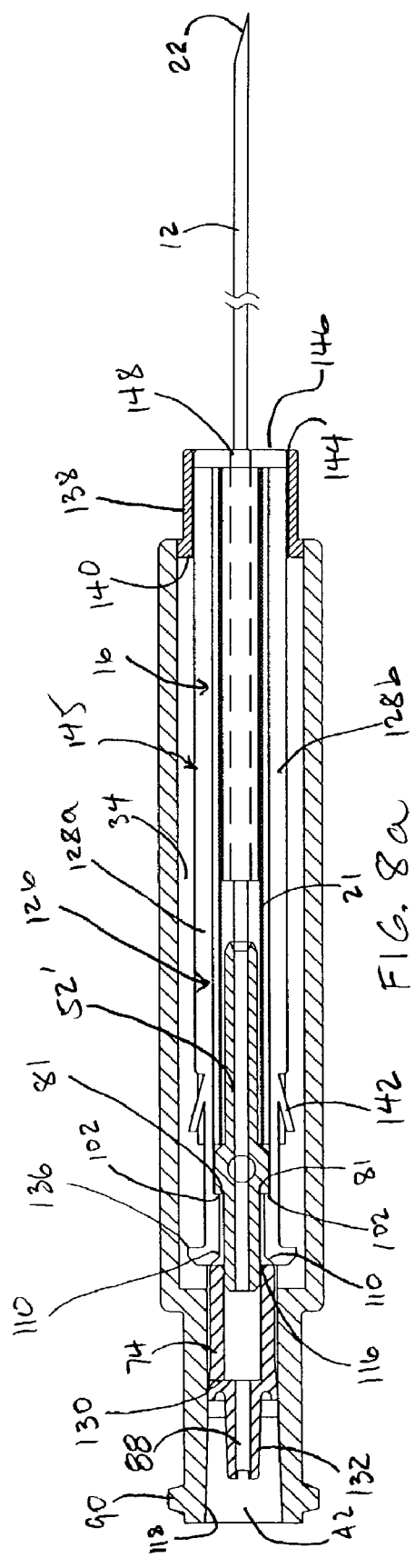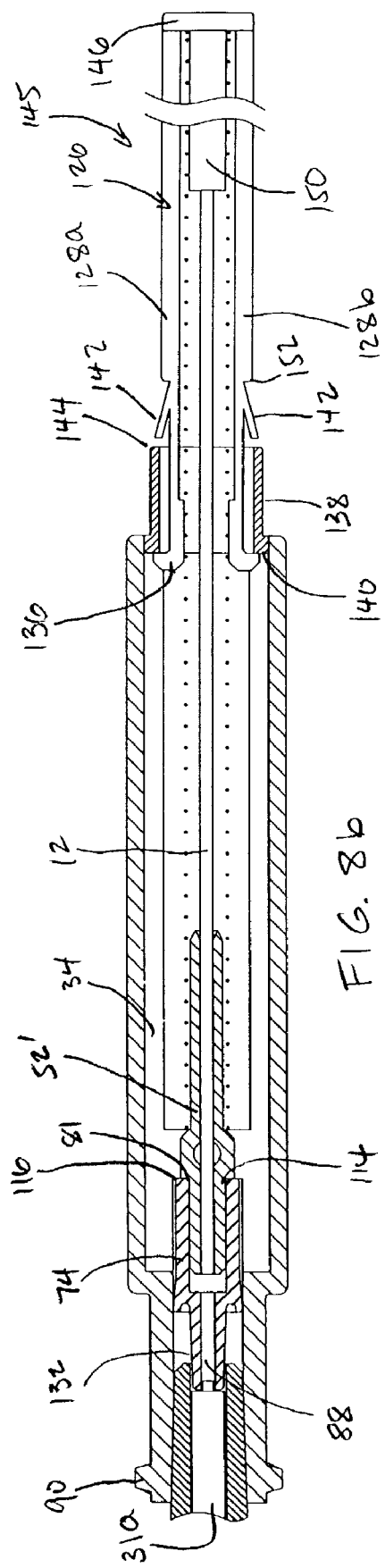

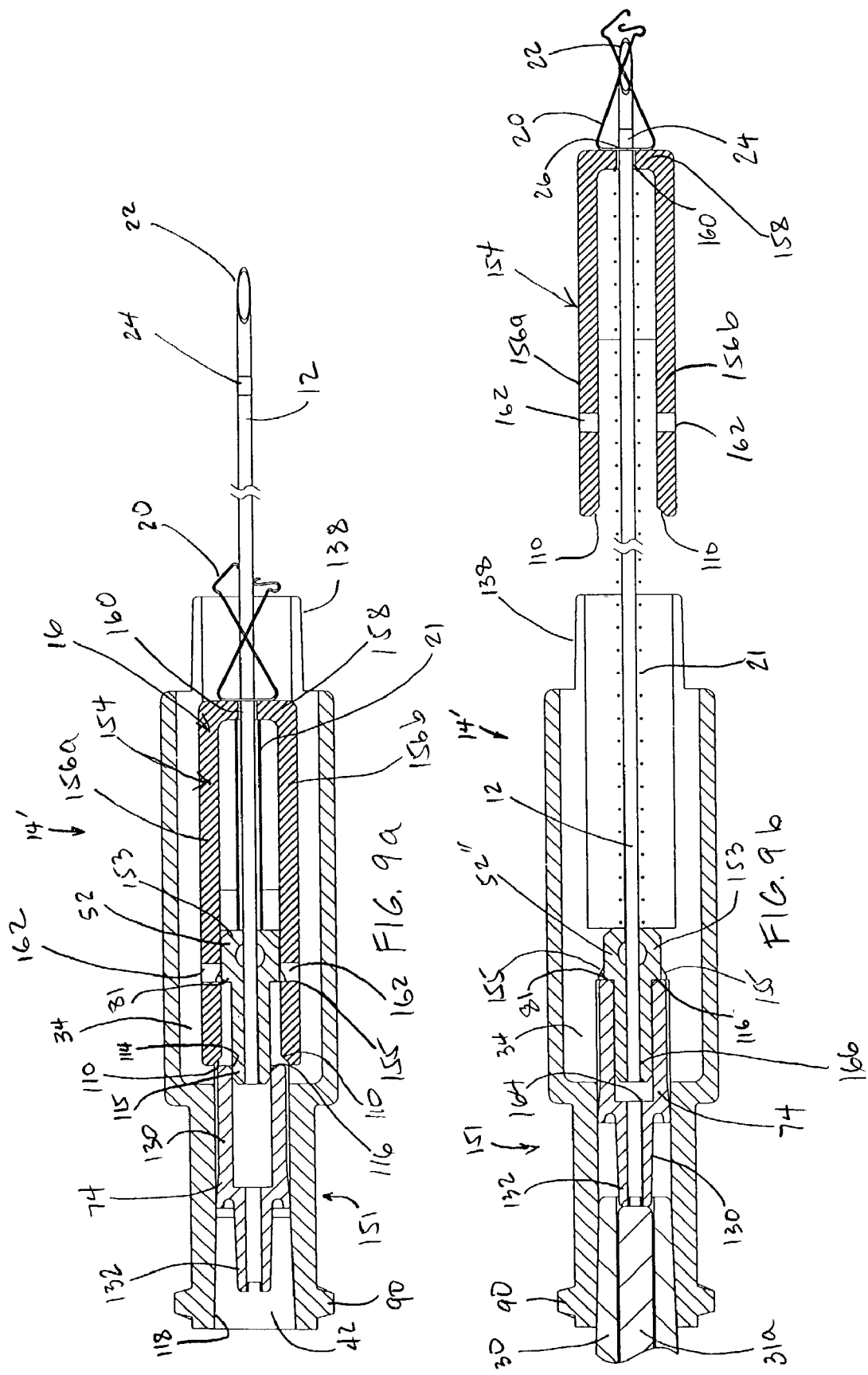

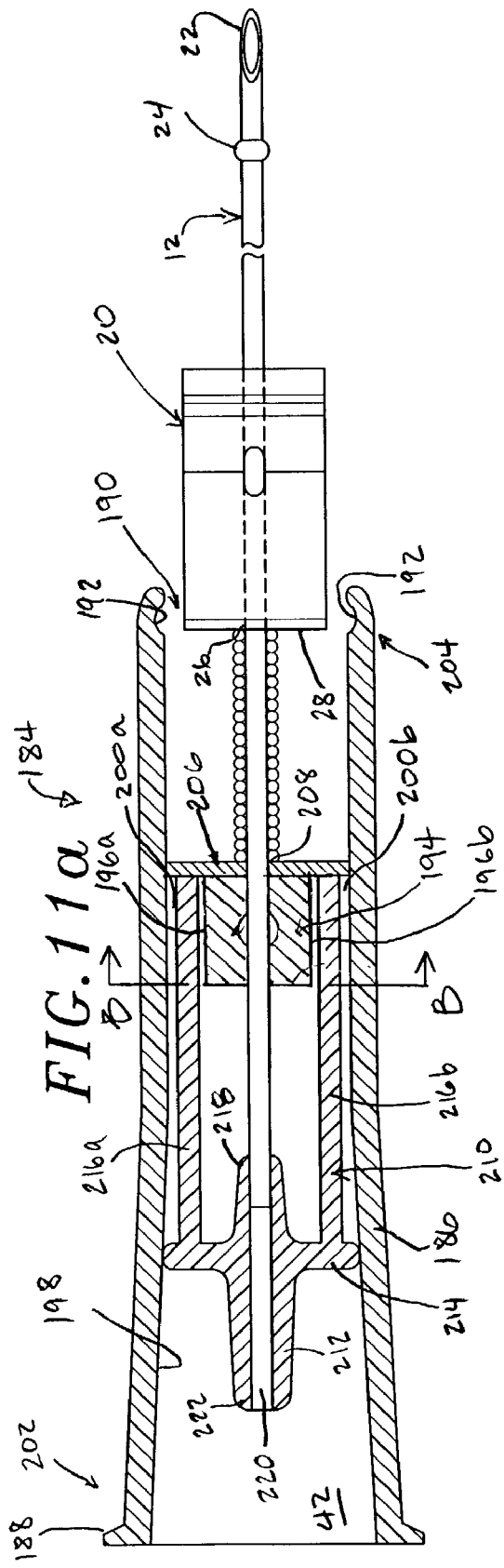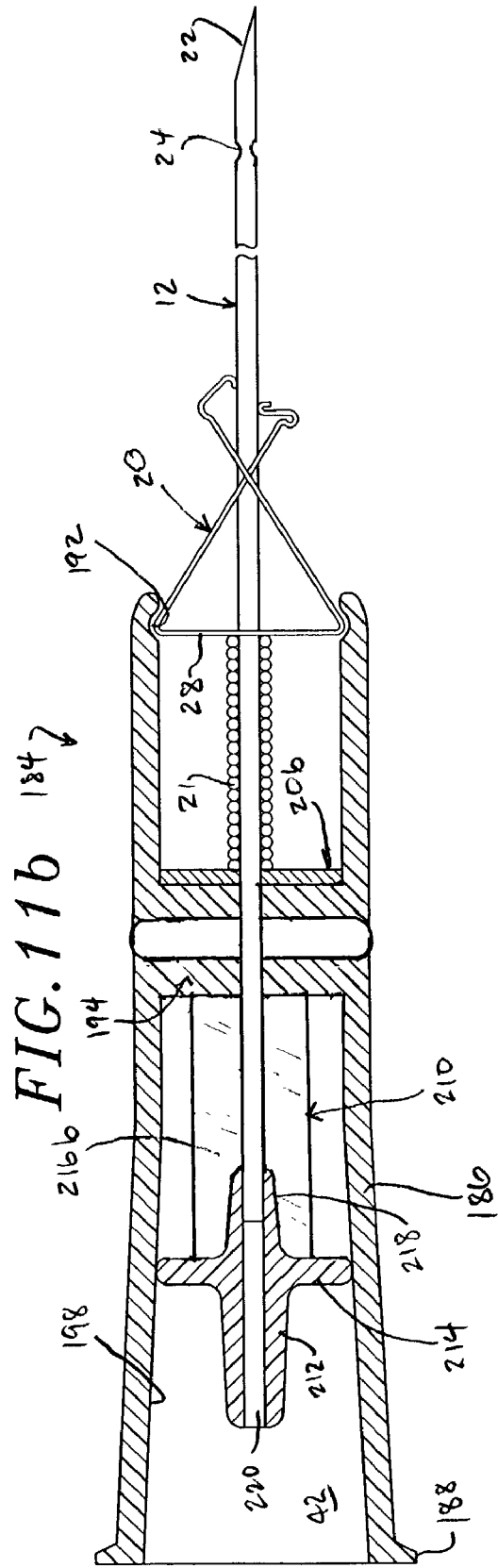

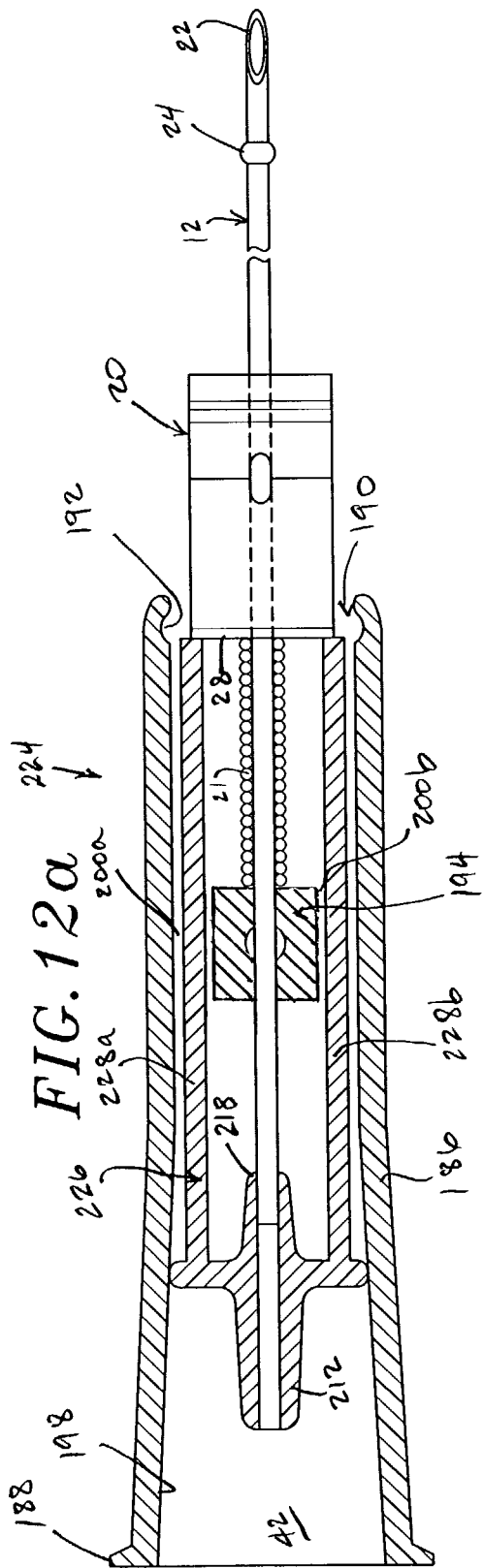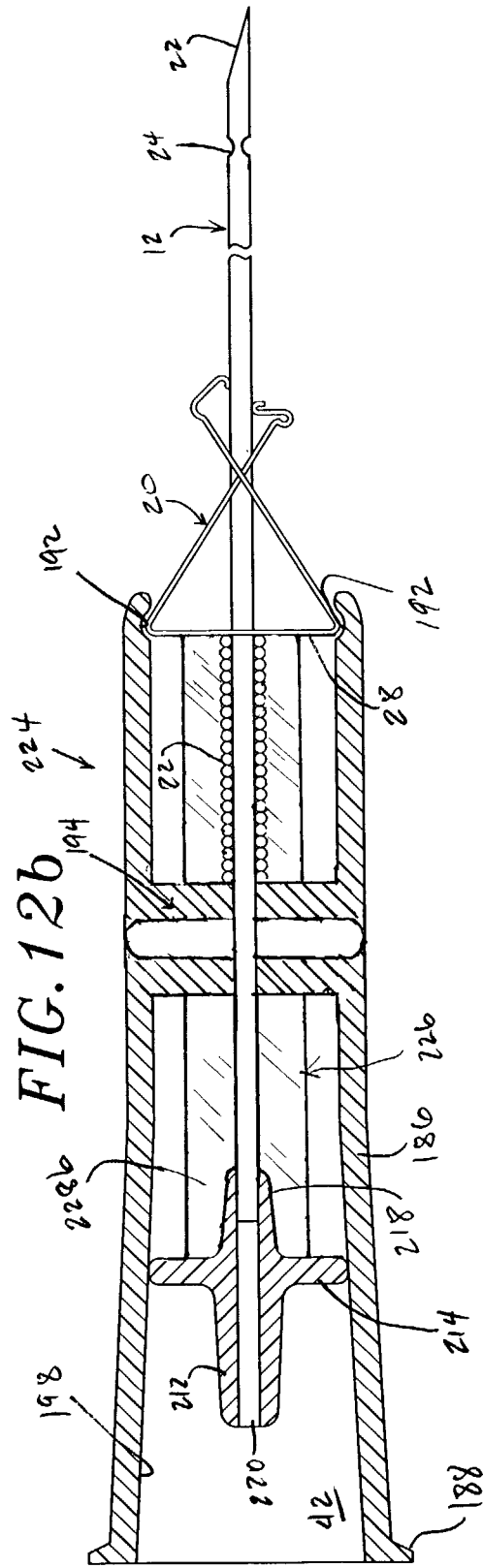

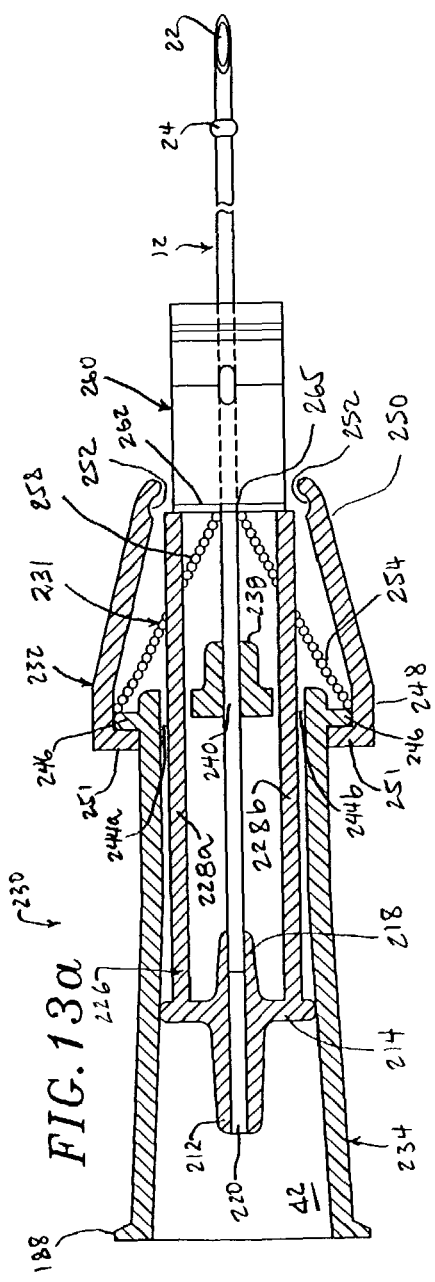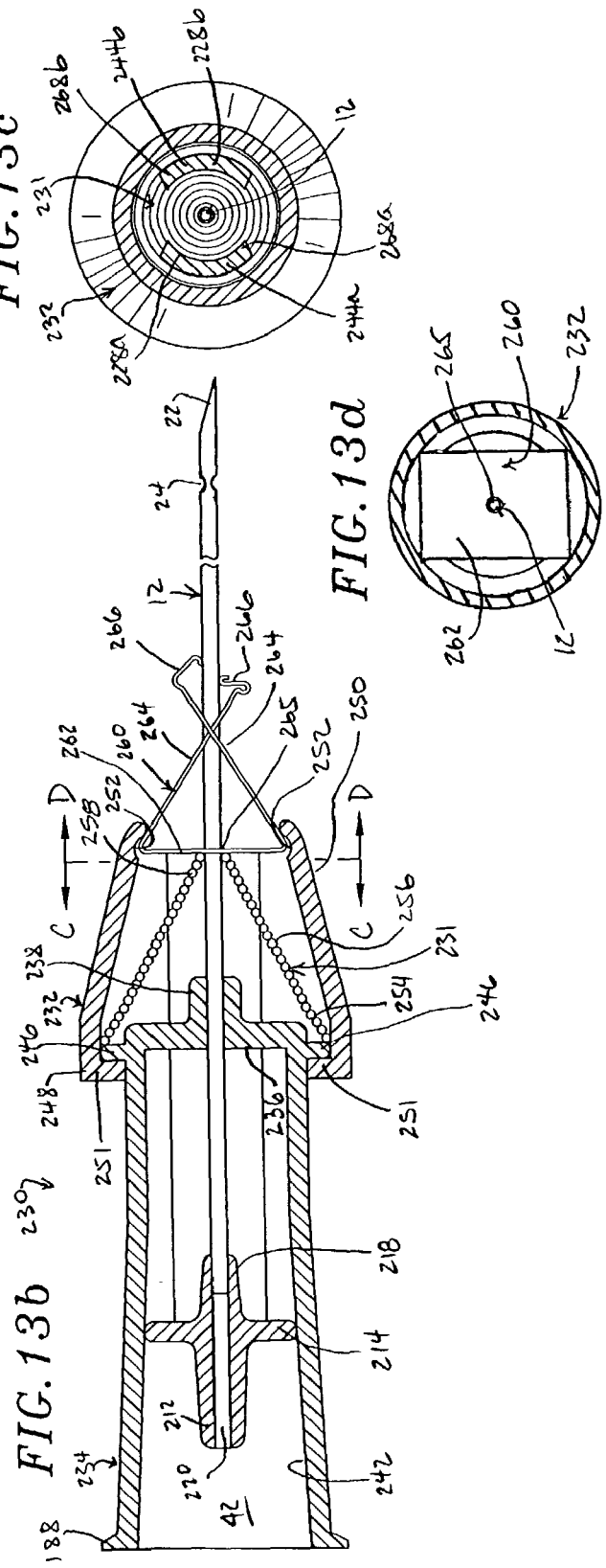
FIG.13a
FIG.13b
FIG.13c
FIG.13d

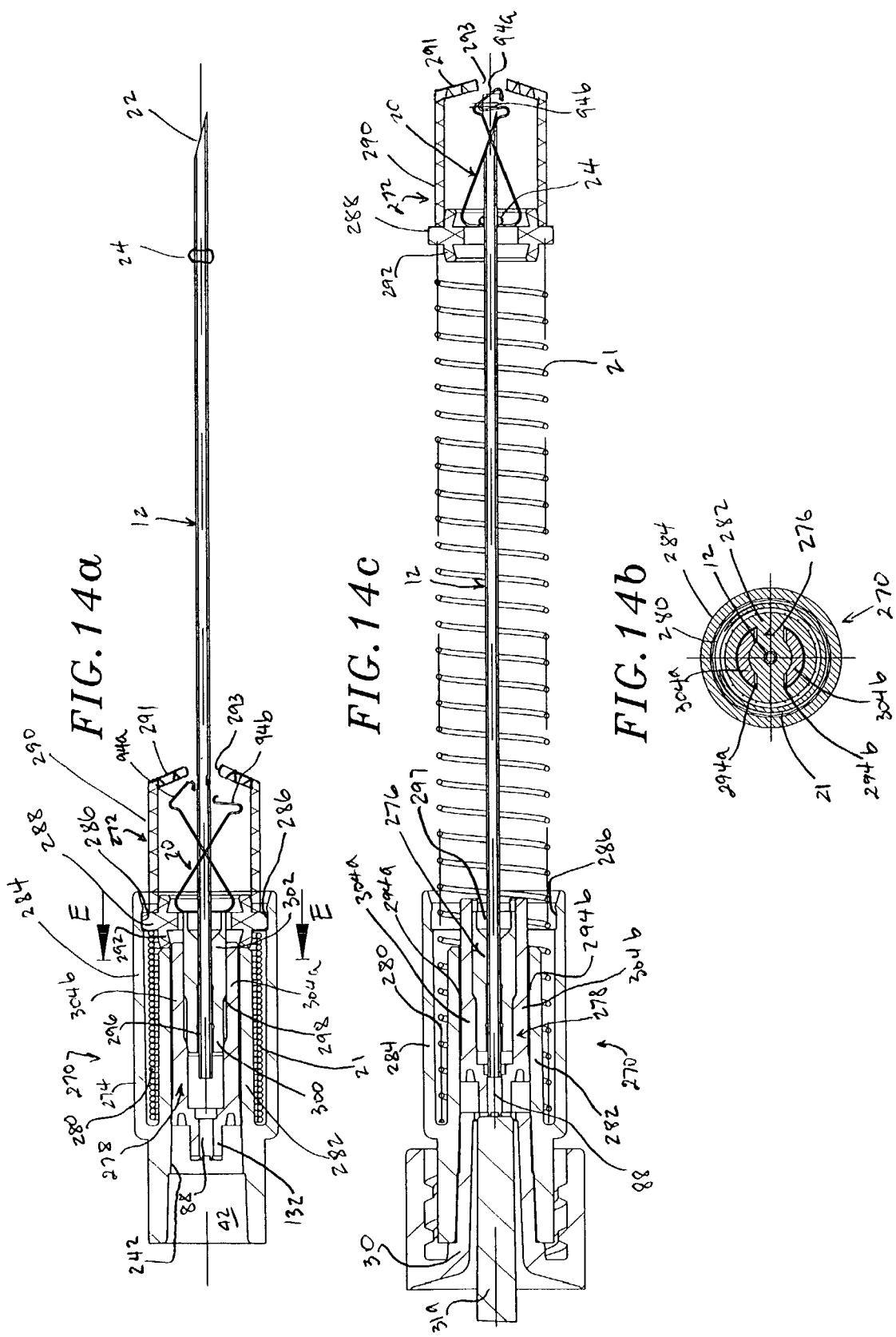

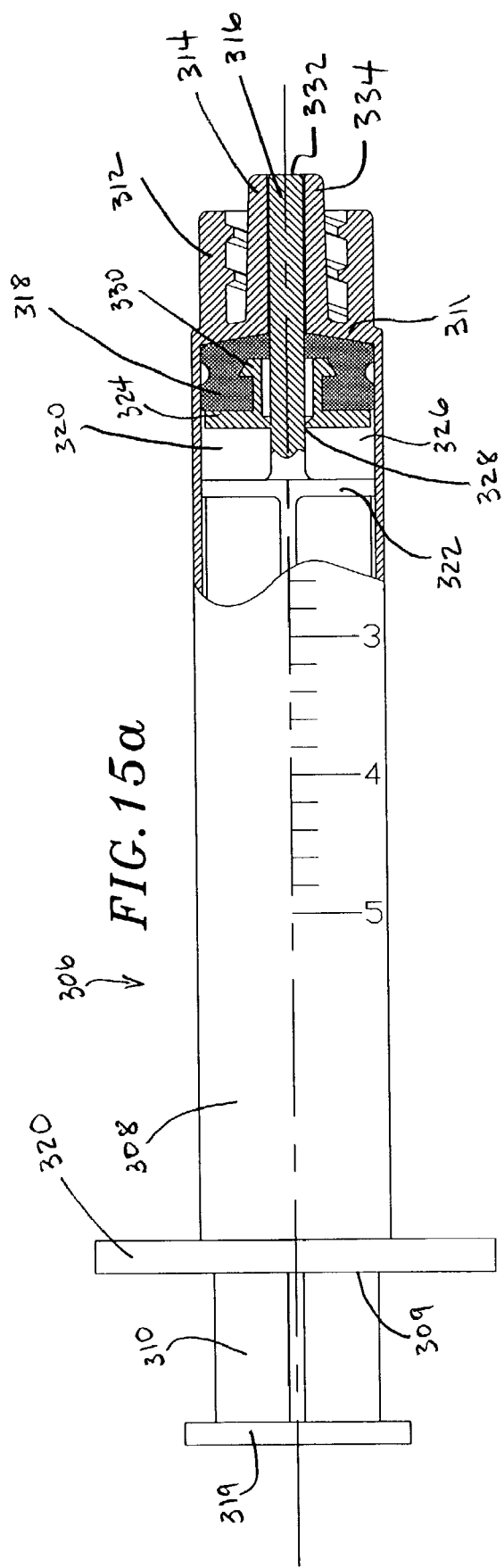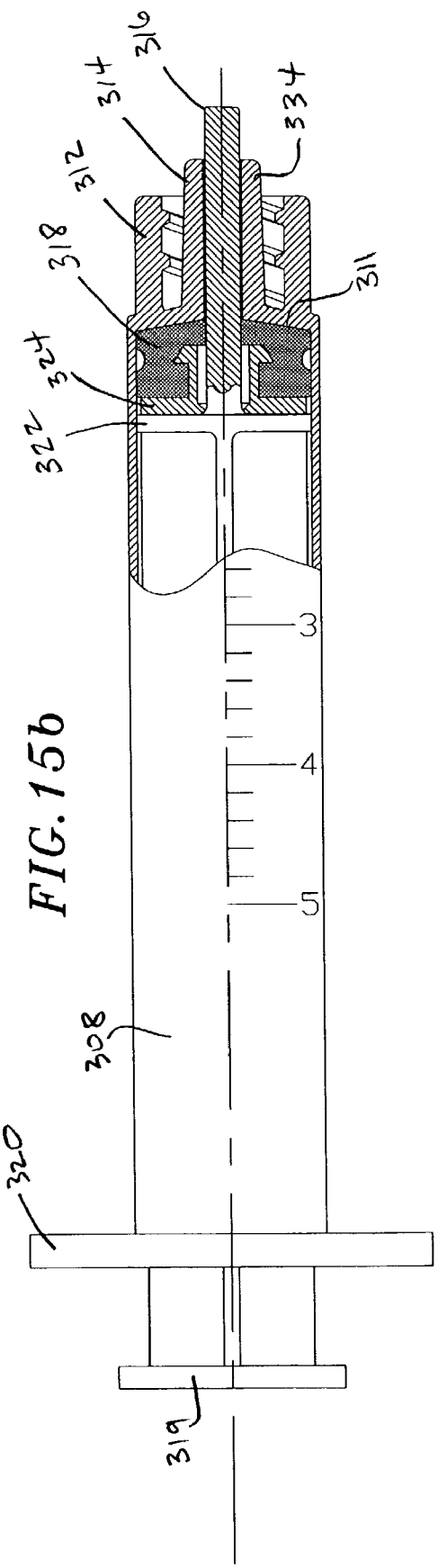

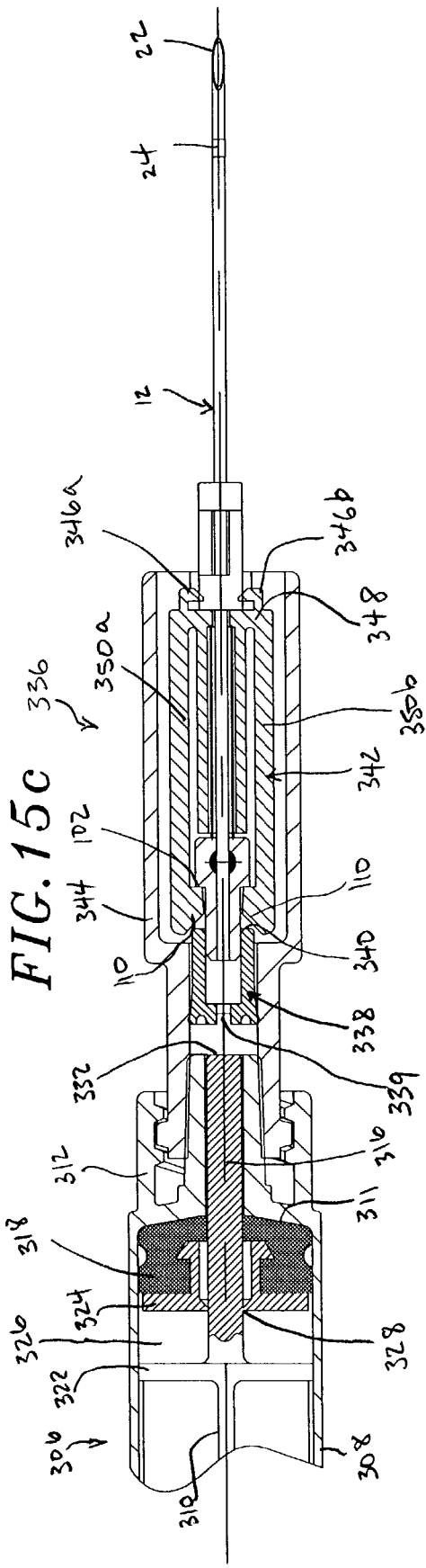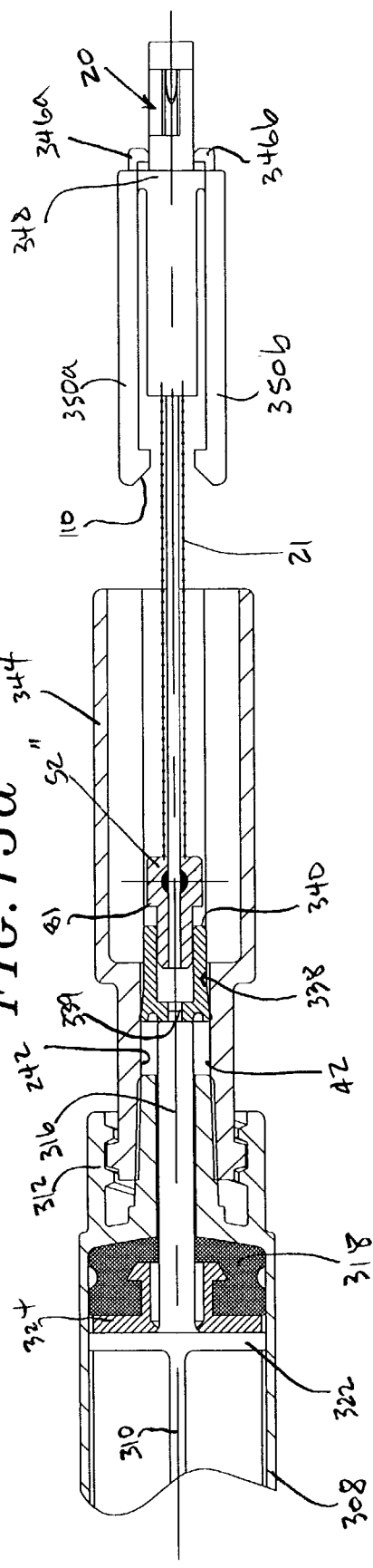

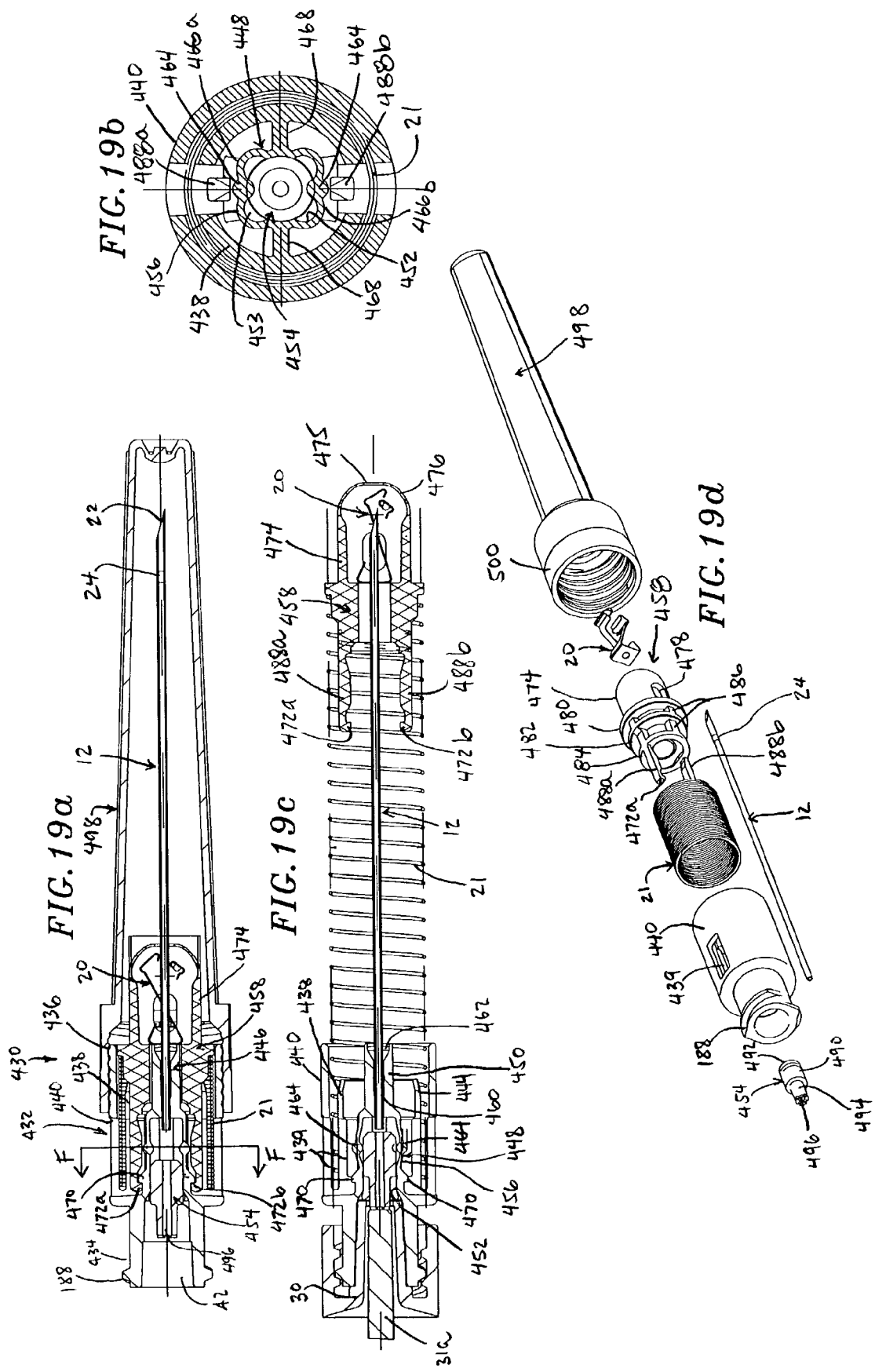

SPRING LAUNCHED NEEDLE SAFETY CLIP

CROSS-REFERENCE TO RELATED APPLICATION

This is a continuation-in-part of application Ser. No. 09/965,055 entitled "Spring Launched Needle Safety Clip" filed Sep. 26, 2001, now U.S. Pat. No. 6,623,458, the content of which is expressly incorporated herein by reference.

Hypodermic needle assemblies are discussed herein which include a needle assembly having a resilient member for launching a safety clip device to block the tip of a disposable needle after use to facilitate the safe handling of such needles. Syringes with distinct mechanisms for dispensing medication and for launching the safety clip are also discussed.

BACKGROUND

Medical care of individuals requires the widespread use of needles for taking blood samples, intravenous drug delivery, and the introduction or removal of other fluids via cannula, needles, or syringes. In the current context, the use of hypodermic needles to deliver plasma, anesthetics, or other medications has become commonplace in medicine, science, veterinary medicine, and biotechnology. The use of a hypodermic needle typically involves first inserting a needle into the patient, injecting a substance or withdrawing a substance as required, and then removing the needle from the patient. In most applications, the withdrawn and contaminated needle must be handled very carefully during disposal to avoid needle stick injury.

To help prevent health care workers from becoming injured, guards have been developed to block the tip of these needles after use. Indeed, needle stick protection for medical professionals has become of particular importance in recent years because of the prevalence of potentially fatal infectious diseases, such as, for example, Acquired Immune Deficiency Syndrome (AIDS) and hepatitis, that can be transmitted by the exchange of bodily fluids through inadvertent wounds caused by accidental needle tip pricks after withdrawal from infected patients. Accordingly, many kinds of needle protection devices are available for providing post injection needle stick protection.

Devices which have been introduced to provide added protection against punctures by used needles fall into three basic categories, those which hide the withdrawn needle within a needle shield launched via a needle shield launching mechanism, those which require placement of a separate needle guard, and those which include a sliding shield which must be manually pushed along the needle shaft and over the tip of the used needle. Most of these needle guards are cumbersome and interfere with a single-handed procedure, and or require additional complicated pieces to attach the needle guard to the needle tip.

Of the first type, i.e., devices which hide the withdrawn needle within a launched needle shield, there are several designs. However, all of these designs have undesirable features which make them unsuitable for many applications. For example, in one conventional design, a spring biased needle shield is provided which lockingly engages with the needle tip when the user manually activates the spring mechanism after the needle is withdrawn from the patient. However, while this mechanism provides for preventing the needle shield from disengaging and moving back down the length of the needle, the needle shields are only frictionally engaged to the tip of the needle, such that it is possible to slip the needle shield off of the distal end of the needle leaving the needle tip exposed. In addition, this design requires the user to manually activate the spring mechanism, which adds to the complexity of the design, manufacture, and use of the hypodermic needle assembly.

In another conventional design, the needle has a slightly expanded portion at the tip which prevents the needle shield from sliding off of the distal end of the needle once engaged. However, the needle shields utilizing this design still require the user to manually activate a second mechanism that then engages the needle guard, adding to the complexity of the design, manufacture and use of the hypodermic needle assembly.

Within this first category there are also a number of hypodermic needle assemblies for shielding the needle tip from being exposed once the needle is withdrawn from the patient which are automatically activated by the depression of the hypodermic plunger. However, the needle guards provided in most of these prior art designs consist of a simple hollow sleeve having an open distal end. While this design does provide protection from most inadvertent contact with the needle tip, it is still possible with such designs for a user to accidentally or purposefully insert a finger into the open distal end of the needle guard sleeve and thus come into contact with the contaminated needle tip.

Of the second and third types of needle shields, i.e., those which require placement of a separate needle guard or which use a shield that is manually pushed along a needle, there are several different designs. A number of these needle shields include either a spring-clip fitting or a frictional fitting, which are either placed directly on the tip of the needle or are movable from the base of the needle to the tip of the needle along the longitudinal direction of the needle. In the later embodiment, the user manually slides the needle shield toward the tip of the needle to thereby engage the needle shield around the needle tip. However, these manually activated designs require that the user either slide or apply the needle shield to the tip of the needle by hand, significantly raising the risk of unintentional contact with the needle tip.

Present day techniques thus offer a large number of solutions for protecting medical staff from used needles. However, as noted above, the known solutions suffer from at least one serious drawback. Accordingly, a hypodermic needle assembly is needed which reduces the risk of unintentional exposure of the used needle after use by automatically engaging the needle shield once injection is complete, without the need for additional complex mechanisms or cumbersome user operation.

SUMMARY OF THE INVENTION

According to the present invention, there is provided a hypodermic needle assembly designed such that the action of compressing the plunger of the syringe automatically activates a resilient, member-loaded needle shield such that the needle shield moves into position to block the needle tip, such that there is no risk of accidental injury and infection from an exposed needle and there is no need for the activation of any additional mechanisms to complete the needle shielding process.

The safety hypodermic needle assembly provided in accordance with practice of the present invention is a single-use device that is independent from the syringe assembly and is detachably attachable thereto. In one aspect, the safety hypodermic needle assembly comprises a needle hub having open proximal and distal ends, wherein the open proximal end defines a chamber configured to engage the tip of a syringe, and wherein the syringe tip has a plunger pin slidably mounted therein. A needle is provided which defines a longitudinal axis and has proximal and distal end portions. The distal end portion of the needle comprises a sharp needle tip, and the proximal end portion is mounted in the needle hub. The needle hub is configured such that the proximal end portion of the needle is in fluid communication with the syringe tip engagement chamber, and the distal end portion of the needle extends out from the distal end of the needle hub. A needle tip safety guard assembly is provided which comprises a needle tip safety guard which is mounted on the needle and arranged at the distal end portion of the needle hub. The needle tip safety guard assembly has a proximal end portion disposed within the open distal end of the needle hub, and the needle tip safety guard has a needle opening therein through which the needle extends. The needle tip safety guard assembly is configured such that when the needle tip safety guard is urged over the needle tip, the needle tip guard is engaged to block the needle tip.

A needle guard activator assembly is provided for urging the needle tip safety guard in a distal direction along the needle. The activator assembly comprises a pressure trigger and a resilient member, wherein the pressure trigger is mounted in the needle hub and is arranged between the syringe plunger when the syringe tip is in the syringe tip engagement chamber and the needle tip safety guard, such that when the syringe plunger is translated distally, the plunger pin mechanically interacts with the pressure trigger. The pressure trigger is configured to transmit the force of the plunger pin longitudinally along the axis of the needle assembly in a distal direction, such that the resilient member is activated to urge the needle tip safety guard distally along the needle and over the needle tip to its blocking position. The needle tip safety guard is passively actuated so that the user is not required to perform any operations outside of those employed using conventional hypodermic needles. In order to use the safety hypodermic needle assembly, it is not necessary for the user to learn additional procedures. The needle tip safety guard automatically blocks the needle tip so that the user, or those who dispose of the used needle, are not subjected to inadvertent needle sticks.

The safety hypodermic needle assembly provided in accordance with practice of the present invention may also be characterized as a safety hypodermic needle assembly which comprises a needle hub, a pressure fitting, a resilient member, and a pressure trigger and wherein the needle hub further comprises an internal needle assembly having a needle fixedly secured thereto and a stop member. The pressure fitting further comprises two elongated arms, two tapered ramps, a distal end having an opening, and a pair of cut-outs or a pair of male detents; and wherein the pair of male detents or the pair of cut-outs are configured to engage the stop member, wherein the pressure trigger is configured to interact with the tapered ramps, and wherein the elongated arms are configured to spread radially as a result of the interaction between the pressure trigger and the tapered ramps.

The safety hypodermic needle assembly discussed herein may be used with a standard syringe or a syringe with separate mechanisms for dispensing the medication and for launching the spring clip. Examples of the latter syringe includes a syringe for injecting fluids and having two distinct advancing mechanisms comprising a barrel having a proximal end and a distal end, a syringe tip located on the distal end, and an enclosed end having a bore for passing fluids. The syringe also includes a plunger having a proximal end and a distal end, an extension pin extending from the distal end, and a plunger tip disposed on the distal end and having the extension pin passing therethrough; wherein plunger is configured to move from a first position to a second position in which the plunger tip contacts the enclosed end of the barrel by application of a first distally force; and wherein the plunger is configured to move to a third position relative to the plunger tip by application of a second distally force, which is greater than the first distally force.

BRIEF DESCRIPTION OF THE DRAWINGS

These and other features and advantages of the present invention will become appreciated as the same becomes better understood with reference to the specification, claims and drawings wherein:

FIG. 1a is a semi-schematic cross-sectional top view of an unactivated hypodermic needle assembly according to one embodiment of the present invention not yet attached to a syringe;

FIG. 1b is a semi-schematic cross-sectional top view of the hypodermic needle assembly of FIG. 1a shown in its activated state and attached to a syringe;

FIG. 1c is a semi-schematic top view of the hypodermic needle assembly of FIG. 1a shown in its activated state;

FIG. 2a is a semi-schematic cross-sectional top view of an unactivated hypodermic needle assembly according to a second embodiment of the present invention not yet attached to a syringe;

FIG. 2b is a semi-schematic cross-sectional top view of the hypodermic needle assembly of FIG. 2a shown in its activated state and attached to a syringe;

FIG. 2c is a semi-schematic top view of the hypodermic needle assembly of FIG. 2a shown in its activated state;

FIG. 3a is a semi-schematic cross-sectional top view of an unactivated hypodermic needle assembly according to a third embodiment of the present invention not yet attached to a syringe;

FIG. 3b is a semi-schematic cross-sectional top view of the hypodermic needle assembly of FIG. 3a shown in its activated state and attached to a syringe;

FIG. 3c is a semi-schematic top view of the hypodermic needle assembly of FIG. 3a shown in its activated state;

FIG. 6a is a semi-schematic cross-sectional top view of an unactivated hypodermic needle assembly according to a seventh embodiment of the present invention attached to a syringe;

FIG. 6b is a semi-schematic cross-sectional top view of the hypodermic needle assembly of FIG. 6a shown in its activated state and attached to a syringe;

FIG. 6c is a semi-schematic perspective view of the hypodermic needle assembly of FIG. 6a shown in its activated state and attached to a syringe;

FIG. 6d is a semi-schematic exploded perspective view of the hypodermic needle assembly and syringe of FIG. 6a;

FIG. 6e is a semi-schematic cross-sectional view of the hypodermic needle assembly taken along line 6e-6e of FIG. 6a;

FIG. 7a is a semi-schematic cross-sectional side view of an unactivated hypodermic needle assembly according to the eighth embodiment of the present invention attached to a syringe;

FIG. 7b is a semi-schematic cross-sectional end view of the unactivated hypodermic needle assembly of FIG. 7a taken at line A-A;

FIG. 7c is a semi-schematic cross-sectional side view of the hypodermic needle assembly of FIG. 7a shown in its activated state;

FIG. 7d is a semi-schematic perspective view of the hypodermic needle assembly of FIG. 7c;

FIG. 7e is a semi-schematic exploded perspective view of the hypodermic needle assembly of FIG. 7a;

FIG. 8a is a semi-schematic cross-sectional side view of an unactivated hypodermic needle assembly according to the ninth embodiment of the present invention;

FIG. 8b is a semi-schematic cross-sectional side view of the hypodermic needle assembly of FIG. 8a shown in its activated state and attached to a syringe;

FIG. 9a is a semi-schematic cross-sectional side view of an unactivated hypodermic needle assembly according to the tenth embodiment of the present invention;

FIG. 9b is a semi-schematic cross-sectional side view of the hypodermic needle assembly of FIG. 9a shown in its activated state and attached to a syringe;

FIG. 11a is a semi-schematic cross-sectional side view of an unactivated hypodermic needle assembly according to the twelfth embodiment of the present invention;

FIG. 11b is a semi-schematic cross-sectional side view of the unactivated hypodermic needle assembly of FIG. 11a from a different perspective;

FIG. 12a is a semi-schematic cross-sectional side view of an unactivated hypodermic needle assembly according to the thirteenth embodiment of the present invention;

FIG. 12b is a semi-schematic cross-sectional side view of the unactivated hypodermic needle assembly of FIG. 12a from a different perspective;

FIG. 13a is a semi-schematic cross-sectional side view of an unactivated hypodermic needle assembly according to the fourteenth embodiment of the present invention, which includes a proximal hub section and a distal hub section;

FIG. 13b is a semi-schematic cross-sectional side view of the unactivated hypodermic needle assembly of FIG. 13a from a different perspective;

FIG. 13c is a semi-schematic cross-sectional end view of the unactivated hypodermic needle assembly of FIG. 13a taken at line C-C;

FIG. 13d is a semi-schematic cross-sectional end view of the unactivated hypodermic needle assembly of FIG. 13a taken at line D-D;

FIG. 14a is a semi-schematic cross-sectional side view of an unactivated hypodermic needle assembly according to the fifteenth embodiment of the present invention, which includes a pressure fitting;

FIG. 14b is a semi-schematic cross-sectional end view of the unactivated hypodermic needle assembly of FIG. 14a taken at line E-E;

FIG. 14c is semi-schematic cross-sectional side view of the hypodermic needle assembly of FIG. 14a shown in its activated state and attached to a syringe;

FIG. 15a is a combination semi-schematic cross-sectional side view and elevation view of a syringe with a trigger gap provided in accordance with practice of the present invention;

FIG. 15b is a combination semi-schematic cross-sectional side view and elevation view of the syringe of FIG. 15a with the trigger gap taken up by the plunger;

FIG. 15c is a semi-schematic cross-sectional side view of the syringe of FIG. 15a mounted to an unactivated hypodermic needle assembly, which is in accordance with the sixteenth embodiment of the present invention;

FIG. 15d semi-schematic cross-sectional side view of the syringe and hypodermic needle assembly of FIG. 15c in an activated position;

FIG. 19a is a semi-schematic cross-sectional side view of an unactivated hypodermic needle assembly according to the seventeenth embodiment of the present invention;

FIG. 19b is a semi-schematic cross-section end view of the unactivated hypodermic needle assembly of FIG. 19a taken at line F-F;

FIG. 19c is a semi-schematic cross-sectional side view of the hypodermic needle assembly of FIG. 19a shown in its activated state and attached to a syringe; and FIG. 19d is a perspective exploded view of the various components that make the hypodermic needle assembly of FIG. 19a.

DETAILED DESCRIPTION OF THE INVENTION

Figure 4A:
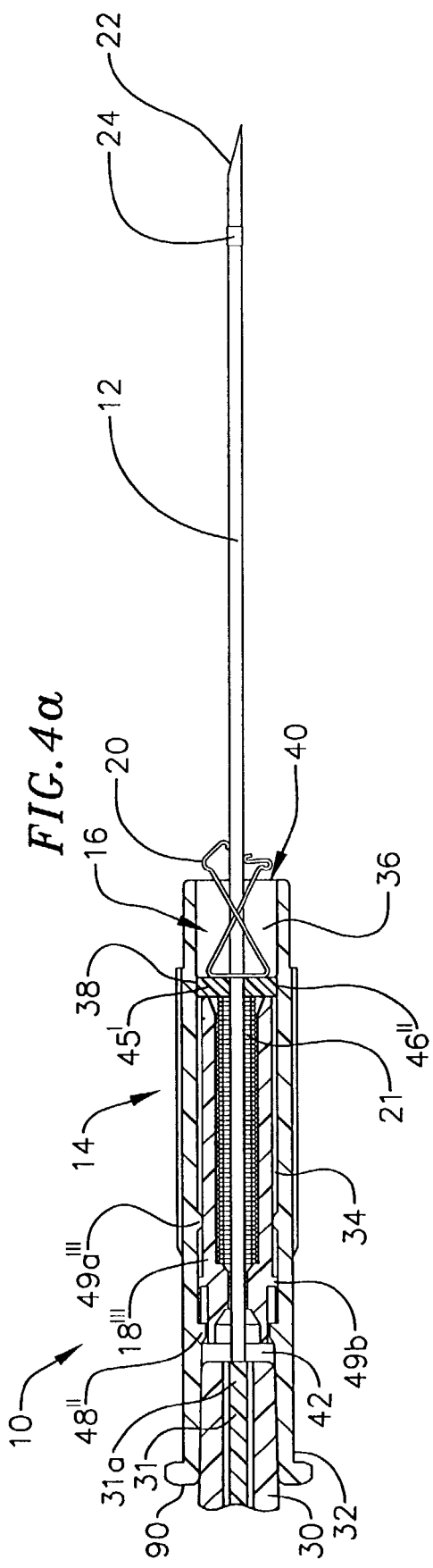
FIG. 4a is a semi-schematic cross-sectional top view of an unactivated hypodermic needle assembly according to a fourth embodiment of the present invention attached to a syringe.

The present invention is directed to a hypodermic needle assembly designed such that the movement of the needle shield into position to block the needle tip occurs as a direct consequence of the depression of a syringe plunger while injecting a medicant into a patient. The detailed description set forth below in connection with the appended drawings is intended as a description of the presently preferred embodiments of the hypodermic needle assembly provided in accordance with the present invention and is not intended to represent the only forms in which the present invention may be constructed or utilized. The description sets forth the features and the steps for constructing and using the hypodermic needle assembly of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

One illustrative embodiment of a hypodermic needle assembly according to the present invention is shown in FIGS. 1a-1c. The hypodermic needle assembly 10 shown therein comprises an introducing needle 12 arranged within a needle hub 14 in a conventional manner, and a spring-loaded safety clip needle tip guard assembly 16. The spring-loaded safety clip assembly 16 is mounted around the shaft of the needle 12 and, in an unactivated mode (as shown in FIG. 1a), is positioned within the needle hub 14. The safety clip assembly 16 comprises a pressure trigger 18, a spring clip 20, and a resilient member 21 fixedly connected therebetween. The spring clip 20 is slidably mounted to the needle 12 within the needle hub 14.

Any suitable needle 12 can be utilized with the present invention such that the needle 12 is constructed to slidingly cooperate with the spring clip 20. In the embodiment shown in FIGS. 1a-1c, the needle 12 includes a hollow shaft having a sharp tip 22 at the distal end and a proximal end which is arranged within the needle hub 14. The proximal end of the needle 12 communicates with a syringe tip engagement chamber 42 defined by the needle hub 14, which has an inlet sized to receive a syringe tip, and described below in greater detail.

Referring to FIGS. 1a-6a, the needle 12 has a proximal end adjoining the needle hub 14 and a distal end having a sharp tip 22 and comprises a cylindrical shaft having a longitudinal axis and defining an inner hollow passageway having an inner diameter. A needle stop 24 is disposed along the length of the needle shaft between the proximal and distal ends and, preferably, is proximate to the distal end of the needle. The diameter of the hollow passageway (not shown) extending through the needle is substantially constant. In one preferred embodiment, the needle also has the same outside diameter along its entire length. In this embodiment, the needle stop 24 is a crimped portion of the needle 12 formed by crimping the needle utilizing any conventional needle crimping tool. According to this preferred embodiment, the needle stop 24 comprises a crimped portion of the needle that extends out of the longitudinal axis defined by the rest of the needle shaft. Preferably, the needle stop 24 extends about 0.002 inches outside of the initial outside diameter of the needle shaft 12 prior to crimping. In one embodiment the crimp is formed with a cylindrical crimping tool with a radius of about 0.118 inches. Alternatively, the needle stop can include a change in contour such as an enlarged shaft section for providing a physical barrier for limiting the distal travel of the spring clip, as further discussed below.

Referring now to FIGS. 1b-4b, 5c, and 6b, the distance between the needle stop 24 and the needle tip 22 must be less than the total length of the spring clip 20 such that the needle tip 22 can be blocked thereby. In a preferred embodiment, the distance between the needle stop 24 and the needle tip is such that the needle stop engages a restraining hole or opening 26 in an end wall 28 of the spring clip 20 just after the spring clip engages to block the needle tip. Because the restraining opening 26 in the end wall 28 of the spring clip 20 is unable to move past the needle stop 24, the spring clip is prevented from being pulled from or otherwise being moved off the distal end of the needle 12. Thus, when the spring clip is activated such that it slides distally along the length of the needle 12 to the tip 22, the needle tip is blocked by the spring clip and the portion of the needle stop 24 extending out of the longitudinal axis of the needle 12 interacts with the restraining hole 26 in the end wall 28 to prevent the spring clip from being fully withdrawn from the needle 12, thus preventing the needle tip from being exposed.

Although one embodiment of a needle 12 is described above, any suitable needle can be utilized such that the needle can be easily inserted into and withdrawn from a patient, the spring clip 20 can readily slide along the needle, and the spring clip cannot be fully withdrawn from the needle once the spring clip is engaged on the needle tip.

Although a crimped needle stop 24, as described above, is preferable because of the simple and inexpensive nature of producing a crimp in a needle, the needle stop 24 can be formed in any shape suitable to prevent the spring clip 20 from being completely withdrawn from the needle tip 22. In one alternative embodiment, the needle stop 24 is provided as an enlarged diameter portion of the needle where the diameter is slightly larger than the diameter of the restraining opening 26 through the end wall 28 of the spring clip. Thus, when the spring clip is launched along the length of the needle by the resilient member 21, which in a preferred embodiment is a spring, and the needle tip 22 is blocked by the spring clip, the diameter of the needle stop 24 prevents the spring clip from being completely withdrawn from the needle tip 22, thereby preventing the needle tip from being exposed. Such an enlarged-diameter needle stop can be formed by any suitable technique, such as, for example, by electroetching material from the needle upstream and downstream from the needle stop area to reduce the diameter of the remainder of the needle. Grinding is another alternative for shaping the needle 12 to the desired configuration. Either technique provides a shaped needle 12 of integral construction, which is preferred. Other possible techniques for providing the needle stop include plating the area selected for enlargement, or insert molding a band of polymeric material around the needle or welding or adhesive bonding a sleeve onto the needle.

Any needle hub 14 design can be utilized in the safety hypodermic needle assembly of the present invention, such that a needle 12 and safety clip assembly 16 are arranged therein and, if separate, a syringe 30 comprising a plunger 31 incorporating an extension pin 31a which extends into the syringe tip and, in some embodiments, extends through and out from the syringe tip can be adjoined thereto. The needle hub 14 employed in accordance with the embodiments of the invention shown in FIGS. 1-6 comprises an integrally molded body 32 defining an axial cylindrical inner needle passageway 34 having dimensions designed to accept the needle 12 therein and to allow the pressure trigger 18 and resilient member 21 to be slidably movable therein. (In some embodiments, the reference numbers are followed by one or more superscript primes (') to differentiate between common elements which have different structural features.) With regard to the fixation of the needle 12 and pressure trigger 18 within the passageway 34, the needle hub 14 should meet the "pull strength standard" such that if the needle 12 should strike bone or solid mass during injection, neither the needle 12 nor pressure trigger 18 will be pushed proximally out from the back of the needle hub 14. The needle passageway 34 is also arranged and designed such that the slidable pressure trigger 18 cannot be moved distally beyond a certain point, nor can the needle 12 be dislodged from the needle hub 14 in a distal direction. Table 1, below lists international standards for needle hub "push" and "pull" strengths for needles having a variety of outer diameters.

TABLE 1

International Standard for Needle Hub Push and Pull Strengths

| Needle Outer Diameter (mm) | Connection Strength (N) |
|---|---|
| 0.3 | 22 |
| 0.33 | 22 |
| 0.36 | 22 |
| 0.4 | 22 |
| 0.45 | 22 |
| 0.5 | 22 |
| 0.55 | 34 |
| 0.6 | 34 |
| 0.7 | 40 |
| 0.8 | 44 |
| 0.9 | 54 |
| 1.1 | 69 |
| 1.2 | 69 |

A cylindrical spring clip cavity 36 coaxial with the needle passageway 34 and having a support wall 38 in its proximal end and a spring clip opening 40 in its distal end is provided in the distal end of the needle hub 14. The proximal end of the needle hub is defined by the syringe tip engagement chamber 42 which is slightly conical in shape and which, in some embodiments, is a female luer fitting or luer taper. The syringe tip engagement chamber is coaxial with the needle passageway 34 and has an opening 44 provided therein to accommodate the tip of a syringe, which generally has a male luer configuration, in liquid-tight engagement. The spring clip 20, when unactivated, is positioned within the spring clip cavity 36. A pressure fitting 45 is located at the proximal end of the spring clip and is in mechanical communication with the support wall 38 of the spring clip cavity. The pressure trigger 18 and resilient member 21 are positioned within the needle passageway 34, such that the proximal end of the needle clip assembly 16 and the needle 12 are in mechanical and fluid communication, respectively, with the distal end of the syringe tip engagement chamber 42. As shown in FIGS. 1a-6a, the above elements are arranged such that the needle 12 passes at least partially through and out from the distal end portion of the pressure trigger 18, through the resilient member 21 in the needle passageway 34, through the spring clip 20 in the spring clip cavity 36, and out from the needle hub opening 40.

The needle hub 14, comprising the needle passageway 34, spring clip cavity 36, and syringe tip engagement chamber 42, can have any suitable design such that the needle 12, needle tip guard 16, pressure trigger 18 and syringe 30 can be functionally disposed therein. In the embodiment shown in FIGS. 1a-1c, for example, the distal needle hub exit opening 40 of the spring clip cavity is in coaxial arrangement with the needle passageway 34, and has a sufficient diameter to allow the spring clip 20 to be ejected distally from the needle hub 14 along the needle shaft 12. In this embodiment, the needle passageway 34 has an opening 46 in the spring clip cavity end wall 38, and the pressure fitting 45, which is ring-shaped and located at the proximal end of the spring clip and mounted around the needle, is frictionally engaged with the opening 46. The needle passageway 34 also has a pressure trigger engaging opening 48 arranged in the distal end portion of the syringe tip engagement chamber 42, such that a pressure trigger fitting portion 47 of the pressure trigger 18 is frictionally engaged therewith, and such that the pressure trigger can engage a pin 31a which is provided as an extension of the syringe plunger 31. In this embodiment, the needle passageway 34 also comprises a pressure trigger stop 49 comprising a metal sleeve. The sleeve incorporates a pressure trigger stop indented portion 49a formed therein which is arranged coaxially within the needle passageway 34 such that the pressure trigger 18 is prevented from sliding distally past the pressure trigger stop indention 49a. In addition, the pressure trigger engaging opening 48 at the proximal end of the needle passageway 34 is tapered such that the slidable pressure trigger 18 cannot be moved in the proximal direction. In this embodiment, the resilient member 21 is a coil spring disposed coaxially around the needle 12 within the needle passageway 34. The spring is engaged at its distal end in a circumferential recess in the pressure fitting 45 which, in turn, is in contact with the spring clip end wall 28 and is engaged at its proximal end with the pressure trigger 18, such that the spring mechanically interacts with both the spring clip and the pressure trigger. While in this embodiment, the spring is not fixedly attached to the pressure trigger 18, if desired, the spring may be fixedly attached thereto. The needle 12 is fixedly attached to the pressure trigger, such that when the pressure trigger is moved distally at the urging of the extension pin 31a of the syringe plunger 31, the needle also moves in the distal direction.

In the embodiment of the needle assembly shown in FIGS. 2a-2c, the needle passageway 34, spring clip cavity 36, and syringe tip engagement chamber 42 are designed generally as described for FIGS. 1a-1c above, except that the needle passageway 34 has dimensions sufficient to allow the insertion of a pressure trigger 18' that extends along the entire length of the needle passageway 34. The proximal end of the pressure trigger 18' interacts with the extension pin portion 31a of the plunger 31 of the syringe 30 and the distal end portion of the pressure trigger 18' interacts directly with the pressure fitting 45 disposed in the distal end of the needle passageway 34 adjacent to the proximal end of the spring clip cavity 36. In such an embodiment, the resilient member 21 is a coil spring disposed coaxially around the needle 12 within the cylindrical body of the pressure trigger 18'. As was the case with the FIG. 1 embodiment, the spring is engaged at its distal end in a circumferential recess in the pressure fitting 45 which, in turn, is in contact with the spring clip end wall 28. In this embodiment, the needle passageway 34 also includes a pressure trigger stop 49' comprising a metal sleeve having an indented portion 49a' therein arranged coaxially within the needle passageway 34 and designed to interact with an enlarged portion 18a' of the pressure trigger such that the pressure trigger 18' is prevented from sliding distally past the pressure trigger stop 49a'. The pressure trigger engaging opening 48 at the proximal end of the needle passageway 34 is also tapered, as shown, such that the slidable pressure trigger 18' cannot be moved in the proximal direction. In this embodiment, as in the embodiment shown in FIGS. 1a-1c, the needle 12 is fixedly attached to the slidable pressure trigger 18' such that the needle 12 moves therewith when the pressure trigger 18' is urged distally by the action of the syringe plunger 31.

Although metal sleeves 49 and 49' are shown forming the pressure trigger stop 49a and 49a' in the two exemplary embodiments shown in FIGS. 1a-1c and 2a-2c respectively, in an alternative embodiment the metal sleeve is omitted and the pressure trigger stop 49a is provided by a ring integrally formed circumferentially around the wall of the needle passageway 34 which extends into the needle passage, reducing its diameter at that location.

In the exemplary embodiment of the needle assembly shown in FIGS. 3a-3c, the spring clip assembly 16 further comprises a spring clip housing 50. In this embodiment, the spring clip cavity 36 has dimensions such that the housing 50 can be inserted into the cavity and then ejected distally therefrom along the needle shaft 12. In this embodiment, as is best shown in FIGS. 3a and 3b, the needle passageway 34 has a needle clip housing engaging opening 46' formed in the spring clip cavity end wall 38. A pressure fitting 51, which is integrally formed on the proximal end of the housing 50, is frictionally engaged in the opening 46'. A frangible seal 48', which is formed around an external flange 47' disposed around the proximal end of the pressure trigger 18", is annularly engaged with the inside surface of the wall of the syringe tip engagement chamber 42. In this embodiment, as with the embodiment shown and described in FIGS. 1 and 2 above, the needle passageway 34 comprises a pressure trigger stop 49a" comprising a ring formed integrally in the wall of the needle passageway 34 and arranged such that the pressure trigger 18" is prevented from sliding distally past the pressure trigger stop 49a". If desired, in an alternative embodiment of the spring assembly of the present invention, a portion of the proximal end of the needle passageway 34 can be tapered such that the slidable pressure trigger 18" cannot be moved in the proximal direction due to an interference between the taper and the external flange 47'.

In the embodiment shown in FIGS. 3a and 3b, the pressure trigger 18" comprises a cylindrical body within which the needle 12 is fixedly attached and the resilient member 21 is disposed. The resilient member 21 is a coil spring and is disposed coaxially around the needle 12 within the body of the pressure trigger 18", which itself is disposed within the needle passageway 34. In the unactivated state (shown in FIG. 3a), the external flange 47' extends outwardly from the pressure trigger 18" and engages the inner wall of needle passageway 34 at the frangible seal 48' formed around the inner wall. When engaged by the extension pin 31a of the plunger 31 and the plunger is pushed in the distal direction, the frangible seal 48' is broken and the pressure trigger 18" can slide distally in the needle passageway (FIG. 3b). The needle 12 is fixedly attached at its proximal end to the pressure trigger 18", and the spring 21 extends between the pressure trigger 18" and the housing 50, such that the spring mechanically interacts with both the spring clip 20 and the pressure trigger 18". As in the embodiment shown in FIGS. 2a-2c, the pressure trigger 18" in this embodiment is of sufficient length such that the proximal end of the pressure trigger 18" mechanically interacts with the extension pin 31a of the syringe plunger 31, and the distal end of the pressure trigger 18" mechanically interacts directly with the proximal end of the housing 50. In this embodiment, the above elements are arranged such that the needle 12 passes through the pressure trigger 18", and the spring 21 in the needle passageway 34, through the housing 50 and spring clip 20 in the spring clip cavity 36, and out from the needle hub opening 40.

Figure 4B:
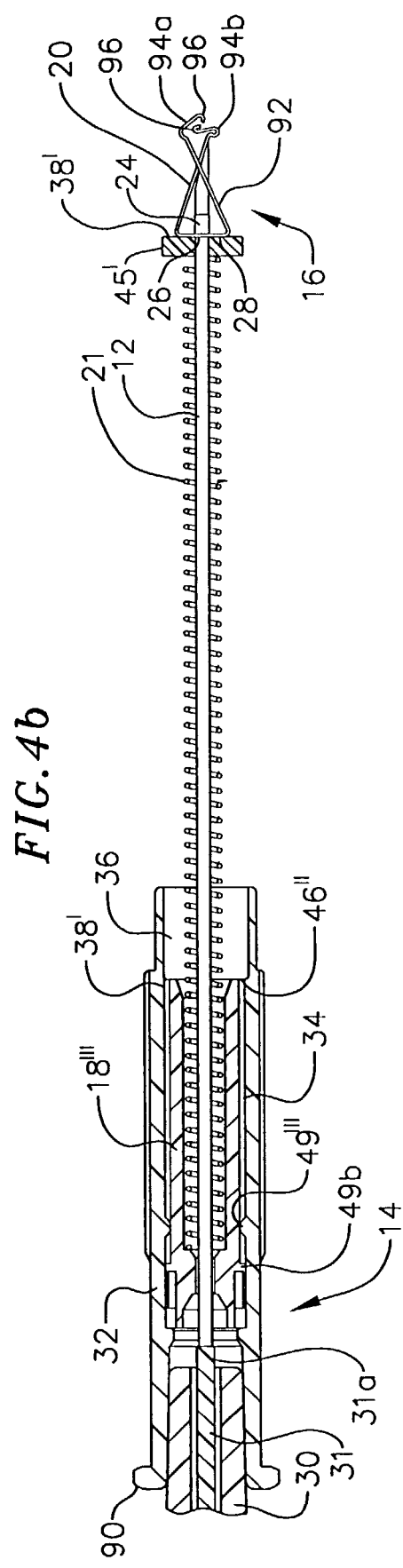
FIG. 4b is a semi-schematic cross-sectional top view of the hypodermic needle assembly of FIG. 4a shown in its activated state and attached to a syringe.
Figure 4C:
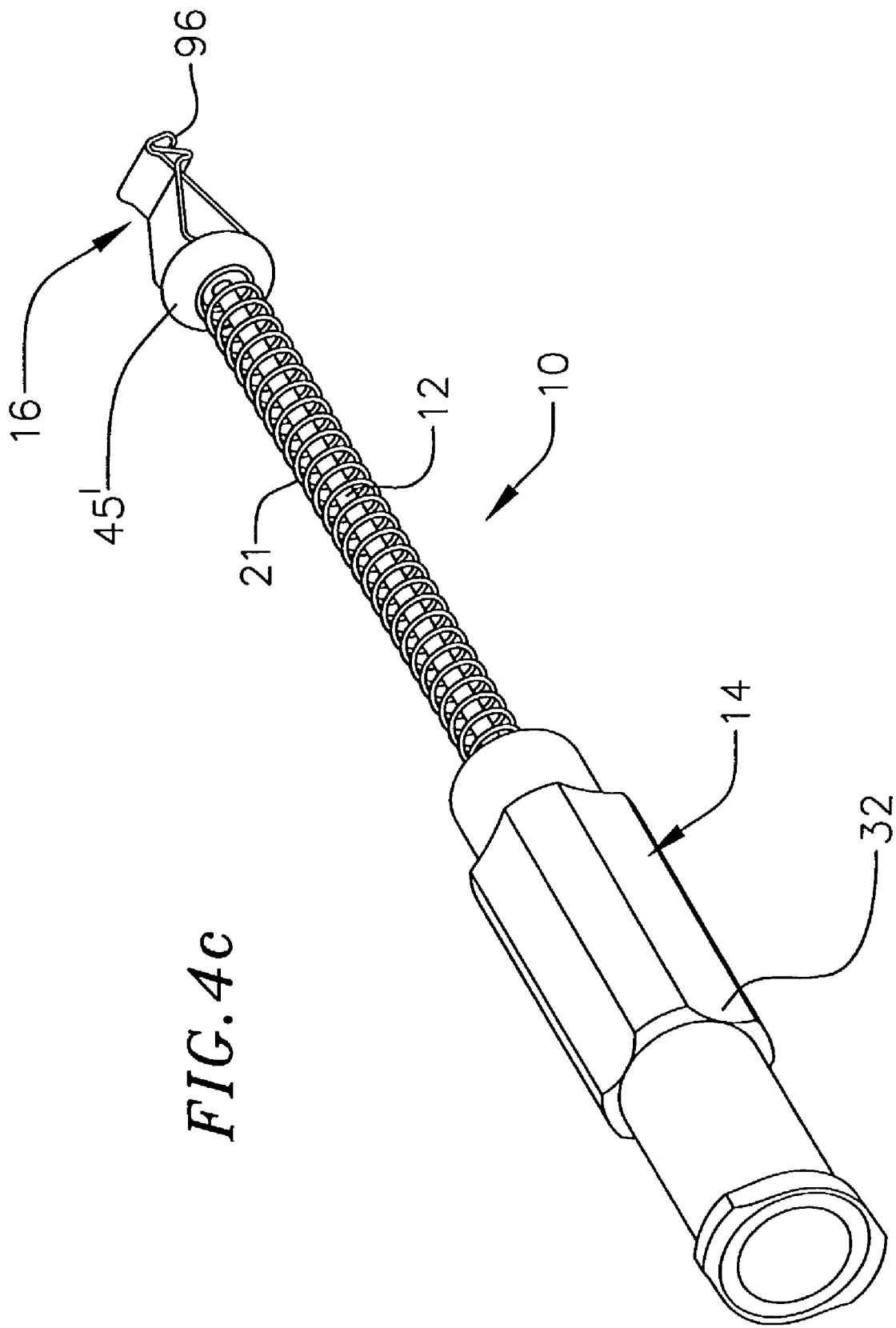
FIG. 4c is a semi-schematic perspective view of the hypodermic needle assembly of FIG. 4a shown in its activated state.

In the exemplary embodiment of the needle assembly shown in FIGS. 4a-4c, the spring clip pressure fitting 45' has a relatively wider diameter so as to effectively reduce the support wall 38' of the needle tip guard cavity 36 to a minimum. In this embodiment, the pressure trigger 18''' further comprises an annular stop engaging flange or skirt 49b which extends around the proximal end of the pressure trigger with a diameter slightly larger than the diameter of the cylindrical pressure trigger body 18'''. The needle passageway 34 also comprises a pressure trigger stop 49a''' comprising a ring formed circumferentially around the wall defining the needle passageway 34 thereby reducing the diameter of the needle passageway at that location. The pressure trigger 18''' is prevented from sliding distally past the pressure trigger stop 49a''' by the engagement of the stop 49a''' with the flange 49b. In addition, a ring 48" extending around the proximal end of the inner surface of the needle passageway 34 is configured to engage the stop engaging flange 49b such that the slidable pressure trigger 18''' cannot be moved past the ring 48" in the proximal direction.

In this embodiment, the pressure trigger 18''' comprises a slidable cylindrical body within which the needle 12 is fixedly attached and the resilient member 21 is disposed. The resilient member 21 is a coil spring and is disposed coaxially around the needle 12 within the body of the pressure trigger 18''', which itself is disposed within the needle passageway 34. The needle is fixedly attached at its proximal end to the pressure trigger 18'''. In this embodiment, the spring is not fixedly attached to the pressure fitting but is in removable contact therewith and mechanically interacts with both the spring clip 20 and the pressure trigger 18'''. The needle 12 extends proximally from the pressure trigger 18''' such that the proximal end of the needle 12 mechanically interacts with the extension pin 31a of the plunger 31 of the syringe 30, and the distal end of the pressure trigger 18''' mechanically interacts directly with the pressure fitting 45'. In the illustrated embodiment, the needle 12 passes through the pressure trigger 18''' and spring 21 of the needle tip guard assembly 16 in the needle passageway 34, through the pressure fitting 45' and spring clip 20 in the spring clip cavity 36, and out from the needle hub opening 40. In this embodiment, the clip 20 extends distally from the cavity 36 when the needle assembly is in its unactivated condition.

Figure 5A:
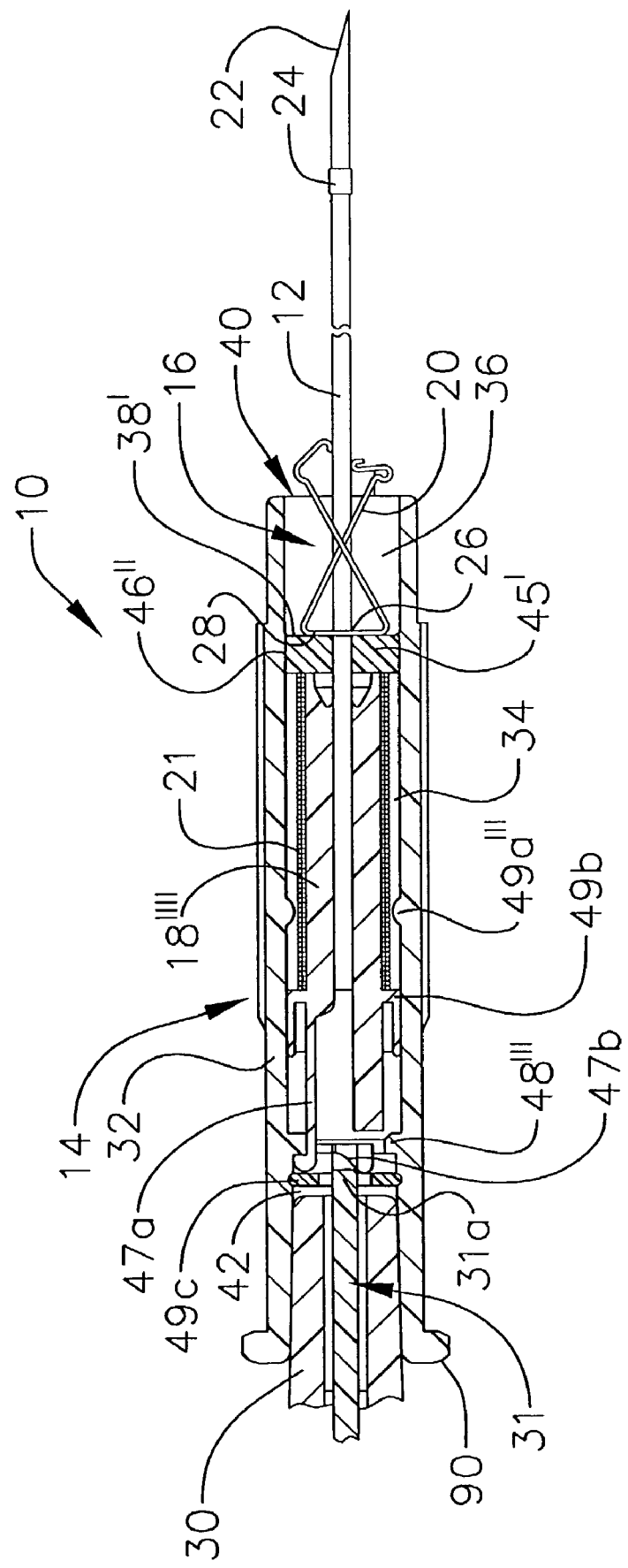
FIG. 5a is a semi-schematic cross-sectional top view of an unactivated hypodermic needle assembly according to a fifth embodiment of the present invention attached to a syringe.

In the exemplary embodiment shown in FIG. 5a, the needle clip assembly 16 and the needle hub 14 are generally as described above with reference to FIGS. 4a-4c, except that the syringe tip engagement chamber 42 further comprises a proximal needle stop 49c and the pressure trigger 18''' further comprises at least one flexible hook 47a. The flexible hook 47a is configured to engage the proximal needle stop 49c to thereby prevent the pressure trigger from sliding proximally out of the needle hub 14 when it is subjected to a proximally directed force; such as, for example, when the needle impacts on a bone. The proximal needle stop 49c may comprise any suitable engaging flange, such as, for example, a snap ring disposed within an annular groove formed in the wall of the syringe tip engagement chamber 42. In this embodiment, the engaging opening 48''' comprises an engaging surface specifically configured to catch and hold the flexible hook 47a to releasably hold the pressure trigger 18'''' against inadvertent distal movement prior to activation by the syringe extension pin 31a. The hook 47a is configured such that, during activation, the syringe extension pin 31a interacts with a platform 47b which extends from the bottom portion of the hook to move the hook inwardly, thereby disengaging the hook from the opening 48''' and allowing distal movement of the pressure trigger 18''''. In such an embodiment, once the hook 47a on the pressure trigger 18'''' is moved distally past the engaging opening 48''', the hook 47a springs outwardly toward the wall of the needle passageway 34. When in this configuration (shown in FIG. 5c), any proximal movement of the pressure trigger 18'''' will push the hook 47a against the annular distal wall of the engaging opening 48''' to thereby block further proximal movement. As in the embodiments shown and described in FIGS. 1-4 above, the needle 12 is fixedly mounted within the slidable pressure trigger 18'''' such that the needle moves with the pressure trigger when the pressure trigger is moved distally by the extension pin 31a of the syringe plunger 31.

Figure 5B:
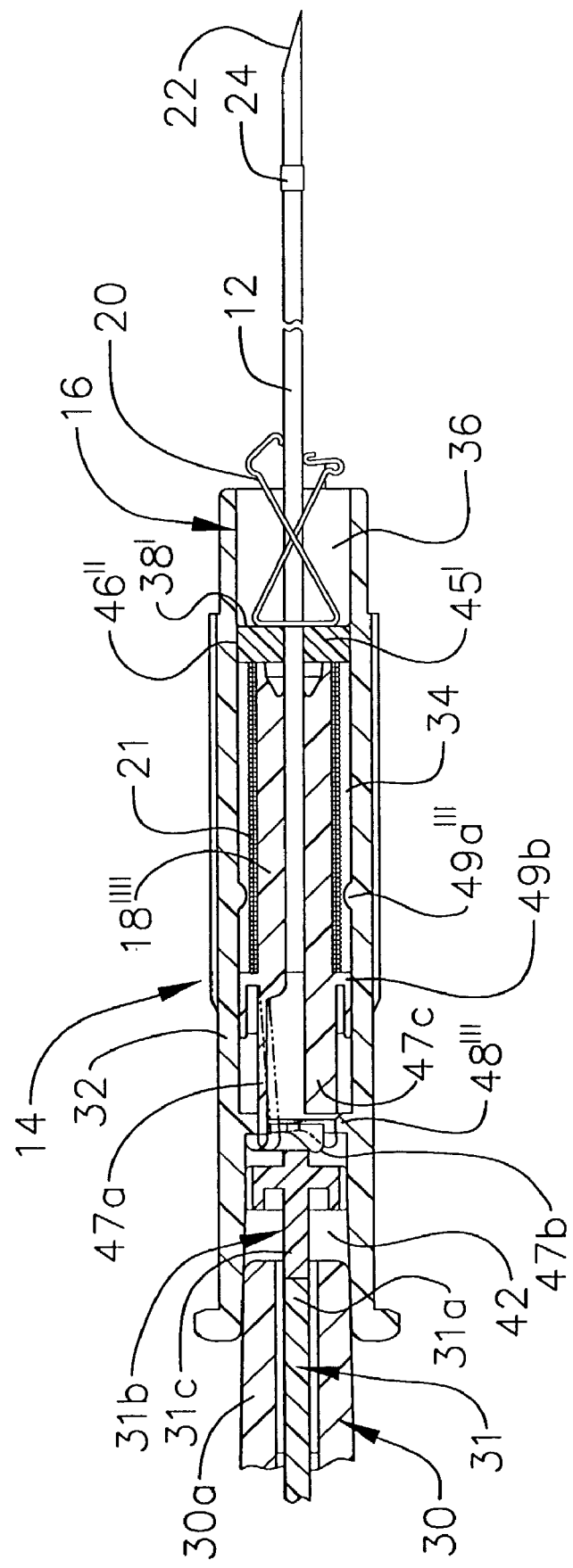
FIG. 5b is a semi-schematic cross-sectional top view of an unactivated hypodermic needle assembly according to the sixth embodiment of the present invention attached to the syringe.
Figure 5C:
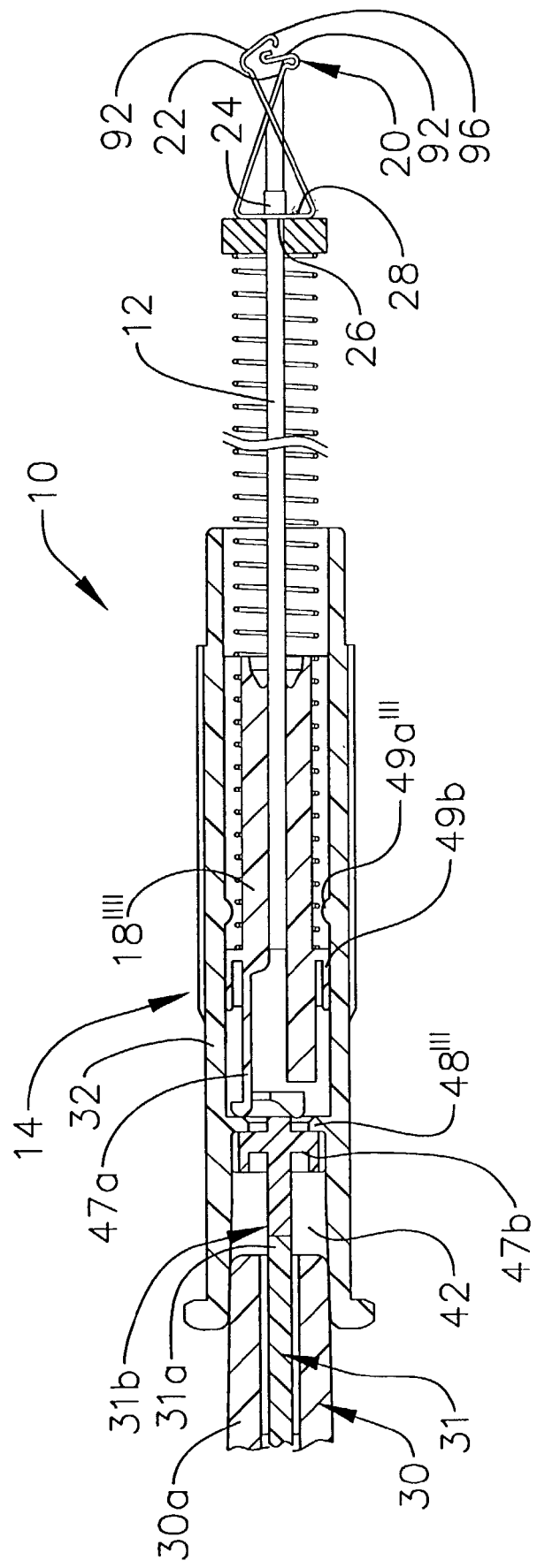
FIG. 5c is a semi-schematic top view of the hypodermic needle assembly of FIG. 5b shown in its activated state and attached to a syringe.

In the exemplary embodiment shown in FIGS. 5b and 5c, the needle tip guard assembly 16 and the needle hub 14 are generally as described above with reference to FIGS. 4a-4c and 5a, except that the assembly further comprises an intermediate pusher assembly 31b disposed within the syringe tip engagement chamber 42 between the syringe 30 and the pressure trigger 18''''. In this embodiment the pressure trigger 18'''' comprises at least one flexible hook 47a and further has an enlarged proximal end 47c. The intermediate pusher assembly 31b is configured to transmit the force of the extension pin 31a of the syringe plunger 31 to the pressure trigger 18''''. The enlarged proximal end 47c is configured to engage the opening 48''' such that the pressure trigger 18'''' is prevented from sliding proximally out of the needle hub 14 when subjected to a proximally directed force, such as, for example a needle impact on a bone. The intermediate pusher assembly 31b has an elongated pin or arm 31c on its proximal end, which is designed and arranged to extend into the tip 30a of the syringe 30 to engage the extension pin 31a. Thus, in this embodiment, the extension pin 31a needs to extend only to essentially the opening of the syringe tip and does not need to extend therefrom as is shown in the previously described embodiments.

In this embodiment, the engaging opening 48''' further comprises a proximal facing annular engaging surface configured to engage the flexible hook 47a which, in turn, releasably holds the pressure trigger 18'''' to prevent inadvertent distal movement of the pressure trigger prior to activation by the pusher assembly 31b. As best shown in phantom in FIG. 5b, the hook 47a is configured such that during activation, the intermediate pusher assembly 31b interacts with the platform 47b to move the hook 47a inwardly to disengage the hook from the engaging opening 48''' to thereby allow distal movement of the pressure trigger 18''''. As is best seen in FIG. 5c, after the device is activated and the hook 47a is moved distally past the engaging opening 48''', the hook springs outwardly toward the wall of the needle passage 34. When the syringe assembly is in this activated state, proximal movement of the pressure trigger 18'''' will push the hook 47a against the distal facing annular wall of the engaging opening 48''', thereby stopping further proximal movement of the pressure trigger. As in the embodiments shown and described in FIGS. 1-4 above, the needle 12 is fixedly mounted within the slidable pressure trigger 18'''' such that the needle 12 moves with the pressure trigger when the pressure trigger is moved distally by the intermediate pusher assembly 31b.

Turning to FIGS. 6a-6e, yet another embodiment of a safety hypodermic assembly provided in accordance with the practice of the present invention is shown. In this embodiment, the needle 12 is fixedly attached to the needle hub 14' by means of an inner needle assembly 52. The needle assembly 52 is integral with the needle hub 14' and is arranged in the needle passageway 34 such that the needle 12 does not move with respect to the needle hub 14' when the needle clip assembly 16 is activated. In this embodiment, the needle 12 is fixedly attached to the inner needle mounting assembly 52 by a glue or adhesive plug 56 which is formed by injecting glue into the mounting assembly 52 through an opening 58 (shown in FIG. 6d) disposed through the outer surface of the needle hub 14'. As best shown in FIG. 6b, two passages 60a and 60b extend along the sides of the inner needle mounting assembly 52, such that a pressure fitting 45'' can extend therethrough and mechanically engage the pressure trigger 18''''.

As shown in FIGS. 6c and 6d, the pressure fitting 45' of this embodiment comprises an elongated body 66 having a bifurcated proximal end forming two elongated arms 68a and 68b and a cylindrical distal end 70 defining a cavity 72. The cavity 72 is configured to enclose the distal end of the inner needle assembly 52 and the resilient member 21 which (as shown in FIG. 6a), is disposed about the distal end of the inner needle assembly 52. The arms 68a and 68b are designed and arranged such that they extend through the passages 60a and 60b (FIG. 6b) in the needle hub 14' and mechanically engage the distal end of the pressure trigger 18'''' when the needle assembly is in its unactivated condition. In the embodiment shown in FIGS. 6a-6e, the resilient member 21 is a coil spring and is disposed coaxially around the needle assembly 52 within the body of the pressure fitting 45'', which itself is disposed within the needle passageway 34. As in the previous embodiments, the spring 21 is in contact with and may be fixedly attached at its distal end to the pressure fitting 45'' such that it mechanically interacts with the spring clip 20. In the preferred embodiment, the distal end of the pressure fitting 45'' comprises most of the proximal wall of the spring clip cavity 36. In such an embodiment, as is best shown in FIGS. 6a and 6b, the needle passageway 34 has an enlarged opening 46''' which engages the enlarged distal end of the pressure fitting 45''. As shown best in FIGS. 6a and 6b, in this embodiment the pressure fitting 45'' is designed such that when the resilient member 21 pressingly launches the pressure fitting 45'', after the release of the pressure fitting 45'' from the engaging opening 46''', the entire pressure fitting is launched along with the spring clip distally along the needle 12 and covers a substantial portion of the needle 12.

Turning to FIGS. 6a and 6d, the pressure trigger 18'''' comprises a substantially cylindrical body 74 having a proximal cylinder wall 76 defining a proximal cavity 78 and a distal cylindrical wall 80 defining a distal cavity 82. In this embodiment, the proximal end of the pressure trigger 18'''' comprises a plunger engaging portion or arm 86 extending along the central axis from within the proximal cavity 78 of the pressure trigger. The arm is in the shape of a pin and is sufficiently elongated that it extends some distance into the opening of the syringe tip. Thus, to contact the end of the pressure trigger 18'''', the extension pin 31a of the syringe needs to extend only part way to the opening of the syringe tip and does not need to extend therefrom.

As shown in FIGS. 6a, 6b, and 6e, the inner needle assembly 52 is formed integrally with the needle hub 14' and is arranged such that the distal cylindrical wall 80 of the pressure trigger 18'''' engages the needle assembly 52 and thereby provides a fluid path seal. Turning to FIG. 6e, an enlarged section 52a of the needle assembly 52 extends completely across the width of the needle hub 14' and is integrally formed therewith. In this embodiment, the distal cylindrical wall 80 of the pressure trigger 18'''' can only move distally to the stop 81 of the needle assembly 52, thus limiting its distal movement. The step between the needle passageway 34 and the engaging opening 46''' engages the enlarged distal end of the pressure fitting 45'' to thereby prevent the pressure fitting from being moved in the proximal direction.

In the embodiment shown in FIGS. 6a-6e, the pressure trigger 18'''' is also designed to provide fluid communication between the syringe tip engagement chamber 42 and the proximal end of the needle 12. To provide such fluid communication, an opening 88 is provided in the proximal cavity 78 of the pressure trigger 18'''' which defines a fluid passageway between the proximal cavity 78 and the distal cavity 82. The distal cavity 82 is designed and arranged such that the proximal end of the inner needle assembly 52 having the proximal end of the needle 12 disposed therein, extends inside the distal cavity 82. The distal wall 80 of the pressure trigger 18'''' is in turn sealingly engaged around the proximal end of the inner needle assembly 52, such that a tight seal is formed therebetween. Accordingly, fluid introduced into the syringe tip engagement chamber 42 flows into the proximal cavity 78 through the opening 88 into the distal cavity 82 and thereby into the needle 12.

Although one specific arrangement of the embodiment of FIG. 6 is described above, any suitable design may be utilized such that the following design elements are incorporated therein: 1) the needle 12 is fixedly attached to the outer needle hub 14' such that the needle does not move when the needle clip assembly 16 is activated; 2) the pressure fitting 45'' comprises an elongated body within which the needle and the resilient member 21 are disposed; 3) the pressure trigger 18'''' has an arm or pin on its proximal end of sufficient length such that the proximal end mechanically interacts with the extension pin 31a of the plunger 31 of the syringe 30 and the pressure trigger distal end mechanically interacts with the pressure fitting 45''; and 4) the above elements are arranged such that the needle 12 passes out from the distal end of the pressure trigger 18'''', through the inner needle hub assembly 52 and the resilient member 21 in the needle passageway 34, through the pressure fitting 45'' and spring clip 20 in the spring clip cavity 36, and out from the distal needle hub opening 40.

Turning to FIGS. 7a-7e, another alternative embodiment of a safety hypodermic assembly 14' provided in accordance with practice of the present invention is shown. This embodiment is similar to the embodiment shown in FIGS. 6a-6e in that they both utilize an inner needle assembly 52, 52' and they both firmly hold the needle 12 stationary as the needle clip assembly 16 is activated. However, unlike the earlier embodiments, in the present embodiment a pressure fitting 100 directly engages the inner needle assembly 52' at the stop member 81 by a pair of male detents 102 located on each of the elongated arms 68a', 68b'. The male detents 102 provide the gripping pressure necessary to keep the resilient member 21 compressed in the unactivated position (FIG. 7a). To activate the needle clip assembly 16, the male detents 102 must disengage from the stop member 81 in order to launch the clip assembly, as is further discussed below.

The interaction between the male detents 102 and the stop 81 can best be understood with reference to FIGS. 7a, 7c, and 7e. In an unactivated position (FIG. 7a), the pressure fitting 100 is positioned inside the needle passageway 34. To facilitate the placement of the pressure fitting 100 within the passageway 34, the shroud 106 is configured with a pair of slits 108 (FIGS. 7d and 7e). The slits 108 provide the necessary space or clearance for the pressure fitting 100, which has a larger cross-sectional area than the shroud 106, to pass through the shroud and into and out from the passageway.

Referring particularly to FIG. 7a, the male detents 102 on the elongated arms 68a', 68b', which extend proximally into the needle passage way 34, engage the stop 81. The pair of elongated arms 68a', 68b' are resiliently inwardly biased in the direction of the longitudinal axis of the needle 12 to effect the engagement between the male detents and the stop 81. On the proximal end of each of the elongated arms 68a', 68b', there is a tapered ramp 110 (FIGS. 7c and 7e) for interacting with the pressure trigger 112. The pressure trigger 112 and the tapered ramps 110 on each of the elongated arms interact when the pressure trigger moves distally to exert a force against the tapered ramps. This exertion by the pressure trigger 112 against the surface of the tapered ramps produces a pair of component forces. As readily understood by a person of ordinary skill in the art, one of the component forces causes the ramps 110 to move apart which in turn causes the arms 68a', 68b' to spread radially outward, away from the longitudinal axis of the needle. At the point where the male detents 102 are disengaged from the stop 81 due to the arms spreading radially outward, the compressed resilient member 21 uncoils and launches the pressure fitting 100 distally relative to the needle shaft 12 until the restraining opening 26 located on the spring clip 20 (FIG. 7e) abuts the needle stop 24 as previously discussed. The spring clip 20 then blocks the needle tip 22 so that the user or those who dispose of the needle are not subjected to accidental needle stick.

The pressure trigger 112 (FIGS. 7a, 7c, and 7e) utilized in the present embodiment comprises a cylindrical body 74 having an inlet opening 88, and an outlet opening 114, which together define an interior passageway for fluid communication between the syringe 30 and the proximal end of the needle 12. The pressure trigger 112 is flanked at the distal end by a generally flat pusher end 116 and on the proximal end by an integrally molded plunger engagement member or arm 86 which extends proximally out from the inlet opening 88. As previously discussed, the engagement member 86 is configured to interact with the extension pin 31a (FIG. 7a and 7e) on the syringe 30 to transfer forward motion imparted by the syringe plunger extension pin to the engagement member and as a result to the pusher end 116 of the pressure trigger.

It will be appreciated that when the needle tip guard assembly 16 is activated by the pressure trigger 112, the pusher end 116 of the pressure trigger travels distally to interact with the tapered ramps 110 to consequently disengage the male detents 102 from the stop 81. In an exemplary embodiment, the maximum distal travel of the pressure trigger 112 within the syringe tip engagement chamber 42 for disengaging the male detents 102 is regulated by the configuration of the syringe tip engagement chamber. In the present embodiment, the engagement chamber has a chamber bore 118 that is tapered in the distal direction. The tapered bore 118 is configured to restrict the distal movement of the pressure trigger 112 by constricting against the cylindrical body 74 of the pressure trigger as the pressure trigger travels distally into the engagement chamber. Alternatively or in addition to the tapered bore 118, the cylindrical body 74 may be tapered to provide the same constricting function as the tapered bore. For example, the cylindrical body 74 can have a taper whereby the cross-sectional diameter of the cylindrical body at the inlet opening 88 is larger than the cross-sectional diameter of the cylindrical body at the outlet opening 114.

To provide a leak-free connection between the syringe 30 and the needle hub 14', an interference fit is utilized between several of the components. Turning again to FIG. 7a, a first interference fit is utilized between the syringe tip exterior surface of the syringe 30 and the chamber bore 118 of the syringe tip engagement chamber 42. A second interference is utilized between the exterior surface of the pressure trigger 112 and the chamber bore 118 of the syringe tip engagement chamber 42. Finally, a third interference fit is utilized between the outlet opening 114 of the pressure trigger 112 and the proximal end 115 of the inner needle assembly 52'. The interference fit ensures medication that is discharged from the syringe flows through the needle and not through any other unintended paths.

Referring now to FIG. 7b, which is a cross-sectional view taken at line A-A of FIG. 7a, there is a gap 119 between the internal wall 120 of the passageway and each of the elongated arms 68a', 68b'. The gaps 119 serve as space or clearance for the elongated arms 68a', 68b' to spread apart when the tapered ramps 110 of each of the elongated arms are acted on by the pressure trigger 112. Also shown is a cylindrical pusher chamber 122 for receiving the pressure trigger cylindrical body 74 which moves within the cylindrical pusher chamber to engage the tapered ramps 110 located on the proximal ends of the elongated arms 68a', 68b'.

Referring again to FIGS. 7d and 7e, the pressure fitting 100 comprises a cavity 72 formed in part by the elongated arms 68a', 68b' and a pair of panels 124. Like the embodiment shown in FIGS. 6a-6d, the cavity 72 is configured to receive the resilient member 21 at the resilient member's distal end. In the unactivated position shown in FIG. 7a, the cavity 72 is also configured to telescopically receive and enclose the extension 109 on the distal end of the inner needle assembly 52'. However, it will be appreciated that the present embodiment may be practiced with the cavity 72 eliminated altogether by dispensing with the two panels 124 or by decreasing the length of the panels to form a shorter cavity.

Referring now to FIGS. 8a and 8b, another exemplary embodiment of a safety hypodermic assembly provided in accordance with practice of the present invention is shown. Referring specifically to FIG. 8a, the needle shield assembly 16 of the present embodiment includes a pressure fitting 126 which includes a pair of male detents 102 located on each of the elongated arms 128a, 128b for cocking or securing the pressure fitting 126 against the stop 81 in a similar manner as discussed with reference to FIGS. 7a and 7c. The present embodiment also uses a tapered ramp 110 at the proximal end of each of the elongated arms 128a, 128b as the means for spreading the arms radially apart and consequently disengaging the male detents 102 from the stop 81 to thereby launch the needle tip guard assembly 16. Accordingly, the pusher end 116 of the pressure trigger 130 in the present embodiment is configured to push against the tapered ramps 110 to spread the elongated arms 128a, 128b radially outward and consequently disengage the male detents 102 from the stop 81.

The pressure trigger 130 comprises a cylindrical body 74, an outlet opening 114, and a plunger engaging arm 132. The plunger engaging arm 132 includes the inlet opening 88 which provides a fluid path between the syringe 30, the annular cavity defined by the cylindrical body 74, and the needle 12. The plunger engaging arm 132 is configured to extend into the tip of the syringe 30 and contact the extension pin 31a at a point inside the syringe tip. Thus, the extension pin 31a does not have to extend beyond the syringe tip in order to activate the pressure trigger 130.

As shown in FIG. 8b, the maximum distal travel for the pressure trigger 130 can be controlled or regulated by the stop member 81. In an exemplary embodiment, subsequent to the pusher end 116 acting on the tapered ramps 110 to disengage the pressure fitting 126, the pusher end is configured to abut against the stop member 81 and is limited by the stop member from further distal movement.

Hooks 136 are provided on the proximal ends of the elongated arms 128a, 128b for limiting the distal travel of the pressure fitting 126 once the needle assembly has been activated. The hooks 136 limit the pressure fitting travel by catching the shroud 138 at the circumferential proximal end 140 thereof as the pressure fitting moves distally.

To prevent the pressure fitting 126 from retracting from the need tip once it has been activated, the elongated arms 128a, 128b further include a pair of one-way locks or wings 142 formed at around the anchor point 152 on each of the arms. The one-way locks 142 are configured to abut against the external circumferential distal end 144 of the shroud 138 to thereby prevent the pressure fitting 126 from moving proximally once it has been activated. It will be appreciated by a person of ordinary skill in the art that the shroud 138 is preferably continuous (i.e., there are no slits) so that irrespective of the relative orientation of the pressure fitting 126 and the needle hub 14, the hooks 136 will always catch the circumferential end 140 of the shroud 138 when moving distally, and the one-way locks 142 will always catch the shroud's external circumferential distal end 144 when moving proximally after the activation.

Referring specifically to FIG. 8b, the needle tip guard assembly 145 of the present embodiment, unlike the needle tip guard assemblies in the previously described embodiments, incorporates the functions of both the spring clip 20 and the pressure fitting into a single unitary structure. In the illustrated embodiment, the pressure fitting 126 includes a cylindrical fitting end cap 146 having an opening 148 therethrough that is slightly larger than the outside diameter of the needle 12 so that the pressure fitting can move relative to the needle without being interfered with by the opening. The pressure fitting 126 further includes a needle sheath 150 and the pair of elongated arms 128a, 128b fixedly secured to the fitting end cap 146. The elongated arms 128a, 128b are preferably spaced 180° apart from each other and each has a width that spans an equivalent of approximately 5° to 25° arc circle of the end cap 146. Alternatively, the present embodiment may be practiced with the elongated arms having much wider widths and having three or more arms. The needle sheath 150, which is preferably a cylinder, has a length that is sufficiently long so that the sheath covers the portion of the needle that is expected to be contaminated upon usage.

As will be appreciated by a person of ordinary skill in the art, the length of the elongated arms 128a, 128b from between the anchor point 152, which is proximate the one-way locks 142 and the fitting end cap 146 is sufficiently long so that the pressure fitting 126 extends the entire portion of the needle 12 that extends beyond the needle hub when the assembly is activated. It is understood that the opening 148 on the end cap 146 is sufficiently large so that the end cap can slide distally relative to the needle 12 to shield the needle tip 22 when activated (FIG. 8b). In the present embodiment, the needle 12 preferably does not include a needle stop, such as the needle stop 24 described with respect to previous embodiments, so that the end cap 146 can slide distally of the needle tip without engaging the needle stop. However, it is understood that the present invention may still be practiced with needles which incorporates a needle stop so long as the opening 148 is larger than the largest dimension of the needle stop.

Similar to the embodiment shown in FIGS. 7a-7e, the present embodiment uses an interference fit between the syringe 30 and the needle hub 14' to provide a leak-free connection. Turning again to FIG. 8b, a first interference fit is provided between the exterior surface of the tip of the syringe 30 and the chamber bore 118 of the syringe tip engagement chamber 42. A second interference is provided between the exterior surface of the pressure trigger 130 and the chamber bore 118 of the syringe tip engagement chamber. Finally, a third interference fit is provided between the outlet opening 114 of the pressure trigger 130 and the proximal end 115 of the inner needle assembly 52'.

Turning now to FIGS. 9a and 9b, another exemplary embodiment of a safety hypodermic assembly provided in accordance with practice of the present invention is shown. In this embodiment, the needle hub 151 incorporates an internal needle assembly 52" for fixedly securing the needle 12 to the needle hub, similar to the embodiments discussed with reference to FIGS. 6a and 8a. However, unlike the other embodiments, the present internal needle assembly 52" does not incorporate structures which extends distally beyond the enlarged portion 153. Further unlike the other embodiments (such as the embodiment illustrated in FIG. 7a), the present embodiment has a pair of bumps or protrusions 155 formed at the stop member 81 for engaging the pressure fitting 154, as is further discussed below. The bumps 155 act as extensions of the stop member 81. Because of the absence of the extension structure on the distal end of the needle assembly 52", a resilient member 21 with a slimmer circumferential profile may be used to launch the needle shield assembly 16 as the resilient member is not expected to fit over the extension.

The needle shield assembly 16 includes a pressure fitting 154 which further includes a pair of elongated arms 156a, 156b integrally molded to an end cap 158. The end cap 158 includes an opening 160 that is nominally larger than the diameter of the needle 12, and each of the elongated arms 156a, 156b includes a cut-out 162. When the pressure fitting 154 is inserted into the needle passageway 34 and placed in an unactivated position (FIG. 9a), the cut-outs 162 on the elongated arms are configured to releasably engage the bumps 155, which are located proximate the stop member 81 and act as extensions of the stop member 81. In the unactivated position, the end cap 158 and the enlarged portion 153 act as barriers in maintaining the resilient member 21 in a compressed state. The end cap 158 fixes the resilient member 21 on one of its ends while the enlarged portion 153 fixes the other end. As readily understood, the elongated arms 156a, 156b are resiliently inwardly biased in the direction of the longitudinal axis of the needle to facilitate the engagement between the cut-outs 162 and the bumps 155. In the unactivated position, the pressure fitting 154 is housed completely within the needle passageway 34 while the spring clip 20 partially sits within the spring clip shroud 138 with its distal end extending slightly out from the distal end of the shroud opening.

The elongated arms 156a, 156b further include a pair of tapered ramps 110 at their proximal ends. Similar to the tapered ramps previously discussed (e.g., with reference to FIGS. 7a and 8a), the tapered ramps 110 on the elongated arms and the pusher end 116 of the pressure trigger 130 are means by which the cut-outs 162 are disengaged from the bumps 155 to thereby launch the needle shield assembly 16. The pressure trigger 130 is identical to the pressure trigger discussed with reference to FIG. 8a.

The interaction between the pusher end 116 and the tapered ramps 110 causes the elongated arms 156a, 156b to spread radially outward, as previously discussed, which in turn causes the cut-outs 162 to disengage from the bumps 155. Once disengaged, the resilient member 21 uncoils and pushes distally against the inside surface of the pressure fitting's end cap 158. The resilient member 21 is configured to push the pressure fitting distally until the opening 26 of the spring clip 20, which abuts the end cap, engages the needle stop 24. At this point, the spring arms of the spring clip snap closed over the needle tip and the pressure fitting 154 comes to rest in a position proximal to and adjacent the spring clip.

In the present embodiment, the pressure trigger 130, which is the same as the pressure trigger discussed with reference to FIGS. 8a and 8b, has a maximum distal travel that is limited by the stop member 81, i.e., the pressure trigger 130 moves distally until it contacts the stop 81 with its pusher end 116 (FIG. 9b). Alternatively, the maximum distal travel of the pressure trigger 130 may be regulated by configuring the trigger end wall 164 to abut the proximal end of the internal needle assembly 52". For example, this may be implemented by shortening the length of the pressure trigger cylindrical body 74 or lengthening the inlet portion 166 of the internal needle assembly 52". Alternatively, the internal bore of the syringe engagement chamber 42 may be tapered so that as the pressure trigger 130 moves distally, the tapered internal bore constricts the cylindrical body 74 to prevent further distal travel of the pressure trigger.

The present embodiment also uses an interference fit between the various components to provide a leak-free connection between the syringe 30 and the needle hub 14'. Referring again to FIG. 9b, a first interference fit is provided between the external surface of the tip of the syringe 30 and the chamber bore 118 of the syringe tip engagement chamber 42. A second interference is provided between the exterior surface of the pressure trigger 130 and the chamber bore 118 of the syringe tip engagement chamber. Finally, a third interference fit is provided between the outlet opening 114 of the pressure trigger 130 and the proximal end 115 of the inner needle assembly 52'.

Figure 10A:
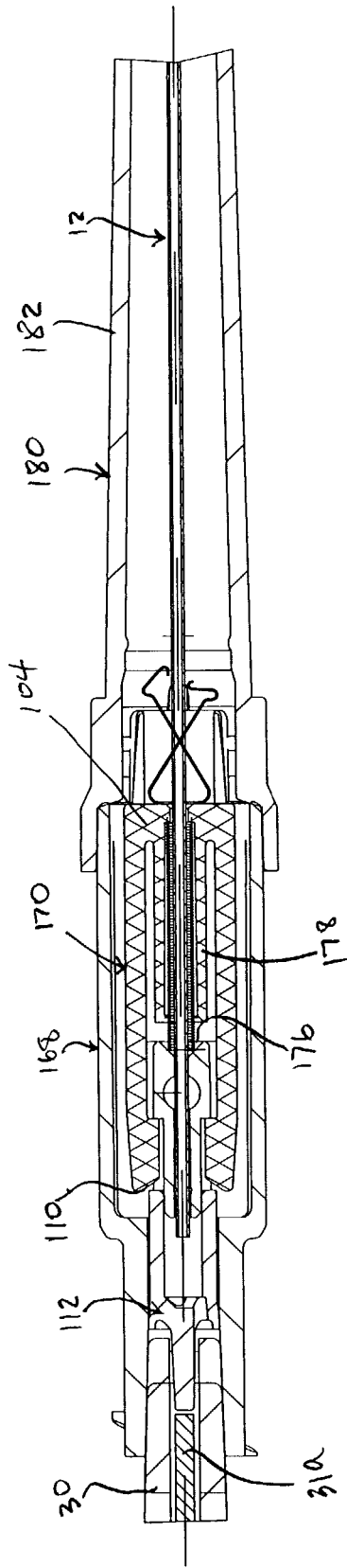
FIG. 10a is a semi-schematic cross-sectional side view of an unactivated hypodermic needle assembly according to the eleventh embodiment of the present invention, which includes a protective cap.
Figure 10B:
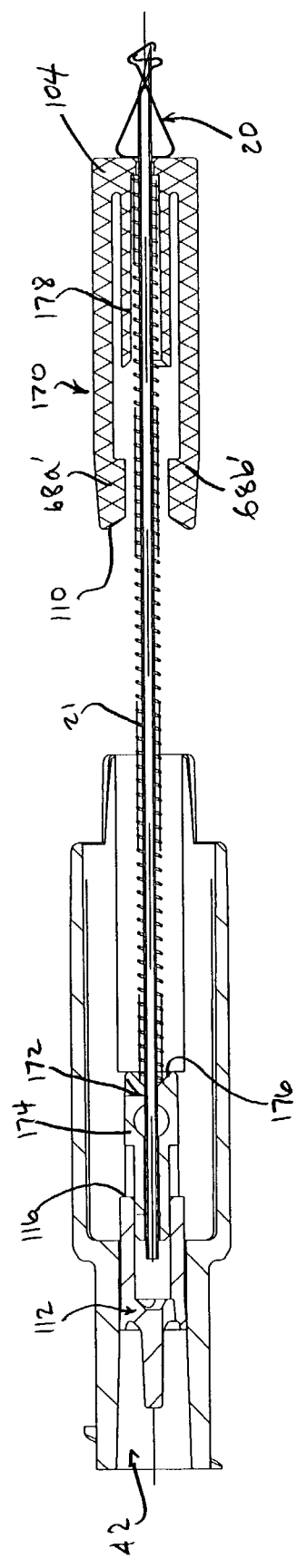
FIG. 10b is semi-schematic cross-sectional side view of the hypodermic needle assembly of FIG. 10a shown in its activated state and attached to a syringe.

Turning now to FIGS. 10a and 10b, another exemplary embodiment of a safety hypodermic assembly provided in accordance with practice of the present invention is shown. The embodiment shown in FIGS. 10a and 10b comprises a similar needle hub 168, pressure trigger 112, and pressure fitting 170 to launch the spring clip 20 as, for example, FIGS. 7a-7e. Furthermore, the means for radially spreading the two elongated arms 68a', 68b' to release the resilient member 21 is the same between the present embodiment and the previously described embodiments, including FIGS. 8a-9b. This includes using a pusher end 116 on the pressure trigger 112 to drive the tapered ramps 110 on the pressure fitting 170 and radially spreading the arms 68a', 68b'.

The inner needle assembly 172, however, has been modified to eliminate distally extending structures beyond the enlarged portion 174. In its place, a recess 176 for receiving the proximal end of the resilient member 21 is provided. Without the extended structure distal of the enlarged portion 174, a resilient member 21 with a slim circumferential profile may directly fit over the needle 12.

The pressure fitting 170 is also similar to the pressure fitting 100 disclosed in FIGS. 7a and 7c. A cylindrical cavity 178, however, has been molded to the distal end 104 of the pressure fitting 170 and is disposed in between the two elongated arms 68a', 68b'. The cylindrical cavity 178 is provided so that the distal end of the resilient member 21 may be enclosed and secured by the cavity, although this cylindrical cavity may be eliminated without deviating from the scope of the present invention.

A protective cap 180 is shown frictionally engaged to the exterior distal end section of the needle hub 168 assembly. The protective cap 180 shields the needle 12 when the needle hub assembly 168 is in the ready position (FIG. 10a), such as in a package during shipping and storage. The cap 180 may be opaque, transparent, or semi-opaque, and has a tapered cone section 182 that spans the length of the needle. Although not shown, the protective cap 180 has a closed distal end that is generally square for shielding the needle tip. Alternatively, the cap may include a straight cylindrical section instead of a tapered cone 182.

Referring now to FIGS. 11a and 11b, there is shown an alternative needle hub assembly provided in accordance with practice of the present invention, which is generally designated 184. The needle hub assembly 184 comprises a generally cylindrical hub 186, a threaded member or luer fitting 188 at the hub's proximal end, and an engagement opening 190 at the hub's distal end. The engagement opening 190 comprises a preformed undercut or groove 192 for mechanical engagement with the spring clip 20 (FIG. 11b). The groove 192 is configured to engage the end wall 28 of the spring clip 20 (FIG. 11b), which is, in turn, configured to hold the resilient member 21 in a compressed or biased state.

An inner needle assembly 194 is used to permanently secure the needle 12 to the needle hub 181 in the manner previously described (See, e.g., discussion with reference to FIGS. 6a-6d). The inner needle assembly 194 is integrally molded to the needle hub 186 (FIG. 11b). However, along its upper and lower surfaces 196a, 196b (FIGS., 11a and 11c), the inner needle assembly 194 is spaced apart from the surface of internal bore 198 of the needle hub 186. This spaced apart configuration defines two passages 200a, 200b adjacent the upper and lower surfaces 196a, 196b of the inner needle assembly 194. The passages 200a, 200b, in turn, provide communication paths for permitting the pressure trigger to 210 to communicate with the washer 206.

A generally circular washer 206, of either plastic or metal, is disposed over the needle 12 just distal of the inner needle assembly 194. The washer 206 comprises a centrally located opening 208 and an outside diameter that is preferably smaller than the diameter of the internal bore 198. The opening 208 allows the washer 206 to slidably mount over the needle and move relative to the needle 12 when the washer is activated, as further discussed below. The washer 206 is configured to hold one end of the resilient member, the proximal end, while the spring clip end wall 28 holds the distal end, which together hold the resilient member compressed in the ready position (FIGS. 11a and 11b).

The pressure trigger 210 shown in FIGS. 11a and 11b is an integrally molded component that includes a plunger engagement arm 212 at the proximal end, a circular base 214, and a pair of trigger arms 216a, 216b molded to the base. A needle engagement arm 218, which includes a hollow bore 220, is molded to the circular base 214 opposite the plunger engagement arm 212 and has a common hollow bore 220 with the latter component. The needle engagement arm 218 is configured to grip the needle's proximal end, via the hollow bore 220, in an interference fit. As in FIGS. 7a-10b, the present embodiment also uses an interference fit between the various components to provide a leak free connection between the syringe 30 and the needle hub 184. When the syringe (not shown) couples to the internal bore 198 and there is an interference fit between the internal bore and the circular base 214 of the pressure trigger 210, then fluid communication is provided between the syringe, the hollow bore 220, and the needle 12.

Figure 11C:
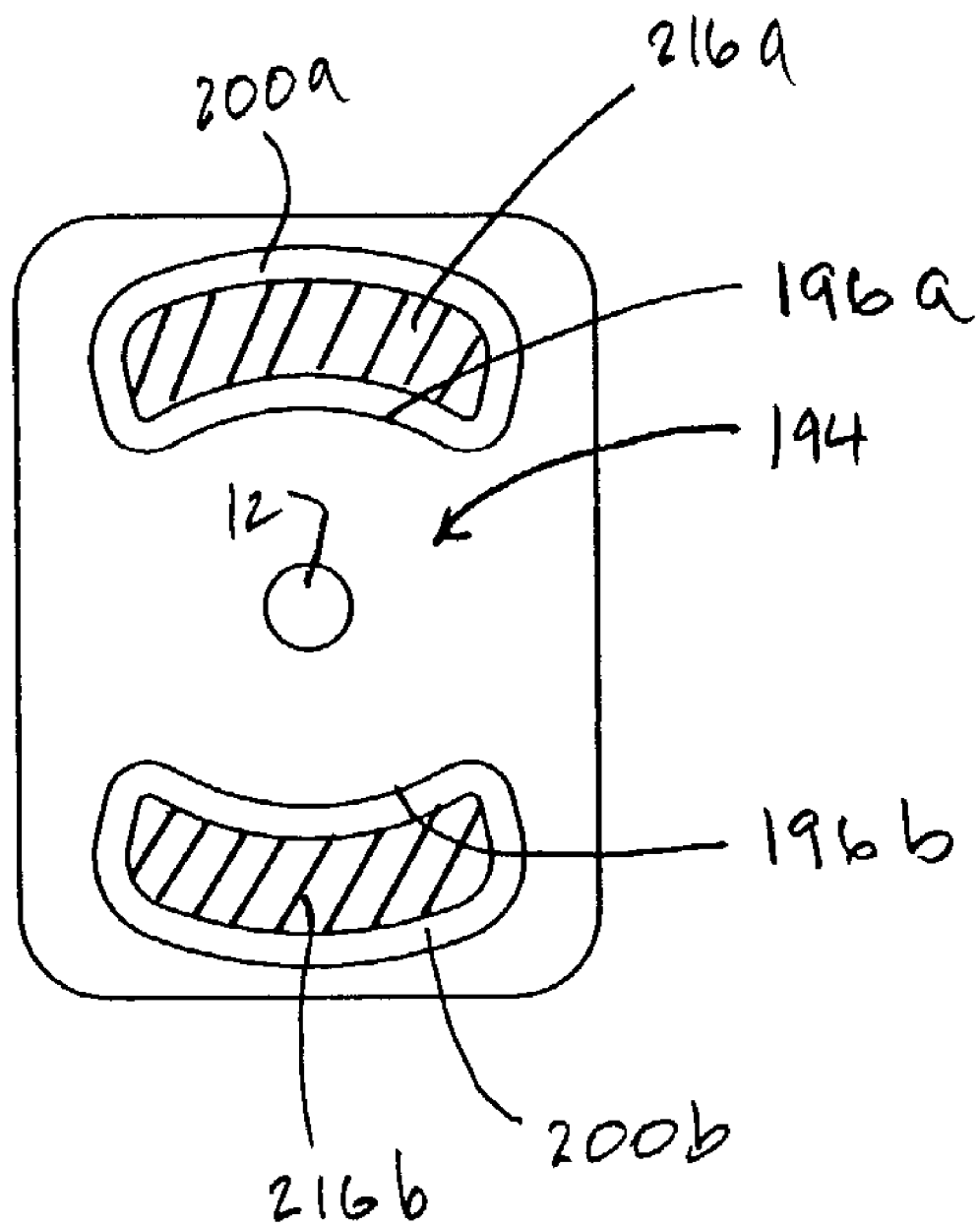
FIG. 11c is a semi-schematic cross-sectional end view of the unactivated hypodermic needle assembly of FIG. 11a taken at line B-B.

Referring now to FIG. 11c, there is shown an exemplary cross-sectional view of the needle hub assembly 184 of FIG. 11a, taken at line B-B. The two passages 200a, 200b are shown with the two trigger arms 216a, 216b passing therethrough. By depressing the plunger on the syringe, the plunger and extension pin 31a (not shown) move distally until the extension pin 31a contacts the proximal end of the plunger engagement arm 212. Further distal movement of the extension pin moves the engagement arm 212 distally, which in turn moves the trigger arms 216a, 216b distally through the passages 200a, 200b so that they engage or contact the washer 206. Still further distal movement of the extension pin 31a on the syringe causes the washer 206 to move distally forward to further compress the resilient member 21 against the end wall 28 of the spring clip 20. As the advancing washer 206 further compresses the resilient member 21, the forward force builds until it exceeds the gripping force formed between the interaction of the undercut groove 192 and the end wall 28 on the spring clip 20. At this point, the spring clip 20 separates from the undercut groove 192 and launches distally relative to the needle 12 due to the action of the expanding resilient member until the needle opening 26 located on the spring clip contacts the needle stop 24. At that point, the spring clip blocks the needle tip 22 in the manner previously discussed.

An alternative needle hub assembly 224 for launching the spring clip 20 without a pressure fitting, similar to the embodiment shown in FIGS. 11a and 11b, is shown in FIGS. 12a and 12b. The alternative needle hub assembly 224 is the same as the needle hub assembly 184 shown in FIGS. 11a and 11b but with the washer 206 eliminated. The proximal end of the resilient member 21 therefore compresses directly against the internal needle assembly 194 in the ready position (FIG. 12a).

The pressure trigger 226 include trigger arms 228a, 228b that directly contact the end wall 28 of the spring clip 20 (FIG. 12b). Like the embodiment shown in FIGS. 11a and 11b, the trigger arms 228a, 228b pass through the two passages 200a, 200b located adjacent the inner needle assembly 194 to communicate with the spring clip 20. During use, when the plunger engagement arm 212 is pushed distally forward by the syringe's extension pin 31a (not shown), the plunger arms move distally forward and contacts the end wall 28 on the spring clip 20. With sufficient distal force, the distal movement causes the end wall to separate from the undercut groove 192. When this occurs, the spring clip 20 launches distally relative to the needle 12 to shield the needle tip 22 from accidental contact therewith.

An alternative needle hub assembly 230 generally characterized by two separate hub components attached to one another to form a complete needle hub is shown in FIGS. 13a and 13b. The two-piece hub embodiment permits a conical spring member 231, which has a larger cross-sectional area than one of the hub components, to be received thereinbetween.

Specifically referring to FIG. 13a, the two-piece hub assembly includes a distal hub section 232 and a proximal hub section 234. The proximal hub section 234 comprises a threaded member or luer fitting 188 at its proximal end and a glue well 238 and a well bore 240 integrally molded to the distal end wall 236. The well bore 240 is configured to receive the needle 12 and the needle is preferably glued to the well bore. Similar to the construction shown in FIG. 11c, the glue well 238 is attached to the hub and has two passages 244a, 244b located adjacent thereto, between the upper and the lower surfaces of the glue well 238. The passages 244a, 244b are for facilitating communication between the pressure trigger 226 and the spring clip, as further discussed below. A male detent 246 preferably in the shape of a ring is located at the distal end of the exterior surface of the proximal hub section 234. The male detent 246 is configured to engage the distal hub section 232 when the distal hub section is joined to the proximal hub section. As with other embodiments, the syringe tip engagement chamber 42 preferably engages a syringe tip (not shown) in an interference fit.

The distal hub section 232 comprises a cylindrical section 248 and a cone section 250. The cylindrical section further comprises a lip 251 for engaging the male detent 246 on the proximal hub section 234 and the cone section further comprises a preformed undercut or groove 252 for engaging the proximal end of the spring clip. To facilitate sliding the lip 251 over the male detent 246, the cylindrical section 248 on the distal hub section 232 may optionally include two or more slits to enable it to spread or deflect as the lip 251 slides over the male detent 246 to mate with the proximal hub section 234.

The conical spring 231 in the present embodiment has a large proximal end 254, a tapered spring section 256, and a relatively smaller distal end 258, which is configured to closely fit over the needle shaft 12. In the compressed state (FIG. 13a), the conical spring 231 compresses and resembles a cone with the large proximal end 254 of the cone abutting against the male detent 246 on the proximal hub section 234 and the small distal spring end 258 being pressed against by the spring clip 260. When the conical spring 231 expands, as further discussed below, it retains its conical shape. As readily apparent by the configuration shown in FIG. 13a, the conical spring requires the opening at the distal hub section 232 to be sufficiently large to enable the conical spring 231 to expand unimpededly when released from its compressed position.

The spring clip 260 utilized in the present embodiment is similar to the spring clip 20 previously described with reference to FIG. 11b. It is similar in that it comprises an end wall 262, two spring arms 264, an end wall opening 265, and two distal end walls or fingers 266. However, to engage with the preformed undercut or groove 252 in the ready position, the end wall 262 is correspondingly increased to match the required dimension of the undercut groove 252.

Referring now to FIG. 13c, there is shown an end view of the conical spring 231 of FIG. 13a in the compressed state. The conical spring 231 is formed with openings 268a, 268b to permit communication between the pressure trigger 226 and the spring clip 260 (FIG. 13a). It is understood that when the spring 231 is in the compressed state (FIG. 13a), the spring's openings 268a, 268b align with the two passages 244a, 244b on the needle hub to permit communication between the pressure trigger 226 and the spring clip 260.

The pressure trigger 226 utilized in the present embodiment is the same as that shown in FIGS. 12a and 12b in that it has a pair of trigger arms 228a, 228b for directly contacting the spring clip end wall 262. The trigger arms 228a, 228b pass through the passages 244a, 244b adjacent the glue well 238 and the openings 268a, 268b formed in the conical spring to contact the spring clip end wall 262. The pressure trigger 226 has the same plunger engagement arm 212, circular base 214, needle engagement arm 218, and hollow bore 220 as the pressure trigger shown in FIGS. 11a-12b.

To launch the spring clip 260 and shield the needle tip 22 after an injection, the pressure trigger 212 is advanced distally by a syringe's extension pin (not shown). When so advanced, the trigger arms 228a, 228b move distally forward with the same forward force against the spring end wall 262. The forward force generated by the distal movement on the end wall 262 is opposed by a restraining force formed by the engagement between the hub's preformed undercut 252 and the spring clip 260. The forward force eventually overcomes the restraining force. At which point, the spring clip 260 separates from the undercut groove 252 and launches distally forward due to the releasing action of the conical spring member 231 to block the needle tip 22, in the manner previously discussed.

An alternative needle hub assembly 270 with a pressure fitting 272 is shown in FIG. 14a. The needle hub assembly 270 provided in accordance with practice of the present invention comprises a needle hub 274, an inner needle assembly 276, and a pressure trigger 278. The needle hub 274 incorporates an annular space 280 defined by the space formed between an inner cylinder 280 and an outer cylinder 284.

The outer cylinder 284 is longer than the inner cylinder 280 and has a preformed undercut or groove 286 formed at the longer section, on the distal end, thereof for receiving the pressure fitting 272. The pressure fitting 272 attaches to the preformed undercut 286 via a base section or flange 288, which wedges into the undercut. The base section 288 of the pressure fitting 272 comprises a distally extending collar 290 of sufficient length to cover the spring clip 20, as shown in FIGS. 14a and 14b. The base section 288 also includes a proximally extending collar 292 for abutting against the distal end of the pressure trigger 278.

The inner needle assembly 276 is formed to the inner cylinder 280 in the same fashion as previously discussed. As before, two passages 294a, 294b located adjacent the inner needle assembly 276 are provided for communication between the pressure trigger 278 and the pressure fitting 272.

The inner needle assembly 276 comprises a bore 296 for receiving and fixing the needle 12 thereto. A glue well 297 is included in the present embodiment for fixedly securing the needle with glue.

Along its external surface, the inner needle assembly 276 is provided with a stepped collar 298 at the transition between a small proximal end section 300 and a large distal end section 302, relative to one another. This stepped collar 298 is preferably tapered and provides a sealing function between the pressure trigger 278 and the inner needle assembly 276, as further discussed below.

The pressure trigger 278 is similar to the pressure trigger discussed with reference to FIGS. 8a-9b in that it includes a plunger engagement arm 132, an inlet opening 88, and two trigger arms 304a, 304b, with two exceptions. First, the trigger arms 304a, 304b are provided with sufficient length to pass through the passages 294a, 294b so that they may directly contact the proximally extending collar 292 of the pressure fitting 272 (FIG. 14a). Second, the pressure trigger 278 is provided with a similar but opposing stepped collar for engaging with the stepped collar 298 of the inner needle assembly 276. As before, the exterior surface of the pressure trigger 278 preferably has a slight interference fit with the surface of the internal bore 242 of the needle hub 274 and there is a slight interference fit between the interior surface of the pressure trigger 278 and the inner needle assembly 276 to prevent unwanted leakage or bypass.

In the ready position (FIG. 14a), the resilient member 21 resides in the annular space 280 of the needle hub 274 and is compressed by the base section 288 of the pressure fitting 272. The engagement between the pressure fitting 272 and the needle hub 274 provides a restraining force that opposes the expansion force of the resilient member 21 when the resilient member is compressed and the needle hub 270 is in the ready position. As readily understood by a person of ordinary skill in the art, the present embodiment has an overall assembly length that is less than the length of earlier discussed embodiments. In part, this is achieved by incorporating the annular space 280 for seating the resilient member 21 further proximally than the earlier discussed embodiments, which do not incorporate the annular space. As a result, this decreases the overall length of the needle hub 274.

FIG. 14b shows a cross-sectional view of the needle hub assembly 270 taken at line E-E of FIG. 14a. As shown, the resilient member 21 is positioned within the annular space 280 between the outer cylinder 284 and the inner cylinder 282. The trigger arms 304a, 304b are shown disposed in the passages 294a, 294b adjacent the inner needle assembly 276.

In use, the female luer fitting 242 of the needle hub assembly 270 is mated with a male luer fitting located on the syringe 30. The syringe tip is preferably engaged with the syringe tip engagement chamber 42 in an interference fit. Medication in the syringe is dispensed by advancing the plunger (not shown), which forces medication out from the syringe tip and into the opening 88 of the plunger engagement arm 132, where it then exits through the needle 12. As medication completely empties from the syringe 30, the syringe's extension pin 31a abuts the tip of the plunger engagement arm 132 (FIG. 14c).

At this point, further distal movement of the extension pin 31a causes the pressure trigger 278 to move distally, which causes the trigger arms 304a, 304b to ride up against the proximally extending collar 292 of the pressure fitting 272 (FIG. 14a). As this occurs, a forward force is applied to the pressure fitting 272, which, at a certain point, exceeds the restraining force provided by the engagement between the base section 288 and the preformed undercut 286 located on the outer cylinder 284. This in turn causes the pressure fitting 272 to separate from the preformed undercut 286 and launches distally by the expanding action of the resilient member 21. As the pressure fitting 272 moves distally, it pushes the spring clip 20 distally to shield the needle tip from accidental contact therewith. The forward distal movement of the spring clip 20 is stopped by the engagement between the opening on the end wall 28 of the spring clip and the needle stop 24, as previously discussed.

Although not shown, a protective cap may be used with the present embodiment, or other embodiments described herein, to cover the needle 12 for packaging and/or shipment. If implemented, the protective cap may couple to the needle hub 274, via a detent engagement. The needle cap may be made form a clear, an opaque, or a semi-opaque thermoplastic material and may have ribs and varying contours for aesthetic value.

At the distal end of the distally extending collar 290 is an end wall 291 which has an opening 293. The opening 293 is sized to allow the needle crimp 24 to pass through but not to allow the closed spring clip distal walls 94a and 94b to pass through. In this manner, the pressure fitting 272 cannot be pushed back against the resilient member 21 after the needle tip 22 has been protected or shielded, as was the case with the embodiments shown in FIGS. 1a-7e, 9a-10b. The spring clip 20 is protected against manipulation and the patient does not have to come into contact with the spring clip 20.

The pressure fitting 272 can be formed as a single molded piece with the opening 293 large enough to permit the entire spring clip 20 to pass into the distally extending collar 290. After the spring clip 20 is positioned therein, the opening 293 can be reduced by pressing the distal end into a steel form or die to create the end wall 291. Alternatively, the pressure fitting 272 can be formed from two molded parts, which are then assembled over the spring clip 20.

FIG. 15a shows a syringe 306 provided in accordance with practice of the present invention. The syringe 306 shown includes traditional syringe components such as a barrel 308, a plunger or shaft 310, threaded receptacle 312, a male luer syringe tip 314, an extension pin 316, a plunger tip 318, a push flange 319, and a gripping member 320. The barrel 308 further has an open inlet end 309 and a closed outlet end 311 having an opening that terminates into the syringe tip 314.

In the present embodiment, the distal end of the plunger 310, adjacent the extension pin 316, incorporates a primary pusher end 322 and a secondary pusher end 324, with the two pusher ends being separated from one another by a trigger gap 326. The primary pusher end 322 is integrally molded to the plunger and to the extension pin 316 is fixedly attached to the primary pusher end. The secondary pusher end 324 is attached to the extension pin 316 by a frangible seal 328. The frangible seal is configured to tear from the extension pin 316 under a tear-away force $F_t$, which is greater than a distal force $F_d$ generated to move the plunger 310 from a first position to a second position to dispense/inject medication. The secondary pusher end 324 comprises a distally projecting engagement tip 330 for engaging the plunger tip 318.

In use, medication located in the barrel 308, in the variable medication chamber between the plunger tip 318 and the closed outlet end 311, is discharged by advancing the plunger 310 with a distal force $F_d$ to move the plunger and plunger tip from a first position to a second position, or until the plunger tip contacts the closed outlet end 311 of the barrel (FIG. 15a) to completely or substantially dispense all of the medication from the barrel 308. Also at this point, the tip 332 of the extension pin 316 is preferably positioned evenly with the distal end 334 of the syringe tip. The relative positioning between the extension pin 316 and the syringe tip may alternatively be different depending on the particular combination of components being used, which will be apparent from the following disclosure.

If a tear-away force $F_t$ is now applied to the push flange 319, the frangible seal 328 will tear and the plunger 310 will advance distally to a third position by a distance approximately equal to the trigger gap distance 326, which is the position the primary pusher end 322 travels relative to the secondary pusher end 324 to collapse, merge, or touch one another (FIG. 15b). By a corresponding motion, the tip 332 of the extension pin 316 travels an equal distance relative to the distal end 334 of the syringe tip 314. The plunger travels from between the first position to the second position and from the second position to the third position provides the user of the syringe with (1) an indication when medication is completely or substantially discharged from the variable medication chamber; and (2) a recognizable trigger point for when the needle shield is to be activated by providing a distinct feel when the tear-away force $F_t$ is applied to move the primary pusher end 322 towards the secondary pusher end 324.

FIG. 15c shows the syringe 306 discussed with reference to FIG. 15a in use with an exemplary needle hub assembly 336. More specifically, FIG. 15c shows the syringe 306 with a distal force $F_d$ applied to the plunger 310 to empty the medication from the variable medication chamber and the plunger tip 318 rested against the closed outlet end 311 of the barrel 308. For reference purposes, this plunger tip 318 position will be referred to as a pre-launch position.

The needle hub assembly 336 shown is similar to a combination of needle hub assemblies described above, such as a combination of FIGS. 7a and 10a, with some minor variations. In the needle hub assembly 336 shown, the pressure trigger 338 comprises a pusher end 340 for pushing against the tapered ramps 110 located on the pressure fitting 342, as previously discussed. The pressure trigger 338 also comprises a port 339 for fluid communication between the syringe and the needle 12. Furthermore, the pressure trigger 338 preferably has a slight interference fit with the internal bore 242 of the needle hub 344 and an interference fit between the syringe tip engagement chamber 42 and the male luer syringe tip 314 (FIG. 15c) for minimizing or eliminating unwanted leakage. However, the pressure trigger 338 does not have a proximally extending plunger engagement arm. Thus, unlike the earlier embodiments, such as FIGS. 7a and 10a, the extension pin 316 does not engage with any part of the pressure trigger 338 but only pushes against the pressure trigger. However, whether the extension pin 316 engages any part of a pressure trigger depends on the particular needle hub assembly used for injecting a patient. It is therefore understood that changes in the way the extension pin 316 touches or engages with the pressure trigger 338 can vary depending on the particular needle hub assembly used with the syringe 306. All such variations are contemplated to fall within the scope of the present invention.

To activate the needle shield 20 and shield the needle tip 22 from possible accidental contact therewith after the plunger 310 reaches the pre-launch position, a tear-away force $F_t$ is applied to the plunger. This causes the frangible seal 328 to tear from the extension pin 316 and the primary pusher end 322 to close in on or collapsed upon the secondary pusher end 324. For reference purposes, this position will be referred to as a syringe launched position.

Concurrently with the tearing of the frangible seal 328, the extension pin 316 moves forward an equal distance as the distance traveled by the primary pusher end 322, i.e., the trigger gap 326 distance. This travel moves the extension pin tip 332 distally forward to push the pressure trigger 338 also distally forward. As previously discussed, when this occurs, the pusher end 340 imparts a pair of component forces against the tapered ramps 110 on the pressure fitting 342 and spread the pair of elongated arms 350a, 350b radially outward. When the radial arms spread sufficiently apart so that the male detents 102 clear the stop 81 on the inner needle assembly 52", the resilient member is released and expands distally forward, which then pushes the pressure fitting 342 and the needle shield 20 distally forward to shield the needle tip, as previously discussed.

In the present embodiment, the pressure fitting 342 preferably comprises a pair of distally extending gripping fingers 346a, 346b distal of the fitting end cap 348 for engaging a portion of the needle shield 20. In the launched position (FIG. 15d), the engagement between the pressure fitting 342 and the needle shield 20, via the gripping fingers, minimizes the likelihood that the two, either accidentally or intentionally, separates from one another. With separation, the pressure fitting 342 can ram against the needle shield 20 after the needle shield is in the shielded position and the opening on the end wall 28 is in contact with the needle stop 24. For example, the user can grasp the pressure fitting 342, moves the pressure fitting proximally to compress the resilient member 21, then releases the pressure fitting so that it launches proximally against the needle shield 20 to ram the needle shield. If this ramming by the pressure fitting 342 against the needle shield 20 is repeated, the opening on the needle shield may eventually widen by the needle stop 24, which acts as a wedge, to a point where the spring clip 20 will not stop and will spring over the needle tip 22.

Figure 16:
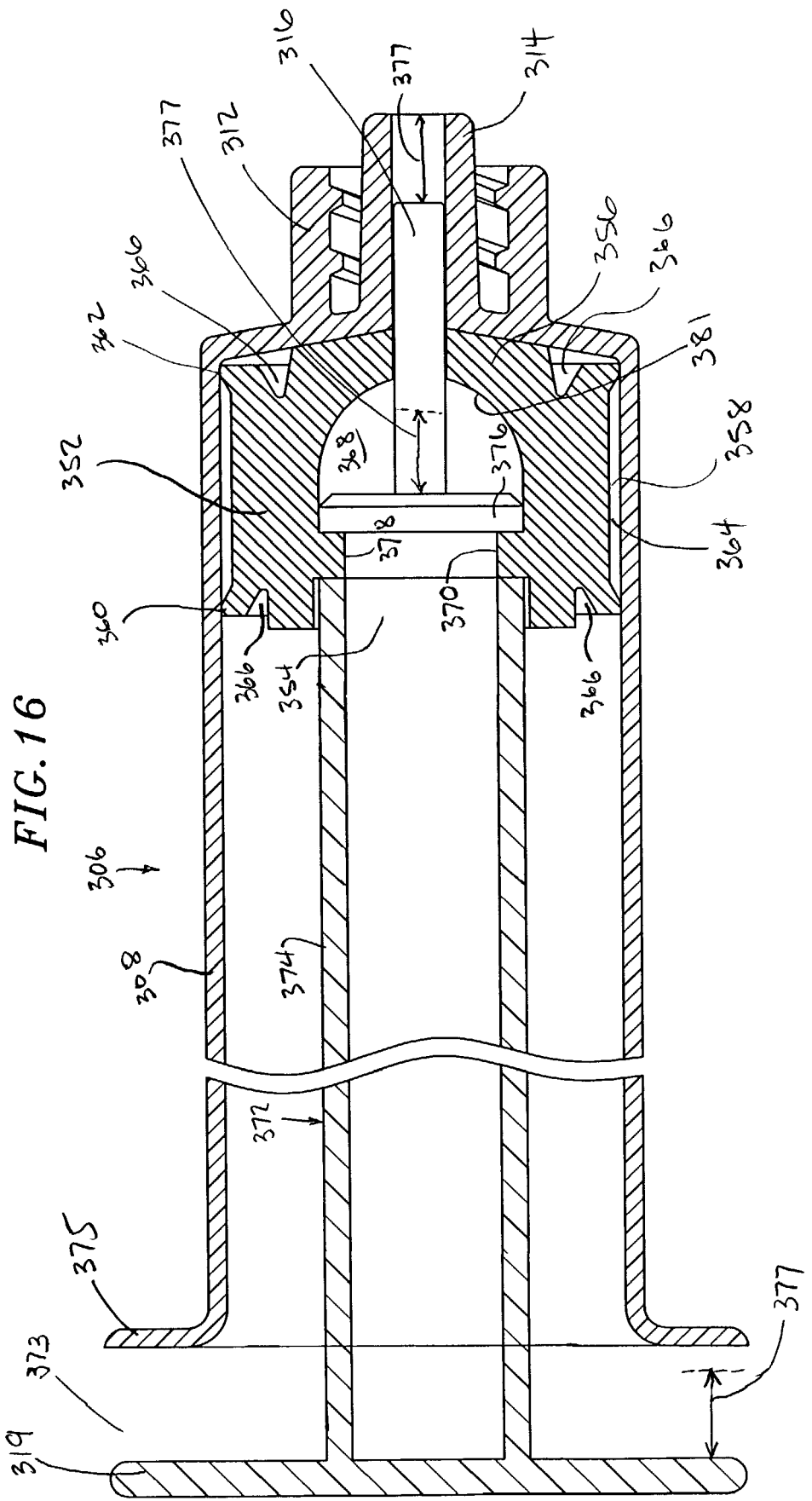
FIG. 16 is a semi-schematic cross-sectional side view of an alternative syringe with a trigger gap provided in accordance with practice of the present invention.

FIG. 16 shows the syringe 306 with a modified plunger tip 352. The modified plunger tip 352 comprises an open end 354, a closed end 356 having an opening for receiving the syringe extension pin 316, and an exterior plunger tip surface 358. The exterior surface 358 further comprises a proximal raised portion 360 and a distal raised portion 362, each raised portion being configured to contact with the interior surface of the syringe barrel 308 to function as sealing means. The proximal and distal raised portions 360, 362 defining a channel 364 therebetween. At the open end 354 and the closed end 356, the plunger tip 352 also comprises expansion grooves 366 for allowing the plunger tip to expand into the grooves when a tear-away force $F_t$ is applied to move the plunger 372 from a pre-launch position to a launched position, as further discussed below. The plunger tip 352 further includes an interior cavity 368 and a ring 370 protruding from the interior cavity.

The plunger 372 comprises a shaft or rod 374, which has a proximal end 373 having a push flange 319 and a distal end 376. The distal end 376 has a groove 378 for engaging with the ring 370 on the plunger tip 352. During engagement, the distal end 376 of the plunger 372 is spaced apart from the closed end of the plunger tip 352 by a trigger gap 377 plus an incremental distance provided by the curvature of the closed end. A similar gap 377 is present at the proximal end of the syringe 306, between the push flange 319 and the gripping flange 375. The engagement between the ring 370 and the groove 378 allows the plunger 372 to move the plunger tip 352 distally from a first position to a second position whenever a distal force $F_d$ is applied to the plunger (the first position being a position that corresponds to a syringe filled position, i.e., a position in which the syringe contains fluids or medicine, and the second position being a position in which the plunger is moved to discharge the medication). The distal force $F_d$ will move the plunger tip 352 distally until the plunger tip reaches the top-dead position or pre-launch position (FIG. 16). To close or take up the trigger gap 377, a tear away force $F_t$ is applied to the plunger 372 to tear away or separate the engagement between the ring 370 and the groove 378. When this occurs, the plunger 372 will move distally relative to the plunger tip 352 or from the second position to a third position. As the plunger 372 moves distally to the third position, the plunger tip deforms due to the ring 370 riding over the surface of the plunger 372. As readily apparent, the channel 364 and the expansion grooves 366 on the plunger tip 352 provide space for the plunger tip to radially expand as the advancing plunger 372 distorts the plunger tip.

When the plunger 372 moves the trigger gap 377 distance, the tip of the extension pin 316 moves a corresponding distance relative to the syringe tip 314. This tip travel may be incorporated to push, for example, a pressure trigger on a needle hub assembly, such as the ones shown in FIGS. 11a and 12a, to launch a spring clip to block a needle tip, as previously discussed. Similarly, the push flange 319 moves the trigger gap 377 distance relative to the gripping flange 375 located on the barrel whenever the plunger 372 moves the trigger gap distance.

Figure 17:
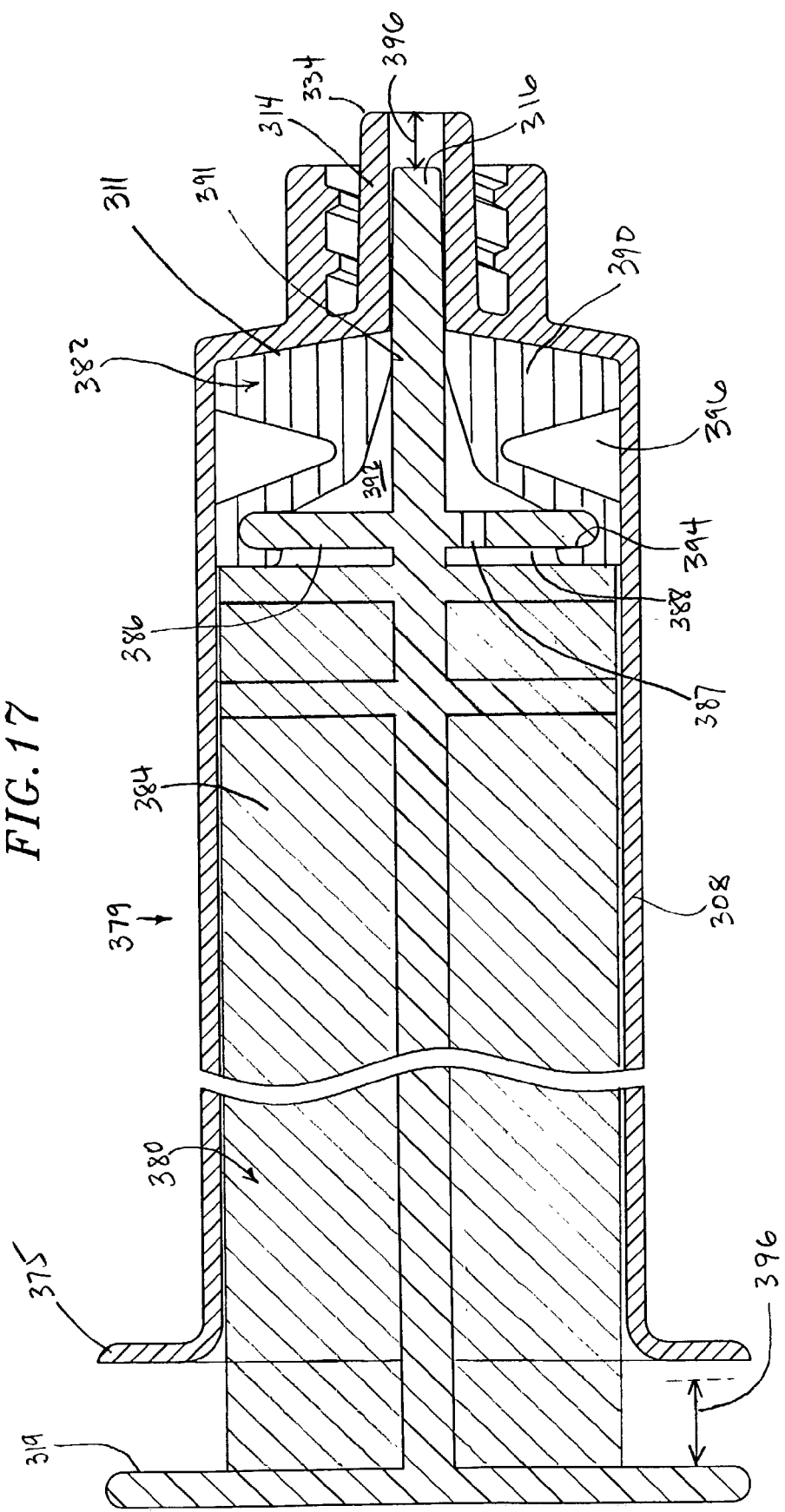
FIG. 17 is a semi-schematic cross-sectional side view of an alternative syringe with a trigger gap provided in accordance with practice of the present invention.

FIG. 17 depicts a syringe 379 having a plunger 380 with a collapsible plunger tip 382 and a conventional barrel 308. The plunger 380 in the present embodiment comprises a rod or shaft 384, a push flange 319 integrally molded to the rod, and a vent hole 387 disposed on the pusher plate 386 for venting trapped air in between the pusher plate and the plunger tip 382. At the distal end of the shaft 384 is an extension pin 316, which extends distally of the pusher plate 386. As shown, the extension pin 316 terminates inside the syringe tip 314, short of the distal end 334 of the syringe tip by a distance that is approximately equal to a trigger gap distance, as further discussed below. This embodiment is therefore configured to be used with a needle hub assembly that employs a pressure trigger with a syringe tip engagement pin, such as hub assemblies shown FIGS. 5b, 6a, and 7a. The syringe tip engagement pin would extend into the syringe tip 314 to contact with the extension pin 316.

The plunger tip 382 comprises an open end 388, a closed end 390 having an bore 391 for receiving the extension pin 316, and an annular space 392 defined therebetween. The plunger tip 382 also includes an engagement groove 394 located near the open end 388 for engaging the pusher plate 386. The plunger tip 382 also has a compression groove 396 located externally of the annular space 392 in between the open end 388 and the closed end 390, or between the proximal end and the distal end, to permit the plunger tip to compress upon itself when a tear-away force $F_t$ is applied, as further discussed below.

Assume for purposes of the following disclosure that a needle hub assembly having pressure trigger with a syringe tip engagement pin is connected to the syringe 379. Examples of possible needle hub assemblies include those shown in FIGS. 5b, 7a, and 10a. The syringe 379 shown in FIG. 17 is in a pre-launch position, which is a position in which a distal force $F_d$ has been applied to move the plunger 380 distally forward from a first position to a second position to dispense medication. This position also coincides with the position in which the plunger tip 382 comes to rest against the closed end 311 of the barrel 308.

To launch the needle shield from the pre-launch position, the plunger 380, and hence the extension pin 316, must move the pressure trigger distally to release the resilient member. Applying a tear away force $F_t$ to the push flange 319 located on the proximal end of the plunger 380 will perform this task. The tear away force $F_t$ applied to the plunger causes the pusher plate 386 to compress the proximal portion against the distal portion of the plunger tip 382. When so compressed, the compression groove 396 collapses to provide the necessary space for the pusher plate 386 to advance distally forward. The distance the plunger 380 moves when the plunger tip 382 compresses onto itself is approximately the width of the compression groove 396 taken at its widest measurement. This gap is also previously referred to as a trigger gap.

When the plunger 380 moves the distance of the trigger gap upon application of the tear-away force $F_t$, the extension pin 316 moves a corresponding distance 396 thereto. As previously discussed, the extension pin 316 then moves the pressure trigger to launch the spring clip to block the needle tip from accidental contact therewith. Similarly, the push flange 319 moves the trigger gap distance 396 relative to the gripping flange 375 located on the barrel 308 whenever the plunger 380 moves the trigger gap distance.

Figure 18A:
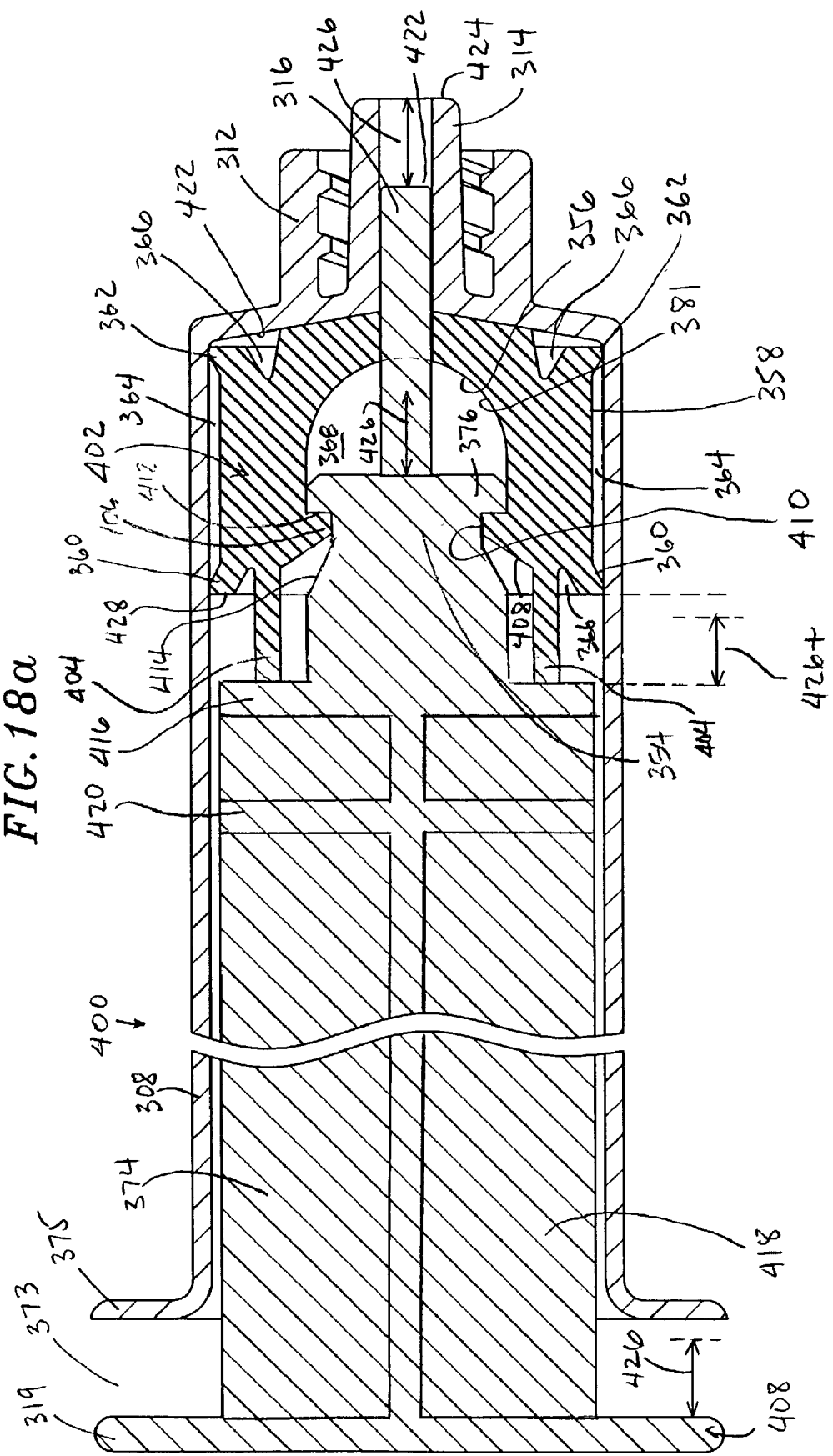
FIG. 18a is a semi-schematic cross-sectional side view of another alternative syringe with a trigger gap provided in accordance with practice of the present invention.

FIG. 18a shows an alternative syringe 400, which also incorporates a trigger gap for triggering a pressure trigger on a needle hub assembly, which is similar to the syringe described with reference to FIG. 16. The alternative syringe 400 comprises a plunger tip 402 having an open end 354, a closed end 356 having an opening for receiving a syringe extension pin 316, and an exterior plunger tip surface 358. The exterior surface 358 further comprises a proximal raised portion 360 and a distal raised portion 362, each raised portion being configured to contact with the interior surface of the syringe barrel 308 to function as sealing means. The proximal and distal raised portions 360, 362 defining a channel 364 therebetween. At the open end 354 and at the closed end 356, the plunger tip 402 also comprises expansion grooves 366 for allowing the plunger tip 402 to expand into the grooves when a tear-away force $F_t$ is applied to move the plunger 408 from a pre-launch position to a launched position, or a second position to a third position, as further discussed below.

The plunger tip 402 further includes an interior cavity 368 and a ring 406 protruding from the interior cavity. Unlike the ring 370 in FIG. 16, the ring 406 disclosed in the present embodiment comprises a tapered surface 408 that tapers in the direction of the open end 354. At the junction between the tapered surface 408 and the expansion groove 366, the plunger tip 402 includes two proximally extending bendable legs 404. Assuming that the plunger 408 and the plunger tip 402 are positioned proximally within the barrel 308 and the barrel contains fluids in the variable medicine chamber (i.e., the first position), the bendable legs 404 are configured to be pushed by the plunger 408 as the plunger moves distally to inject fluids from the syringe (FIG. 18a). In other words, the bendable legs 404 are configured to withstand a distally directed force $F_d$ to move the plunger 408 and the plunger tip 402 from the first position to the second position to inject fluids without bending.

The plunger 408 in the present embodiment comprises a shaft or a rod 374, which has a proximal end 373 and a distal end 376. The distal end 376 has a groove 410 for engaging with the ring 406 on the plunger tip 402. To corresponding to the profile of the ring 406, the groove 410 has a flat side 412 and a tapered side 414, which preferably has a smaller slope relative to the tapered surface 408 on the plunger tip 402. Thus, the tapered side 414 on the shaft 374 and the tapered surface 408 on the plunger tip 402 preferably do not contact when the syringe 400 is in either the first position or the second position (FIG. 18a).

The plunger rod or shaft 374 includes an integrally molded first push flange 416 that is positioned just proximally of the tapered side 414 of the groove 410. The first push flange 416 is reinforced by a plurality of ribs 418 and an optional second push flange 420. As readily apparent, when the shaft 374 is moved distally with a distally directed force $F_d$, a corresponding force is applied on the plunger tip 402 via the first push flange 416 applying the same distally directed force $F_d$ on the bendable legs 404.

Figure 18B:
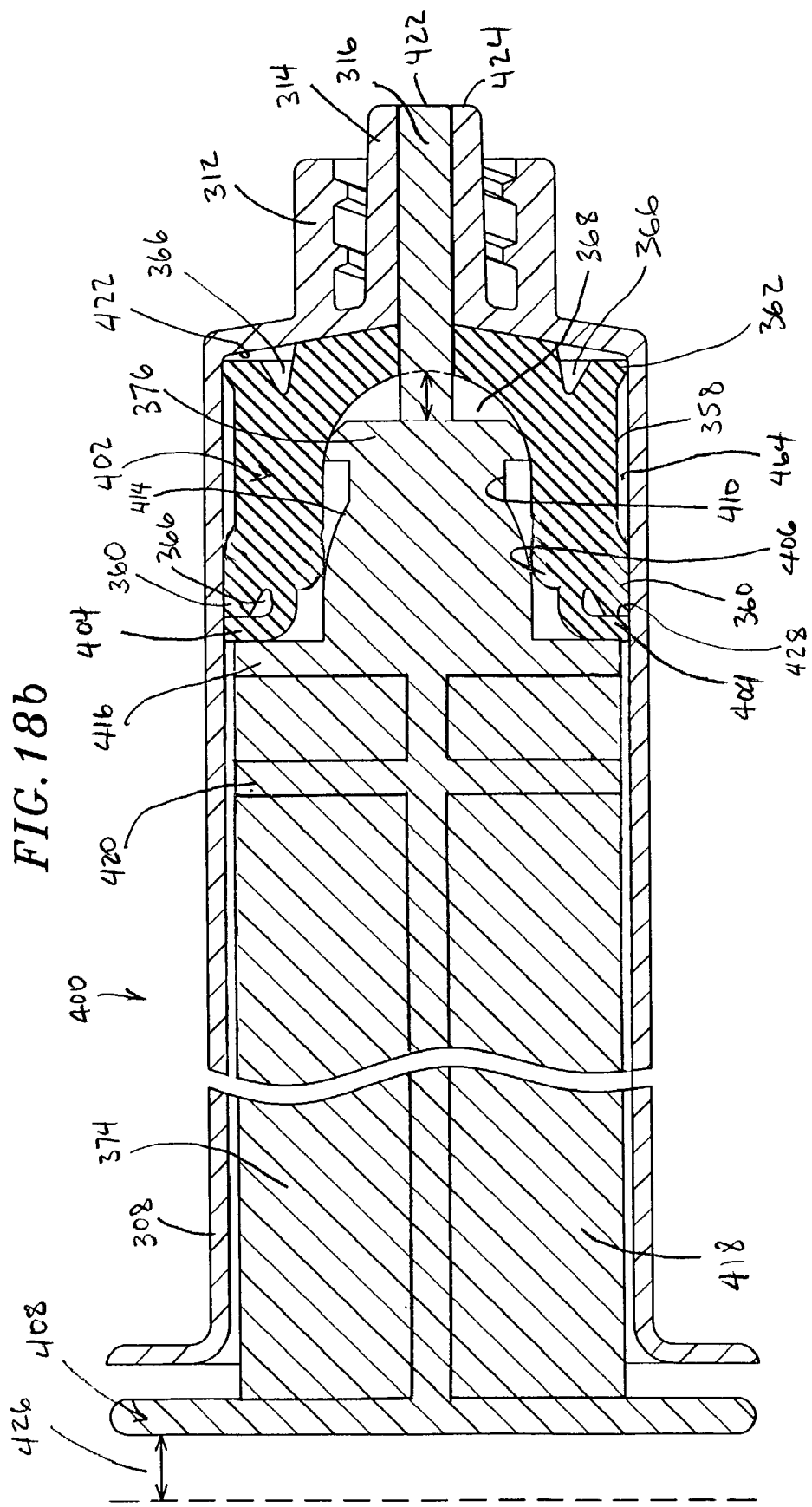
FIG. 18b is a semi-schematic cross-sectional side view of the alternative syringe of FIG. 18a in a triggered mode.

Referring again to FIG. 18a, the syringe 400 is shown in the second position or empty position, which is the position in which the plunger tip 402 contacts the end wall 422 of the syringe. In this position, the distal tip 422 of the extension pin 316 is spaced apart from the tip 424 of the syringe tip 314 by a trigger gap distance 426. In this second position, the first push flange 416 is spaced apart from the end surface 428 of the proximal raised portion 360 of the plunger tip 402 by approximately the same trigger gap distance 426 plus the width of the bendable leg 408 (FIG. 18b). Also in this second position, the distal end 376 of the shaft 374 is spaced part from the curvature 381 of the plunger tip 402 by the trigger gap distance 426 plus an incremental distance formed by the curvature. Similarly, the push flange 319 on the plunger 408 is spaced apart from the gripping flange 375 by the trigger gap 426 distance plus a small nominal distance, which is at least equal to the width of the bendable legs 404.

To close or take up the trigger gap 426, a tear away force $F_t$ is applied to the plunger 408 to move the plunger from a second position to a third position (FIG. 18b). As previously discussed, the tear away force $F_t$ is greater than the distally directed force $F_d$. When this occurs, the first push flange 416 applies the same tear away force $F_t$ on the bendable legs 404 located on the plunger tip 402, which causes the bendable legs to flex or give under the applied force. The plunger 408 then moves distally relative to the plunger tip 402 until the first push flange 416 bottoms out on the bendable legs 404 (FIG. 18b). At this point, the distal tip 422 of the extension pin 316 will have moved the trigger gap distance 426 relative to the tip 424 of the syringe tip 314.

As shown in FIG. 18b, when the plunger 408 moves to the third position, the ring 406 on the plunger tip 402 rides up on the tapered side 414 of the groove 410 and are radially expanded by the plunger. This in turn causes the syringe tip 402 to radially expand in the same general region, as indicated by a portion of the exterior surface 358 radially expanding and contacting the inside diameter of the barrel 308.

As previously discussed with reference to FIGS. 16 and 17, when the plunger 408 moves the trigger gap distance 426, the tip 422 of the extension pin 316 moves a corresponding distance relative to the syringe tip 314. This tip travel may be incorporated to push, for example, a pressure trigger on a needle hub assembly, such as the ones shown in FIGS. 11a and 12a, to launch a spring clip to block a needle tip.

FIGS. 19a-19d shows an alternative hypodermic needle assembly provided in accordance with the seventeenth embodiment of the invention, which is generally designated 430. The hypodermic needle assembly 430 includes a needle hub 432, which has a proximal end 434 with a locking element such as a luer fitting 188, and a distal end 436 with a needle 12 protruding therefrom. The needle hub 432 further includes an annular space that is defined by the space formed between an inner cylinder 438 and an outer cylinder 440 for receiving a resilient member 21. As shown, the outer cylinder 440 has a distal end 436 that is relatively longer than the distal end 444 of the inner cylinder 438. For molding purposes, a pair of slots 439 are located in each of the inner and outer cylinders 438, 440 for forming the inner needle assembly 446.

The inner needle assembly 446 is incorporated in the present embodiment. The inner needle assembly 446 is integrally molded to the needle hub 432 and includes a triggering portion 448 and a needle retaining portion 450. The triggering portion 448 is characterized by an interior surface 452, which defines an annular space 453 for receiving a pressure trigger 454, and an exterior surface 456, which is configured to mate with and activate a pressure fitting 458. The needle retaining portion 450 includes a bore 460 for receiving a needle 12 and a glue well 462 for receiving glue. The bore 460 is preferably slightly larger than the diameter of the needle, by about 0-3 thousandths of an inch. The needle 12 is fixed to the needle retaining portion 450 by first inserting the needle in through the bore 460 and then applying glue to the glue well 462 and allowing the glue to cure. Due to the clearance between the bore 460 and the needle 12, some residual glue may flow into the bore to bond with the needle and the needle hub inside the bore.

With reference to FIG. 19b in addition to FIG. 19a, the inner needle assembly 446 has a configuration that is generally clover shaped, but may optionally be oval, rectangular, or polygonal. The interior surface 452 of the triggering portion 448 of the inner needle assembly 446 has a width that approximately equals the outside diameter of the pressure trigger's 454 proximal cylindrical section 490. Two integrally molded actuators 464 having a bump shape (FIG. 19b) are formed upon the upper and lower surfaces 466a, 466b of the triggering portion 448 and protrudes into the annular space 453 of the interior surface 452 as well as into the space occupied by the pressure fitting, as further discussed below. When the pressure trigger 454 moves distally within the annular space 453 and contacts the actuators 464, their interaction causes the upper and lower surfaces 466a, 466b to radially expand, which in turn causes the arms 488a, 488b on the pressure fitting 458 to expand to release the restraining force on the resilient member 21. The inner needle assembly 446 is connected to the needle hub 432 by two integrally molded arms 468 shown in FIG. 19b.

Two male detents 470 are formed along the exterior surface 456 of the triggering portion 448. The male detents 470 are positioned just proximal of the actuators 464 and are configured to mate with a pair of hooks 472a, 472b located on the pressure fitting 458 in the ready position (FIG. 19a). The hooks 472a, 472b disengage from the male detents 470 to launch the pressure fitting, as further discussed below. As male detents 470 are configured to mate with female detents, the pair of hooks 472a, 472b, may be considered female detents. However, as hooks 472a, 472b are configured to mate with corresponding sockets or slots, the male detents 470 may also be considered female detents if the hooks were viewed as male detents.

Turning now to FIG. 19c in addition to FIGS. 19b and 19d, the pressure fitting 458 incorporated in the present embodiment includes a cylindrical section 474 that has a dome 476. The dome 476 further having a cavity located therein for receiving the spring clip 20 and an opening 475 for allowing the pressure fitting to move 458 relative to the needle 12 when launched. The cylindrical section 474 further includes a side opening 478 for dispensing glue therethrough (FIG. 19d). Similar to the end wall 291 on the pressure fitting 272 shown in FIGS. 14a and 14b, the dome 476 is formed by pressing the cylindrical section 474 into a steel form or die. Subsequent to forming the dome, the spring clip 20 is secured within the cavity and is protected against manipulation. Alternatively, the pressure fitting 458 can be formed from two molded parts and assembled over the spring clip 20.

Referring specifically to FIG. 19d, the pressure fitting 458 further includes a first flange 480 having a first diameter, a second flange 482 having a second diameter, and a third flange 484 having a third diameter connected to one another by a plurality of ribs 486. The first diameter of the first flange 480 is sized so that it fits within the annular space provided by the outer cylinder 440 of the needle hub 432 (FIG. 19a). The second diameter of the second flange 482 is sized so that the resilient member 21 may fit over the second flange (FIGS. 19a and 19b). Finally, the third diameter of the third flange 484 is sized so that it fits within the annular space provided by the inner cylinder 438 of the needle hub 432 (FIG. 19a). The cylindrical section 474 extends distally from the first flange 480.

Still referring to FIG. 19d, the elongated arms 488a, 488b extend proximally from the third flange 484 and terminate into a pair of hooks 472a, 472b. In the ready position (FIG. 19a), the hooks 472a, 472b interact with the male detents 470 of the triggering portion 448 to provide a restraining force on the resilient member 21 (FIG. 19a). In other words, in the ready position, the resilient member 21 is compressed by the first flange 480 of the pressure fitting 458 and the surface that forms the junction between the inner cylinder 438 and the outer cylinder 440.

The pressure trigger 454 incorporated in the present embodiment includes an active cylindrical section 490 that has an end face and a tapered section 492 at the junction between the end face and the cylindrical section. The pressure trigger 454 further includes a proximally extending plunger engagement arm 494, which has a bore 496 disposed therein for receiving fluids. Unlike some of the previously discussed embodiments, such as FIGS. 7a-9b, the active cylindrical section 490 of the pressure trigger 454 does not require an interference fit with the syringe tip engagement chamber 42 (other than perhaps a punctual interference so that the pressure trigger 454 does accidentally fall out of the needle hub from gravity alone). As readily apparent from the structure described, the annular space defined by the interior surface 452 of the inner needle assembly 446 is completely sealed from the exterior surface 456. Thus, once a syringe is connected to the hypodermic needle assembly 430 and the syringe tip engages the syringe tip engagement chamber 42, medicine that is discharged from the syringe can only flow one way out of the needle 12.

In use, connecting the luer fitting 188 to the threaded receptacle connects the hypodermic needle assembly 430 to the syringe. Concurrently therewith, the syringe tip 30 engages the syringe tip engagement chamber 42 in an interference fit. The plunger on the syringe is then moved distally to empty the syringe. At this point, liquid or medicine is drawn into the syringe by inserting the needle 12 into a medicine vial and then moving the plunger proximally to create a vacuum.

A patient is injected by inserting the needle tip 22 into the patient and then pressing the plunger to move the plunger tip distally. During the same plunger distal movement, after the medicine is completely injected into the patient, the extension pin 31a pushes the plunger engagement arm 494 of the pressure trigger 454 distally into the inner needle assembly 446. As the pressure trigger 454 moves distally into the annular space 453, the tapered section 492 on the pressure trigger 454 engages the actuators 464 and causes the actuators to expand radially outward. Concurrently therewith, the actuators 464 push against the elongated arms 488a, 488b to similarly expand the elongated arms radially outward. As the arms 488a, 488b radially expand, they move the hooks 472a, 472b a proportional radial distance, which causes the hooks to disengage from the male detents 470. Once so disengaged, the resilient member 21 releases its stored energy and expands distally, which pushes the pressure fitting 458 and which pushes the spring clip 20 distally to shield the needle tip 22.

A safety cap 498 is shown in FIGS. 19a and 19b for shielding the needle 12 during packaging and/or shipping.

The safety cap 498 is also preferably positioned over the needle until just prior to the point of use in order to reduce unintended needle stick. The safety cap 498 has a threaded base section 500 that is configured to engage with the needle hub 432.

As shown in the embodiments of the needle assembly described above with reference to FIGS. 1a-14c, 15c, 15d, and 19a-19d, the outer body 32 of the needle hub 14 is designed to facilitate manipulation of the needle hub 14 between the thumb and finger, for example, each end of the side walls may include a stepped portion or textured surface to facilitate gripping. In addition, in a preferred embodiment, the needle hub body 32 is made, for example, by injection molding a transparent material such as polypropylene, so that an ultraviolet light cured adhesive can be used to bond the needle 12 to the inner needle assembly 52 (e.g., FIGS. 6a-9b). The other components of the needle assembly, such as the various embodiments of the pressure trigger, the pressure fitting, the inner needle mounting assembly, and the spring clip housing, can also be formed from polypropylene by injection molding. If desired, the needle hub and the pressure trigger of the FIG. 3 embodiment, which incorporate a frangible seal formed between the pressure trigger flange and the syringe engagement chamber wall, can be formed by injection molding polystyrene. In embodiments of the invention in which the syringe 30 is a separate device which can be detachably attached to the needle hub 14, the proximal end of the needle hub 14 can optionally include attaching means, such as, for example, a frictional fitting or a luer lock 90, as shown in FIGS. 1-6.

The blocking portion of the needle guard 16 itself can comprise any device suitable to safely block the tip 22 of the needle 12. As shown in e.g., FIGS. 1a-7e and 9a-9b, in a preferred embodiment of the safety needle assembly of the present invention, the blocking portion of the needle guard 16 comprises an interlocking spring clip 20. Turning particularly to FIG. 1b, the spring clip 20 comprises elongated tensioning arms 92 which extend distally from the end wall 28 of the clip along the needle shaft 12. Two inwardly extending transverse wall portions 94a and 94b of the spring clip, having generally L-shaped extensions with curled lips on their ends, extend from the elongated arms 92 and project inwardly toward the longitudinal axis of the needle. In this embodiment, the transverse wall portions 94a and 94b, which are continuously resiliently urged towards the longitudinal axis by the action of the spring clip 20 design, are provided to engage the needle, such that the clip cannot be moved in a proximal direction. The end wall 28 of the spring clip 20 has a restraining opening 26 disposed therein to allow the needle 12 to pass therethrough. The restraining opening has a diameter which allows the spring clip 20 to slidingly move along the shaft of the needle 12 at the resilient urging of the spring 21, but when the clip has arrived near the needle tip, the opening engages the extended portion of the needle stop 24 to thereby prevent the clip 20 from being completely withdrawn from the needle tip 22. One embodiment of a spring clip useful in accordance with practice of the present invention is disclosed in U.S. Pat. No. 6,117,108, which is incorporated herein in its entirety by this reference.

In the embodiment of the safety hypodermic needle assembly provided in accordance with the practice of the invention shown in FIGS. 3a-3c, the spring clip 20 is substantially identical to the spring clip 20 described above and shown in FIGS. 1a-1c and 2a-2c. However, turning particularly to FIG. 3b, in this embodiment, the spring clip 20 is positioned inside the spring clip housing 50 which comprises proximal and distal needle openings 98a and 98b arranged such that the needle 12 can extend therethrough. The needle tip guard 16 of this embodiment is designed such that the needle tip 22 enters both the housing 50 and the needle tip spring clip 20. However, the spring clip 20 operates as described above, wherein the transversely biased spring arms 92 and associated transverse wall portions 94a and 94b engage to block the needle tip 22, and the restraining opening 26 in the end wall 28 is biased against needle stop 24 by the spring 21. In such an embodiment, it should be understood that the spring clip 20 may function to completely block the needle tip 22, even in the absence of the housing 50, and in fact the housing 50 may be designed such that it can be easily detached from the spring clip.

Although only one embodiment of the spring clip 20 is described above, it should be understood that any suitable spring clip design may be utilized, such that the spring clip operates to block the needle tip 22 via two separate mechanisms. Turning to FIGS. 1b-6b, for example, in one mechanism, the arms 92 of the spring clip 20 are designed to engage such that they block the needle tip 22 from being moved in a distal direction relative to the spring clip. In the second mechanism, the restraining opening 26 in the end wall 28 of the spring clip is designed such that the enlarged portion of the needle stop 24 engages therewith and thus prevents the needle 12 from being moved in the proximal direction relative to the spring clip. The spring clips disclosed herein are preferably of integral construction, and made from stainless steel or other suitable material having the necessary memory and spring characteristics.

During operation, the hypodermic needle assembly 10, either as an integral syringe unit or, preferably, as an attachment mounted over a separate syringe 30, as shown in any of FIGS. 1b-6b, 7a-9b, 10a-14c, 15c, 15d, and 19a-19d, is grasped by the user on the outer body 32 of the needle hub 14. The assembly 10 is oriented such that the needle tip 22 is positioned against the patient's skin. The needle 12 is then inserted into the patient. When the needle has successfully penetrated the patient, the syringe plunger 31 is urged distally forward, such that any fluids contained in the syringe are forced into the needle 12 in fluid communication therewith, in substantially the same way that conventional hypodermic needle syringes are used. Specifically, the needle hub 14 is utilized to position the needle 12 a selected distance into the patient and then the syringe plunger 31 is used to inject the desired medicants. As shown best in FIGS. 1b-6b and 7a-7b, during this operation and during the injection, the needle tip guard assembly 16 remains unactivated because the elongated extension pin 31a on the syringe plunger mechanically activates the pressure trigger 18, 112, 130 only after substantially all of the medicant has been injected.

When the medicant has been fully delivered, the syringe plunger extension pin 31a mechanically interacts with the pressure trigger (either by direct contact with the pressure trigger or through another structure). As the distal movement of the extension pin 31a applies a distally directed force on the pressure trigger, the engagement between the pressure trigger and the needle passageway is overcome, and the pressure trigger slides in a distal direction through the needle passageway. The movement of the slidable pressure trigger is then communicated to the associated pressure fitting, thereby disengaging the pressure fitting from the frictional engaging opening in the end wall of the spring clip cavity. This disengagement allows the compressed spring to resiliently urge the spring clip distally along the needle through the distal opening of the spring clip cavity and toward the needle tip. The spring clip moves along the needle until the arms of the spring clip move past the needle tip and are thereby free to spring closed, thereby blocking the distal path of the needle tip. Further distal movement of the spring clip is prevented by the interaction of the restraining opening in the end wall of the spring clip with the needle stop on the needle shaft or by any other suitable mechanism, such as, for example, a tether attaching the spring clip to the needle hub. In this position, the needle tip is prevented from re-emerging due to being shielded by the transverse portion of the spring clip, which forms a wall blocking the distal exit path of the needle tip, and the clip cannot be pulled off of the needle tip because of the engagement of the restraining opening with the needle stop. As is described below in detail, the spring clip can be engaged around the needle tip in a number of ways, according to the illustrative embodiments of the needle assembly of the present invention.

First, in the embodiment shown in FIGS. 1a-1c, the syringe plunger 31 is depressed, such that the extension pin 31a extends into the syringe tip engagement chamber 42 and out from the syringe tip. In this condition, the extension pin 31a engages the pressure trigger 18 that is frictionally held by the pressure trigger engaging opening 48 in the proximal end of the needle passageway 34. As the plunger presses against the pressure trigger 18, the pressure trigger and the needle 12 attached thereto are pushed in a distal direction through the needle passageway 34. The movement of the pressure trigger is transmitted through the compressed spring 21, to the spring clip pressure fitting 45 disposed within the spring clip engaging opening 46 in the distal end of the needle passageway 34. When the spring clip pressure fitting is urged out of the spring clip engaging opening, the compressed spring expands distally and urges the spring clip 20 out of the spring clip cavity 36 and distally along the needle 12 around which the spring clip is arranged. The spring clip and pressure fitting move along the length of the needle 12 until the needle stop 24 engages the restraining opening 26 in the end wall 28 of the spring clip. As shown in FIGS. 1b and 1c, when the spring clip 20 reaches the end of needle, such that the needle shaft 12 is no longer interposed between the lips 96 at the ends of the spring clip arms 92, the arms move by resilient action into the guard position blocking the needle tip 22. Retention of the spring clip guard on the needle in this position is ensured by the interlocking engaging arms 92 which prevent movement of the guard in the proximal direction and by the restraining opening 26 engaged with the needle stop 24 which prevents movement of the guard in the distal direction.

FIGS. 2a-2c show a second mechanism for engaging the needle tip guard assembly 16. In this embodiment, the plunger 31 is depressed, such that the extension pin 31a extends into the syringe tip engagement chamber 42 and out from the syringe tip. In this condition, the extension pin 31a engages the proximal end of the pressure trigger 18' which is frictionally held by the pressure trigger pressure fitting 47 in the pressure trigger engaging opening 48 in the proximal end portion of the needle passageway 34. As the plunger presses against the pressure trigger, the pressure trigger and the needle attached thereto are pushed in a distal direction through the needle passageway. The distal movement of the pressure trigger 18' is directly transmitted to the spring clip pressure fitting 45, which is in mechanical communication therewith, and which is disposed within the spring clip engaging opening 46 in the distal end of the needle passageway 34. When the spring clip pressure fitting 45 is urged out of the spring clip engaging opening 46, the compressed spring 21 expands distally and urges the spring clip 20, which can be fixedly attached to the pressure fitting, out from the spring clip cavity 36 distally along the needle 12 around which the spring clip 20 is arranged. The spring clip and pressure fitting move along the length of the needle 12 until the needle stop 24 engages the restraining opening 26 in the end wall 28 of the spring clip. As shown in FIGS. 2b and 2c, when the spring clip 20 reaches the end of needle such that the needle shaft 12 is no longer interposed between the lips 96 at the end of the spring clip arms 92, the arms move by resilient action into the guard position blocking the needle tip 22. Retention of the spring clip guard on the needle 12 in this position is ensured by the interlocking engaging arms 92 which prevent movement of the guard in the proximal direction and by the restraining opening 26 engaged with the needle stop 24 which prevents movement of the guard in the distal direction.

FIGS. 3a-3c show a third mechanism for engaging the needle tip guard assembly 16. In this embodiment, the syringe plunger 31 is depressed such that the extension pin 31a extends into the syringe tip engagement chamber 42 and out from the syringe tip. In this condition, the extension pin 31a engages the pressure trigger 18' held annularly by a frangible breakpoint or seal 48', which is annularly engaged with the inside surface of the wall of the syringe tip engagement chamber 42. As the plunger presses against the pressure trigger 18", the frangible seal 48' is broken and the pressure trigger and the needle 12 attached thereto are pushed in a distal direction through the needle passageway 34. The movement of the pressure trigger 18" is directly transmitted to the housing pressure fitting 51, which is in mechanical communication therewith and which is disposed within the housing engaging opening 46' in the distal end of the needle passageway 34. When the housing pressure fitting 51 is urged out of the housing engaging opening 46', the compressed spring 21 expands distally and urges the housing 50 and the spring clip 20 out of the spring clip cavity 36 distally along the needle 12 around which the housing and spring clip are arranged. The housing 50 and spring clip 20 move along the length of the needle 12 until the needle stop 24 engages the restraining opening 26 in the end wall 28 of the spring clip 20. As is shown in FIGS. 3b and 3c, when the spring clip 20 reaches the end of needle such that the needle shaft 12 is no longer interposed between the lips 96 at the end of the spring clip arms 92, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

FIGS. 4a-4c show a fourth mechanism for engaging the needle tip guard assembly 16. In this embodiment, the syringe plunger 31 is depressed such that the extension pin 31a extends into the syringe tip engagement chamber 42 and out from the syringe tip, such that the extension pin 31a engages the proximal end of the needle 12. As the extension pin 31a presses against the proximal end of the needle, the pressure trigger 18''' and the needle attached thereto are pushed in a distal direction through the needle passageway 34. The movement of the pressure trigger 18''' is directly transmitted to the pressure fitting 45' which is in mechanical communication therewith and which is disposed within the engaging opening 46" in the distal end of the needle passageway 34. When the pressure fitting 45' is urged out of the engaging opening 46", the compressed spring 21 expands distally and urges the spring clip 20 out of the spring clip cavity 36 distally along the needle 12. The pressure fitting 45' and spring clip 20 move along the length of the needle 12 until the needle stop 24 engages the restraining opening 26 in the end wall 28 of the spring clip 20. As shown in FIGS. 4b and 4c, when the spring clip 20 reaches the end of needle, such that the needle shaft 12 is no longer interposed between the lips 96 at the end of the arms 92 of the spring clip, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

FIG. 5a shows a fifth mechanism for engaging the needle tip guard assembly 16. In this embodiment, the activation mechanism is generally as described above with reference to FIGS. 4a-4c, except that the pressure trigger 18'''' further comprises at least one flexible hook 47a designed to engage the engaging opening 48'''. Accordingly, the needle guard activation process begins as before, where the syringe plunger 31 is depressed such that the syringe extension pin 31a extends into the syringe tip engagement chamber 42 and out from the syringe tip to thereby engage the engaging platform 47b of the pressure trigger 18''''. As the plunger extension pin 31a presses against the platform 47b, the flexible hook 47a is pressed inwardly such that it disengages from the engaging opening 48''', and the pressure trigger 18'''' and needle 12 attached thereto are pushed in a distal direction through the needle passageway 34. The movement of the pressure trigger 18'''' is directly transmitted to the pressure fitting 45' which is in mechanical communication therewith, and which is disposed within the engaging opening 46'' in the distal end of the needle passageway 34. When the pressure fitting 45' is urged out of the housing engaging opening 46'', the compressed spring expands distally and urges the spring 21 and the spring clip 20 out of the spring clip cavity 36 distally along the needle 12. The pressure fitting 45' and the spring clip 20 move along the length of the needle 12 until the needle stop 24 engages the restraining opening 26 in the end wall 28 of the spring clip 20. As was the case with the embodiment of FIGS. 4a-4c, when the spring clip 20 reaches the end of the needle such that the needle shaft is no longer interposed between the lips at the end of the arms of the spring clip, the arms move by resilient action into the guard position blocking the needle tip 22. Retention of the spring clip on the needle in this position is ensured by the interlocking engaging arms which prevent movement of the guard in the proximal direction and by the restraining opening 26 engaged with the needle stop 24 which prevents movement of the guard in the distal direction. In this embodiment the pressure trigger 18'''' is prevented from moving distally past the needle stop 49a''' by the engagement of the annular stop flange 49b and is prevented from moving proximally past the needle stop 49c when unactivated, and past the opening 48''' when activated, by the flexible hook 47a.

FIG. 5b shows a sixth mechanism for engaging the needle tip guard assembly 16. In this embodiment, the activation mechanism is generally as described above with reference to FIG. 5a, except that the assembly further comprises an intermediate pusher assembly 31b. Accordingly, the needle guard activation process begins by depressing the plunger 31 such that the extension pin 31a extends into the syringe tip which is mounted in the syringe tip engagement chamber 42. The pin 31a engages the elongated pin or arm 31c of the intermediate pusher assembly 31b which extends into the open syringe tip and thereby communicates the distal motion of the plunger to the engaging platform 47b of the pressure trigger 18''''. As the intermediate plunger assembly 31b presses against the platform 47b, the flexible hook 47a is pressed inwardly such that it disengages from the engaging opening 48''' (as shown in phantom in FIG. 5b), and the pressure trigger 18'''' and the needle 12 attached thereto are pushed in a distal direction through the needle passageway 34. The movement of the pressure trigger 18'''' is directly transmitted to the pressure fitting 45' which is in mechanical communication therewith and which is disposed within the engaging opening 46'' in the distal end of the needle passageway 34. The pressure fitting 45' is thereby urged out of the housing engaging opening 46'', and the compressed spring 21 expands distally and urges the pressure fitting 45' and the spring clip 20 out of the spring clip cavity 36 distally along the needle 12. Turning to FIG. 5c, when the spring clip 20 reaches the end of the needle such that the needle shaft 12 is no longer interposed between the lips 96 at the end of the arms 92 of the spring clip, the arms move by resilient action into a guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction. In this embodiment, the pressure trigger 18'''' is prevented from moving distally past the needle stop 49a''' by the engagement of the annular stop flange 49b and is prevented from moving proximally past the opening 48''', once activated, by the flexible hook 47a.

FIGS. 6a-6d show a seventh mechanism for engaging the needle tip guard assembly 16. In this embodiment, the plunger 31 engages the pressure trigger 18'''''' which has a plunger engaging portion or arm 86 which extends into the opening at the tip of the syringe 30. As the plunger presses against the pressure trigger 18'''''', the pressure trigger is pushed in a distal direction through the needle passageway 34 and against the pressure trigger fitting 45''. The movement of the pressure trigger 18'''''' is directly transmitted to the pressure fitting 45'' which has an enlarged distal end portion disposed in and frictionally engaged in the opening 46''' in the distal end of the needle passageway 34. In this embodiment, the needle 12 itself does not move relative to the needle passageway 34. When the enlarged distal end of the pressure fitting 45'' is urged out from the housing engaging opening 46''', the compressed spring 21 expands distally and urges the spring clip 20 out of the spring clip cavity 36 distally along the needle 12. The pressure trigger 18'''''' and spring clip 20 move along the length of the needle 12 until the needle stop 24 engages the restraining opening 26 in the end wall 28 of the spring clip. As shown in FIG. 6b, when the spring clip 20 reaches the end of needle, such that the needle shaft 12 is no longer interposed between the lips 96 at the ends of the arms of the spring clip, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

FIGS. 7a-9b, 10a, and 15c show the eighth, ninth, tenth, eleventh, and twelfth mechanisms ("eight-twelfth") for engaging the needle tip guard assembly. In the eighth-twelfth mechanisms, the plunger 31 engages the pressure trigger 112, 130, 278 which in turn engages the tapered ramps 110 via the pusher end 116, 340. As the pusher end 116, 340 moves distally to engage the ramps 110 on the pressure fitting, a force is generated which spreads the elongated arms radially outward. As the elongated arms spread radially outward, the male detents 102 or cut-outs 162 become disengaged from the stop 81. Once disengaged from the stop, the resilient member 21 is no longer restrained by the interaction of the male detents/cut-outs and the stop, the resilient member uncoils and expands distally. As the resilient member expands distally, it pushes on the distal end of the pressure fitting 100, 126, 154, 170, 342 thereby launching the pressure fitting distally. In the embodiment of FIGS. 7a, 9a, 10a, and 15c, when the pressure fitting moves distally, the spring clip 20 distal end resiliently closes over the needle tip 22 and blocks the needle tip from accidental contact. In the embodiment of FIGS. 8a and 8b, the pressure fitting 126 and the associated needle sheath 150 is launched along the needle and is stopped by the engagement of the hooks 136 with the circumferential end 140 of the shroud 138 wherein the needle tip is shielded from accidental contact.

FIGS. 12a-13b show the thirteenth and fourteenth mechanisms for engaging the needle tip guard assembly. In the thirteenth and fourteenth mechanisms, the plunger engages the pressure trigger 226, which in turn directly contacts and pushes the spring clip 20, 260. Upon being pushed by the pressure trigger 226 with sufficient force, the spring clip 20, 260 separates from the undercut or groove 192, 252 located on the needle hub housing. Upon its separation from the needle hub housing, the spring clip 20, 260 is pushed distally by the expanding resilient member 21, 231 until the opening located on the spring clip abuts the stop member 24 located on the needle shaft. At which point, the spring clip 20, 260 blocks the needle tip from inadvertent contact with the needle tip.

FIGS. 11a and 11b show a fifteenth mechanism for engaging the needle tip guard assembly. In the fifteenth mechanism, the plunger on the syringe engages the pressure trigger 210, which in turn directly contacts a washer 206. The washer 206 is in contact with the resilient member 21, and when it is so pushed by the pressure trigger 210, it further compresses the resilient member. The resilient member 21 in turn, pushes against the spring clip 20, which is engaged with the undercut or groove 192 located on the needle hub housing. When the force exerted by the resilient member 21 on the spring clip 20 is sufficiently great, it overcomes the gripping force provided by the engagement between the spring clip and the undercut 192, which then causes the spring clip to separate from the undercut. When this occurs, the resilient member 21 releases its energy and expands distally outward, which in turn pushes the spring clip distally to block the needle tip from inadvertent contact with the needle tip.

FIG. 14a shows a sixteenth mechanism for engaging the needle tip guard assembly. In the sixteenth mechanism, the plunger on the syringe engages the pressure trigger 278 and transfers its distal force, when pushed, to the pressure trigger. The pressure trigger 278 is in contact with a pressure fitting 272, which is engaged to the needle hub housing via a detent engagement with the housing. Accordingly, when the pressure trigger 278 exerts a sufficient distal force to the pressure fitting 272, the gripping force formed by the detent engagement is overcome and the shroud separates from the needle hub housing. When the pressure fitting finally separates from the needle hub, it is launched distally by the expanding action of the resilient member 21. Because the pressure fitting is in contact with the spring clip 20, the spring clip also launches distally to block the needle tip from inadvertent contact therewith.

FIGS. 19a-19d show a seventeenth mechanism for engaging the needle tip guard assembly. In the seventeenth mechanism, the plunger on the syringe engages the pressure trigger 454 and transfers its distal force, when pushed by a user, to the pressure trigger. The pressure trigger 454 then engages a pair of actuators 464, which are formed upon the trigger portion 448 of the inner needle assembly 446. When this occurs, the actuators 464 expand radially outward to abut the elongated arms 488a, 488b of the pressure fitting 458. The elongated arms 488a, 488b then expand radially outward to cause a pair of hooks 472a, 472b to disengage from corresponding male detents 470. As the hooks 472a, 472b separate from the male detents 470, the pressure fitting 458 launches distally due to the expanding action of the resilient member 21. Because the pressure fitting 458 is in contact with the spring clip 20, the spring clip also launches distally to block the needle tip from inadvertent contact therewith.

Regardless of the specific embodiment of the hypodermic needle assembly of the present invention, in each such embodiment, as the syringe plunger is advanced into the syringe, expelling the medication into the patient, the plunger extension pin 31a biases a pressure trigger longitudinally in the distal direction such that the spring clip guard 20 is automatically launched via a resilient member such as a spring along the length of a needle and over the end of the needle tip. The needle tip is therefore passively shielded by the action of pushing a syringe plunger into a syringe which has an extension pin which extends at least part way into the syringe tip. As the needle clip assembly 16 is passively actuated, the user is not required to perform any operations outside of those employed using conventional hypodermic needles. There is accordingly no need to learn any additional procedures in order to use the hypodermic needle assembly 10 according to the invention. The combined actions of the needle tip guard spring arms 92 and the needle stop 24 cause the spring clip 20 to be permanently locked in place once the injection procedure has been completed. During operation, there is only minimal frictional engagement between the spring clip 20, the needle shaft 12, and the needle hub 14. This design, ensures that the spring clip 20 will move along the needle 12 to the needle tip 22 without becoming detached therefrom or stuck thereon until the end wall 28 of the spring clip 20 engages the needle stop.

Further regarding the syringes 306, 379, 400 shown in FIGS. 16, 17, and 18a-18b, the preferred usage is to aspirate a compressible fluid such as air into the syringe; attach a needle to the syringe; puncture a sealed vial; inject air into the sealed vial; aspirate an incompressible fluid such as liquid medication from the vial into the syringe; remove the needle from the vial; stick the patient; and then inject the full contents in the syringe into the patient. The syringes 306, 379, 400 allow this preferred usage without prematurely activating the resilient member before the patient is stuck. The resilient member is activated at the end of the injection stroke into the patient so that as the needle is removed from the patient, the resilient member continues to launch the pressure fitting and the spring clip until the needle tip exits the patient and simultaneously is blocked by the spring clip to prevent inadvertent needlestick injuries.

Although limited embodiments of the hypodermic needle assembly and its components have been specifically described and illustrated herein, many modifications and variations will be apparent to those skilled in the art. Accordingly, it is to be understood that the hypodermic needle assembly and its components constructed according to principles of this invention may be embodied other than as specifically described herein. The invention is defined in the following claims.

What is claimed is:

1. A safety hypodermic needle assembly comprising:
   a needle hub having an inner needle assembly, a proximal end and a distal end, the proximal end comprising a threaded member and a syringe tip receiving chamber, and the distal end comprising an opening;
   a needle secured to the inner needle assembly and having a needle tip;
   a resilient member;

a spring clip for obstructing the needle tip movable by the resilient member to a blocking position;

a pressure trigger having a fluid path, an opening, and a pusher end axially aligned with the syringe tip receiving chamber and slidably movable relative thereto;

a pressure fitting having an elongated arm and a tapered ramp disposed on the elongated arm, the pressure fitting is configured to compress the resilient member when the needle assembly is in a ready position by engaging with the inner needle assembly; and wherein the spring clip is configured to block the needle tip when the pressure trigger is moved distally within the syringe tip receiving chamber to disengage the pressure fitting from the inner needle assembly.

2. The safety hypodermic needle assembly of claim 1, wherein the inner needle assembly comprises a male detent on an exterior surface.

3. The safety hypodermic needle assembly of claim 1, wherein the inner needle assembly comprises a stop member and the pressure fitting comprises a male detent, and wherein the male detent is configured to engage the stop member to hold the resilient member in a compressed state.

4. The safety hypodermic needle assembly of claim 1, wherein the inner needle assembly comprises an annular space.

5. The safety hypodermic needle assembly of claim 1, wherein the pusher end is configured to interact with the tapered ramp to impart a pair of component forces, and wherein when the pusher end interacts with the tapered ramp, the elongated arm moves radially to disengage the pressure fitting from the inner needle assembly.

6. The safety hypodermic needle assembly of claim 1, further comprising a protective cap attached to the distal end of the needle hub.

7. The safety hypodermic needle assembly of claim 1, wherein the pressure fitting further comprises a second elongated arm.

8. The safety hypodermic needle assembly of claim 7, wherein the pusher end is configured to interact with the tapered ramp to impart a pair of component forces, and wherein when the pusher end interacts with the tapered ramp, the elongated arm moves radially to disengage the pressure fitting from the inner needle assembly.

9. The safety hypodermic needle assembly of claim 1, wherein the inner needle assembly comprises a raised bump.

10. The safety hypodermic needle assembly of claim 1, wherein the pusher end of the pressure trigger is configured to abut the inner needle assembly to limit the distal travel of the pressure trigger.

11. The safety hypodermic needle assembly of claim 1, wherein the pressure fitting comprises a gripping finger for gripping a portion of the spring clip.

12. A safety hypodermic needle assembly comprising a needle hub having an outer cylinder and an inner cylinder and an annular space defined thereinbetween, the needle hub further comprising a proximal end having a fitting and a distal end;

an inner needle assembly comprising a triggering portion and a needle retaining portion; the needle retaining portion having a needle extending distally therefrom and the triggering portion comprising an interior surface and an exterior surface; the interior surface defining a pressure trigger receiving chamber and comprising a first interior bump, the exterior surface comprising a male detent and a first exterior bump;

a pressure fitting comprising a flange, a cylinder extending distally from the flange, and an elongated arm extending proximally from the flange; the elongated arm further comprising a hook for engaging with the male detent located on the inner needle assembly, a resilient member compressed within the annular space when the hook is engaged with the male detent; and a pressure trigger comprising a cylindrical portion defining a bore, the pressure trigger is configured to engage with and radially expand the first interior bump located on the interior surface of the triggering portion.

13. The safety hypodermic needle assembly of claim 12, further comprising a second male detent on the exterior surface of the triggering portion and a second elongated arm having a hook extending proximally from the flange on the pressure fitting.

14. The safety hypodermic needle assembly of claim 13, wherein the hooks on the two elongated arms are engaged with the two male detents.

15. The safety hypodermic needle assembly of claim 14, wherein the flange compresses against the resilient member's distal end when the two hooks are engaged with the two male detents.

16. The safety hypodermic needle assembly of claim 14, wherein the interior surface comprises an upper interior surface and a lower interior surface, the first interior bump is located on the upper interior surface, and a second interior bump is formed on the lower interior surface; and the exterior surface comprises an upper exterior surface and a lower exterior surface, the first exterior bump is located on the upper exterior surface, and a second exterior bump is formed on the lower exterior surface.

17. The safety hypodermic needle assembly of claim 16, wherein when the pressure trigger moves distally inside the pressure trigger receiving chamber of the triggering portion, the cylindrical portion of the pressure trigger interacts with the first interior bump and the second interior bump to move the two interior bumps radially outward.

18. The safety hypodermic needle assembly of claim 17, wherein the radial movement of the two interior bumps causes the two exterior bumps to radially move the two elongated arms radially outwardly to disengage the two hooks from the two male detents, which in turn releases the resilient member so that it expands distally of the annular space.

19. The safety hypodermic needle assembly of claim 18, further comprising a needle tip, a needle stop, and a spring clip disposed over the needle and positioned adjacent the pressure fitting; and wherein when the resilient member expands distally with respect to the annular space, the resilient member launches the spring clip towards the needle stop to shield the needle tip.

20. The safety hypodermic needle assembly of claim 19, further comprising a safety cap positioned over the needle and engaged to the needle hub.

21. The safety hypodermic needle assembly of claim 12, wherein the distally extending cylinder on the pressure fitting further comprises a dome and an opening located on the dome.

22. The safety hypodermic needle assembly of claim 21, wherein the dome is formed by pressing the distally extending cylinder into a form or a die.

23. A safety hypodermic needle assembly for mounting to a tip of a syringe comprising a needle hub, a pressure fitting, a pressure trigger, and a resilient member in contact with both the needle hub and the pressure fitting and being compressed by the pressure fitting; wherein:

the needle hub comprises a structure mechanically coupled to a needle having a needle tip, an inlet defining a syringe tip engagement chamber sized to receive a syringe tip, and one of a male detent and female detent;

the pressure fitting comprises a distal opening having the needle extending therethrough and an elongated arm extending proximally in the direction of the inlet of the needle hub, wherein the arm comprises the other one of the male detent and female detent; and the male detent is configured to engage the female detent in an unactivated position to compress the resilient member and the pressure trigger is configured to slide distally inside the syringe tip engagement chamber to interact with the needle hub to impart a radially outward force on the elongated arm to thereby disengage the male detent from the female detent.

24. The safety hypodermic needle assembly according to claim 23, wherein the pressure fitting comprises an end cap having the distal opening.

25. The safety hypodermic needle assembly according to claim 23, wherein the resilient member comprises a spring.

26. The safety hypodermic needle assembly according to claim 23, further comprising a spring clip for shielding the needle tip.

27. The safety hypodermic needle assembly according to claim 23, wherein the needle hub comprises an inner cylinder and an outer cylinder.

28. The safety hypodermic needle assembly according to claim 27, wherein the resilient member is located in a space between the inner cylinder and the outer cylinder.

29. The safety hypodermic needle assembly according to claim 27, wherein the outer cylinder comprises a slot.

30. The safety hypodermic needle assembly according to claim 23, wherein the pressure fitting comprises a second elongated arm extending proximally opposite the distal opening.

31. The safety hypodermic needle assembly according to claim 23, further comprising an inner needle assembly engaging the needle.

32. The safety hypodermic needle assembly according to claim 23, wherein the needle hub further comprises a triggering portion having an exterior surface and an interior surface defining an annular space.

33. The safety hypodermic needle assembly according to claim 23, wherein a syringe comprising a plunger and a barrel comprising a syringe tip is coupled to the needle hub.

* * * * *